(12) United States Patent
Matthews et al.

(10) Patent No.: US 7,807,838 B2
(45) Date of Patent: Oct. 5, 2010

(54) METHODS FOR THE PREPARATION OF HCV POLYMERASE INHIBITORS

(75) Inventors: Christopher Frederick Matthews, San Diego, CA (US); Robert William Scott, San Mateo, CA (US); John Lloyd Tucker, San Diego, CA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 12/064,747

(22) PCT Filed: Aug. 16, 2006

(86) PCT No.: PCT/IB2006/002342

§ 371 (c)(1),
(2), (4) Date: Sep. 18, 2008

(87) PCT Pub. No.: WO2007/023381

PCT Pub. Date: Mar. 1, 2007

(65) Prior Publication Data

US 2009/0023921 A1 Jan. 22, 2009

Related U.S. Application Data

(60) Provisional application No. 60/711,042, filed on Aug. 24, 2005, provisional application No. 60/744,273, filed on Apr. 4, 2006, provisional application No. 60/804,644, filed on Jun. 13, 2006.

(51) Int. Cl.
*C07D 213/55* (2006.01)
(52) U.S. Cl. .................................................. 546/342
(58) Field of Classification Search ....................... None
See application file for complete search history.

(56) References Cited

U.S. PATENT DOCUMENTS

2005/0176701 A1 8/2005 Borchardt

FOREIGN PATENT DOCUMENTS

WO WO 03095441 11/2003
WO WO 2006018725 2/2006

OTHER PUBLICATIONS

Boyer, et al., *J. Med. Chem.*, vol. 43, pp. 843-858 (2000).

*Primary Examiner*—James O Wilson
*Assistant Examiner*—Jeffrey H Murray
(74) *Attorney, Agent, or Firm*—Jennifer Kispert; J. Michael Dixon

(57) ABSTRACT

The present invention relates to methods and compounds useful in the preparation of compounds of the formula (I).

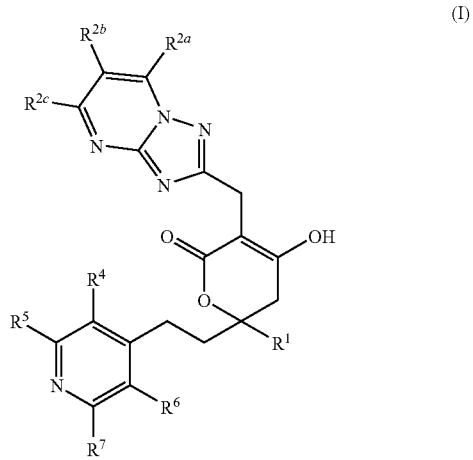

1 Claim, 3 Drawing Sheets

METHODS FOR THE PREPARATION OF HCV POLYMERASE INHIBITORS

This application claims priority under 35 U.S.C. §119(e) to U.S. Provisional Application Nos. 60/711,042, filed Aug. 24, 2005, 60/744,273, filed Apr. 4, 2006, and 60/804,644, filed Jun. 13, 2006, all of which are hereby incorporated by reference in their entirety.

FIELD

The present invention relates to methods for the preparation of compounds useful as inhibitors of the Hepatitis C virus (HCV) polymerase enzyme, and intermediate compounds useful in their preparation.

BACKGROUND

Hepatitis C virus (HCV) is a member of the hepacivirus genus in the family Flaviviridae. It is the major causative agent of non-A, non-B viral hepatitis and is the major cause of transfusion-associated hepatitis and accounts for a significant proportion of hepatitis cases worldwide. Although acute HCV infection is often asymptomatic, nearly 80% of cases resolve to chronic hepatitis. The persistent property of the HCV infection has been explained by its ability to escape from the host immune surveillance through hypermutability of the exposed regions in the envelope protein E2 (Weiner, et al., *Virology*, 180:842-848 (1991); Weiner, et al., *Proc. Natl. Acad. Sci. USA*, 89:3468-3472 (1992).

Since persistent infection of HCV is related to chronic hepatitis and eventually to hepatocarcinogenesis, HCV replication is one of the targets to eliminate HCV reproduction and to prevent hepatocellular carcinoma. Unfortunately, present treatment approaches for HCV infection are characterized by relatively poor efficacy and an unfavorable side-effect profile. Therefore, intensive effort is directed at the discovery of molecules to treat this disease, including the discovery of drugs designed to inhibit HC replication, as there is a persistent need for non-peptide, small-molecule compounds that are HCV RdRp inhibitors having desirable or improved physical and chemical properties appropriate for pharmaceutical applications.

Compounds useful as inhibitors of the HCV polymerase enzyme are disclosed in U.S. patent application Ser. Nos. 10/718,337, filed Nov. 19, 2003, and 11/204,269, Aug. 15, 2005, both of which are hereby incorporated by reference in their entirety. The present invention provides improved methods and intermediate compounds useful in the preparation of compounds useful as inhibitors of the HCV polymerase enzyme.

SUMMARY

The present invention provides methods of preparing compounds of formula (Ia):

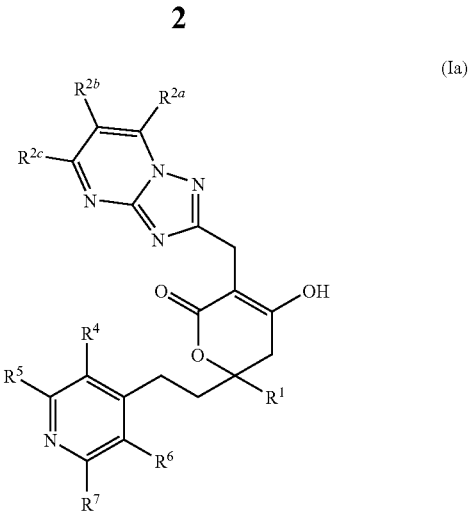

wherein:

$R^1$ is $C_1$-$C_6$ alkyl or $C_3$-$C_6$ cycloalkyl;

$R^{2a}$, $R^{2b}$, and $R^{2c}$ are each independently selected from hydrogen, halogen, $C_1$-$C_6$ alkyl, $C_3$-$C_6$ cycloalkyl, —$OR^{12a}$, —$CF_3$, —CN, and —$NR^{12a}R^{12b}$;

$R^4$ is selected from hydrogen, $C_1$-$C_6$ alkyl, —$(CR^9R^{10})_n R^{11}$, —$CF_3$, halogen, —$OR^{12a}$, —CN, and —$NR^{12a}R^{12b}$;

$R^5$ is selected from hydrogen, $C_1$-$C_6$ alkyl, —$(CR^9R^{10})_n R^{11}$, —$CF_3$, halogen, —$OR^{12a}$, —CN, and —$NR^{12a}R^{12b}$;

$R^6$ is selected from hydrogen, $C_1$-$C_6$ alkyl, —$(CR^9R^{10})_n R^{11}$, —$CF_3$, halogen, —$OR^{12a}$, —CN, and —$NR^{12a}R^{12b}$;

$R^7$ is selected from hydrogen, $C_1$-$C_6$ alkyl, —$(CR^9R^{10})_n R^{11}$, —$CF_3$, halogen, —$OR^{12a}$, —CN, and —$NR^{12a}R^{12b}$;

each $R^9$ and $R^{10}$ is independently selected from hydrogen and $C_1$-$C_6$ alkyl, or $R^9$ and $R^{10}$, together with the carbon atom to which they are attached, form a $C_3$-$C_6$ cycloalkyl group;

each $R^{11}$ is independently selected from hydrogen, $C_1$-$C_6$ alkyl, halogen, —$OR^{12a}$, —CN, —$CF_3$, and —$NR^9R^{10}$;

each $R^{12a}$ and $R^{12b}$ is independently selected from hydrogen and $C_1$-$C_6$ alkyl; and each n is independently chosen and is an integer from 0 to 5;

said method comprising:

a) treating a compound of formula (V), wherein $R^1$ is defined above, with an anion of a compound of formula (X), wherein $R^{13}$ is hydrogen, $C_1$-$C_6$ alkyl, —$Si(C_1$-$C_6$ alkyl$)_3$, or —$CH_2(C_6$-$C_{10}$ aryl), wherein said $C_6$-$C_{10}$ aryl group is optionally substituted with at least one substituent selected from halogen, $C_1$-$C_6$ alkyl, —OH, —$OCH_3$, and —$N(C_1$-$C_6$ alkyl$)_2$, to afford a compound of formula (IV);

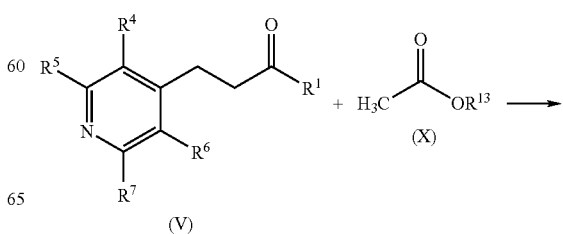

-continued

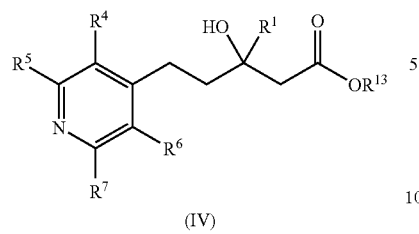

(IV)

b) hydrolyzing the compound of formula (IV) to afford a compound of formula (IV) wherein $R^{13}$ is hydrogen;

c) treating the compound of formula (IV) with a combination of reagents to afford a compound of formula (III), wherein $P^1$ is hydrogen or a suitable protecting group and $R^{14}$ is $C_1$-$C_6$ alkyl or —$CH_2(C_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$;

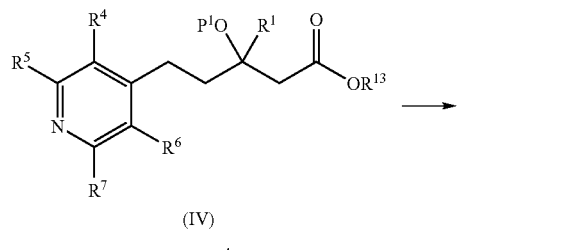

(IV)

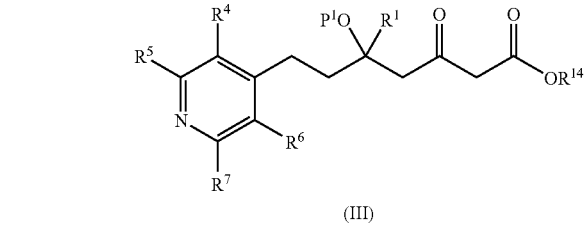

(III)

d) treating the compound of formula (III) with an acid or base to afford a compound of formula (II); and

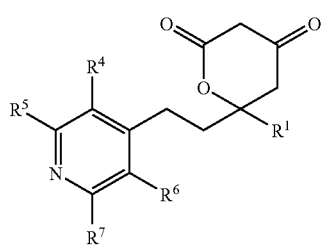

(II)

e) treating the compound of formula (II) with a compound of formula (IXa), to afford the compound of formula (Ia)

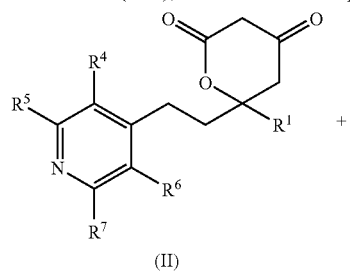

(II)

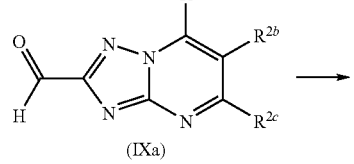

(IXa)

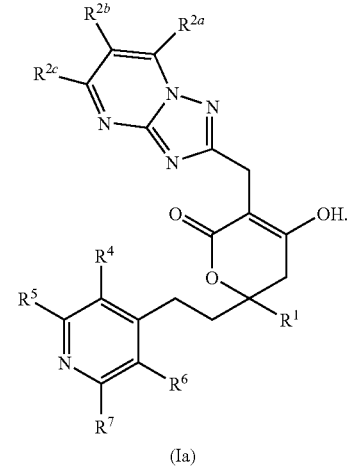

(Ia)

Further provided herein are such methods, wherein in the compound of formula (Ia):
$R^1$ is $C_3$-$C_6$ cycloalkyl;
$R^{2a}$, $R^{2b}$, and $R^{2c}$ are each independently selected from hydrogen, halogen, $C_1$-$C_6$ alkyl, $C_3$-$C_6$ cycloalkyl, —OR$^{12a}$, —CF$_3$, —CN, and —NR$^{12a}$R$^{12}$;
$R^4$ is selected from hydrogen, $C_1$-$C_6$ alkyl, —(CR$^9$R$^{10}$)$_n$R$^{11}$, —CF$_3$, halogen, —OR$^{12a}$, —CN, and —NR$^{12a}$R$^{12b}$;
$R^5$ is selected from hydrogen, $C_1$-$C_6$ alkyl, —(CR$^9$R$^{10}$)$_n$R$^{11}$, —CF$_3$, halogen, —OR$^{12a}$, —CN, and —NR$^{12a}$R$^{12b}$;
$R^6$ is selected from hydrogen, $C_1$-$C_6$ alkyl, —(CR$^9$R$^{10}$)$_n$R$^{11}$, —CF$_3$, halogen, —OR$^{12a}$, —CN, and —NR$^{12a}$R$^{12b}$;
$R^7$ is selected from hydrogen, $C_1$-$C_6$ alkyl, —(CR$^9$R$^{10}$)$_n$R$^{11}$, —CF$_3$, halogen, —OR$^{12a}$, —CN, and —NR$^{12a}$R$^{12b}$;
each $R^9$ and $R^{10}$ is independently selected from hydrogen and $C_1$-$C_6$ alkyl, or $R^9$ and $R^{10}$, together with the carbon atom to which they are attached, form a $C_3$-$C_6$ cycloalkyl group;
each $R^{11}$ is independently selected from hydrogen, $C_1$-$C_6$ alkyl, halogen, —OR$^{12a}$, —CN, —CF$_3$, and —NR$^{12a}$R$^{12b}$;
each $R^{12a}$ and $R^{12b}$ is independently selected from hydrogen and $C_1$-$C_6$ alkyl; and
each n is independently chosen and is an integer from 0 to 5.

Also provided herein are such methods, wherein in the compound formula (Ia):
$R^1$ is cyclopentyl;
$R^{2a}$, $R^{2b}$, and $R^{2c}$ are each independently selected from hydrogen, halogen, and $C_1$-$C_6$ alkyl;
$R^4$ is selected from hydrogen, $C_1$-$C_6$ alkyl, —(CR$^9$R$^{10}$)$_n$R$^{11}$, —CF$_3$, halogen, —OR$^{12a}$, —CN, and —NR$^{12a}$R$^{12b}$;
$R^5$ is selected from hydrogen, $C_1$-$C_6$ alkyl, —(CR$^9$R$^{10}$)$_n$R$^{11}$, —CF$_3$, halogen, —OR$^{12a}$, —CN, and —NR$^{12a}$R$^{12b}$;
$R^6$ is selected from hydrogen, $C_1$-$C_6$ alkyl, —(CR$^9$R$^{10}$)$_n$R$^{11}$, —CF$_3$, halogen, —OR$^{12a}$, —CN, and —NR$^{12a}$R$^{12b}$;
$R^7$ is selected from hydrogen, $C_1$-$C_6$ alkyl, —(CR$^9$R$^{10}$)$_n$R$^{11}$, —CF$_3$, halogen, —OR$^{12a}$, —CN, and —NR$^{12a}$R$^{12b}$;
each $R^9$ and $R^{10}$ is independently selected from hydrogen and $C_1$-$C_6$ alkyl, or $R^9$ and $R^{10}$, together with the carbon atom to which they are attached, form a $C_3$-$C_6$ cycloalkyl group;
each $R^{11}$ is independently selected from hydrogen, $C_1$-$C_6$ alkyl, halogen, —OR$^{12a}$, —CN, —CF$_3$, and —NR$^{12a}$R$^{12b}$;

each $R^{12a}$ and $R^{12b}$ is independently selected from hydrogen and $C_1$-$C_6$ alkyl; and each n is independently chosen and is an integer from 0 to 5.

Further included are such methods, wherein in the compound formula (Ia):
$R^1$ is cyclopentyl;
$R^{2a}$ is $C_1$-$C_6$ alkyl;
$R^{2b}$ is hydrogen;
$R^{2c}$ is $C_1$-$C_6$ alkyl;
$R^4$ is hydrogen;
$R^5$ is $C_1$-$C_6$ alkyl;
$R^6$ is hydrogen; and
$R^7$ is $C_1$-$C_6$ alkyl.

In another aspect are afforded such methods, wherein in the compound formula (Ia):
$R^1$ is cyclopentyl;
$R^{2a}$ is —$CH_3$;
$R^{2b}$ is hydrogen;
$R^{2c}$ is —$CH_3$;
$R^4$ is hydrogen;
$R^5$ is —$CH_2CH_3$;
$R^6$ is hydrogen; and
$R^7$ is —$CH_2CH_3$.

In still another aspect are afforded such methods, wherein the compound of formula (Ia) is (Iaa),

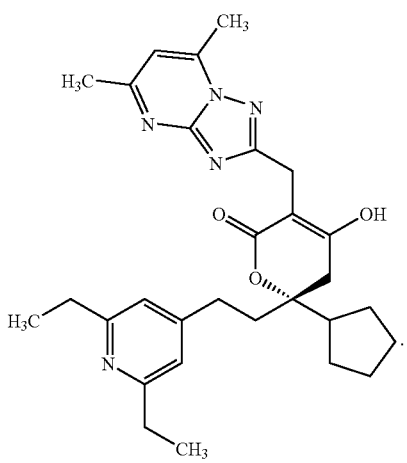

(Iaa)

Furthermore, included herein are such methods, wherein the compound of formula (Ia) is (Iab),

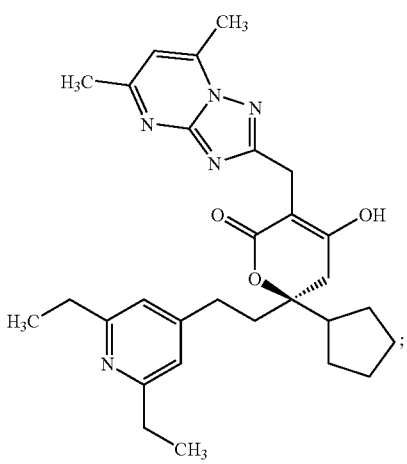

(Iab)

Further provided herein are methods of preparing a compound of formula (Ia):

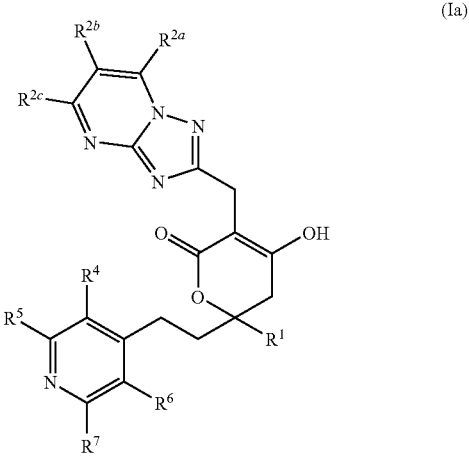

(Ia)

wherein:
$R^1$ is $C_1$-$C_6$ alkyl or $C_3$-$C_6$ cycloalkyl;
$R^{2a}$, $R^{2b}$, and $R^{2c}$ are each independently selected from hydrogen, halogen, $C_1$-$C_6$ alkyl, $C_3$-$C_6$ cycloalkyl, —$OR^{12a}$, —$CF_3$, —CN, and —$NR^{12a}R^{12b}$;
$R^4$ is selected from hydrogen, $C_1$-$C_6$ alkyl, —$(CR^9R^{10})_n$$R^{11}$, —$CF_3$, halogen, —$OR^{12a}$, —CN, and —$NR^{12a}R^{12b}$;
$R^5$ is selected from hydrogen, $C_1$-$C_6$ alkyl, —$(CR^9R^{10})_n$$R^{11}$, —$CF_3$, halogen, —$OR^{12a}$, —CN, and —$NR^{12a}R^{12b}$;
$R^6$ is selected from hydrogen, $C_1$-$C_6$ alkyl, —$(CR^9R^{10})_n$$R^{11}$, —$CF_3$, halogen, —$OR^{12a}$, —CN, and —$NR^{12a}R^{12b}$;
$R^7$ is selected from hydrogen, $C_1$-$C_6$ alkyl, —$(CR^9R^{10})_n$$R^{11}$, —$CF_3$, halogen, —$OR^{12a}$, —CN, and —$NR^{12a}R^{12b}$;
each $R^9$ and $R^{10}$ is independently selected from hydrogen and $C_1$-$C_6$ alkyl, or $R^9$ and $R^{10}$, together with the carbon atom to which they are attached, form a $C_3$-$C_6$ cycloalkyl group;
each $R^{11}$ is independently selected from hydrogen, $C_1$-$C_6$ alkyl, halogen, —$OR^{12a}$, —CN, —$CF_3$, and —$NR^{12a}R^{12b}$;
each $R^{12a}$ and $R^{12b}$ is independently selected from hydrogen and $C_1$-$C_6$ alkyl; and
each n is independently chosen and is an integer from 0 to 5;

said method comprising:
a) treating a compound of formula (IV), wherein $R^1$, $R^4$, $R^5$, $R^6$, and $R^7$ are as defined herein, $P^1$ is hydrogen or a suitable protecting group, and $R^{13}$ is hydrogen, $C_1$-$C_6$ alkyl, —Si($C_1$-$C_6$ alkyl)$_3$, or —$CH_2$($C_6$-$C_{10}$ aryl), wherein said $C_6$-$C_{10}$ aryl group is optionally substituted with at least one substituent selected from halogen, $C_1$-$C_6$ alkyl, —OH, —$OCH_3$, and —N($C_1$-$C_6$ alkyl)$_2$, with a combination of reagents to afford a compound of formula (III), wherein $R^{14}$ is $C_1$-$C_6$ alkyl, —Si($C_1$-$C_6$ alkyl)$_3$, or —$CH_2$($C_6$-$C_{10}$ aryl), wherein said $C_6$-$C_{10}$ aryl group is optionally substituted with at least one substituent selected from halogen, $C_1$-$C_6$ alkyl, —OH, —$OCH_3$, and —N($C_1$-$C_6$ alkyl)$_2$;

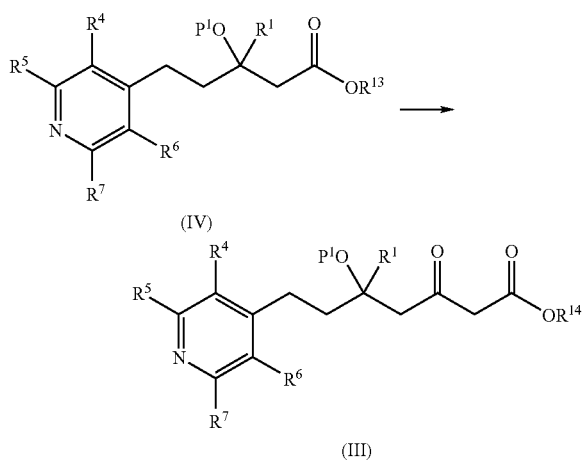

(IV)

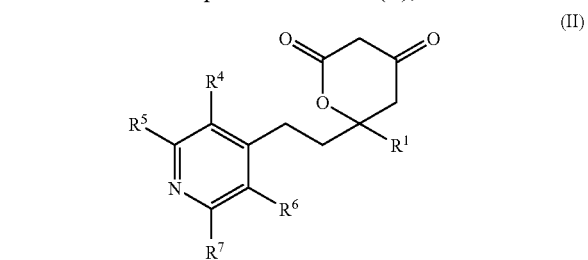

(III)

b) treating the compound of formula (III) with an acid or base to afford a compound of formula (II); and

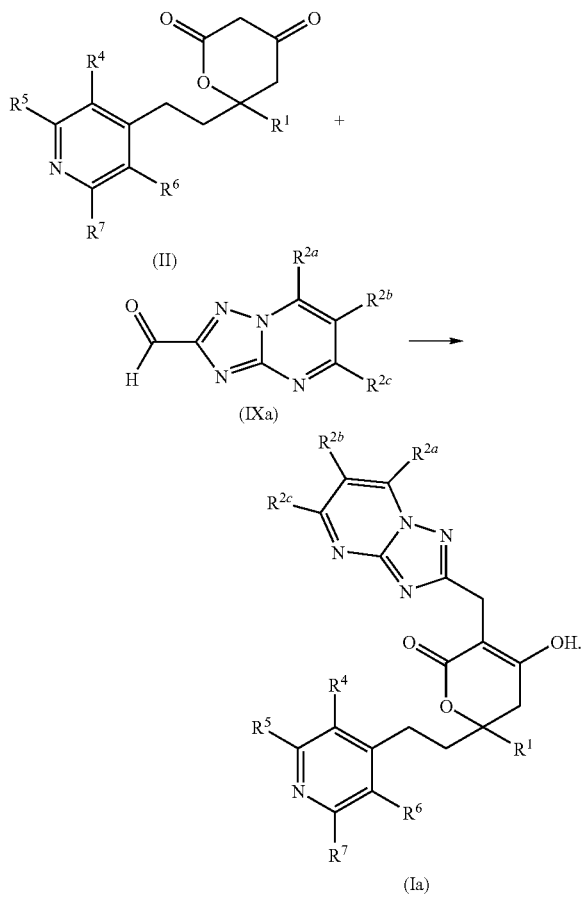

In still another aspect are provided methods of preparing a compound of formula (II),

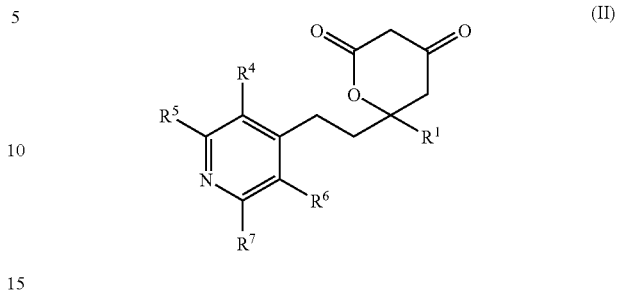

wherein:

$R^1$ is $C_1$-$C_6$ alkyl or $C_3$-$C_6$ cycloalkyl;

$R^4$ is selected from hydrogen, $C_1$-$C_6$ alkyl, $-(CR^9R^{10})_n R^{11}$, $-CF_3$, halogen, $-OR^{12a}$, $-CN$, and $-NR^{12a}R^{12b}$;

$R^5$ is selected from hydrogen, $C_1$-$C_6$ alkyl, $-(CR^9R^{10})_n R^{11}$, $-CF_3$, halogen, $-OR^{12a}$, $-CN$, and $-NR^{12a}R^{12b}$;

$R^6$ is selected from hydrogen, $C_1$-$C_6$ alkyl, $-(CR^9R^{10})_n R^{11}$, $-CF_3$, halogen, $-OR^{12a}$, $-CN$, and $-NR^{12a}R^{12b}$;

$R^7$ is selected from hydrogen, $C_1$-$C_6$ alkyl, $-(CR^9R^{10})_n R^{11}$, $-CF_3$, halogen, $-OR^{12a}$, $-CN$, and $-NR^{12a}R^{12b}$;

each $R^9$ and $R^{10}$ is independently selected from hydrogen and $C_1$-$C_6$ alkyl, or $R^9$ and $R^{10}$, together with the carbon atom to which they are attached, form a $C_3$-$C_6$ cycloalkyl group;

each $R^{11}$ is independently selected from hydrogen, $C_1$-$C_6$ alkyl, halogen, $-OR^{12a}$, $-CN$, $-CF_3$, and $-NR^9R^{10}$;

each $R^{12a}$ and $R^{12b}$ is independently selected from hydrogen and $C_1$-$C_6$ alkyl; and each n is independently chosen and is an integer from 0 to 5;

said method comprising:

a) treating a compound of formula (V, wherein $R^1$ is defined above, with an anion of a compound of formula (X), wherein $R^{13}$ is hydrogen, $C_1$-$C_6$ alkyl, $-Si(C_1$-$C_6$ alkyl)$_3$, or $-CH_2(C_6$-$C_{10}$ aryl), wherein said $C_6$-$C_{10}$ aryl group is optionally substituted with at least one substituent selected from halogen, $C_1$-$C_6$ alkyl, $-OH$, $-OCH_3$, and $-N(C_1$-$C_6$ alkyl)$_2$, to afford a compound of formula (IV);

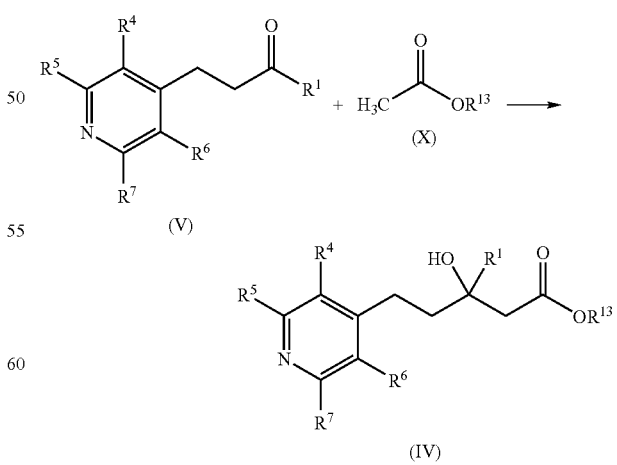

b) hydrolyzing the compound of formula (IV) to afford a compound of formula (IV) wherein $R^{13}$ is hydrogen;

c) treating the compound of formula (IV) with a combination of reagents to afford a compound of formula (III), wherein P$^1$ is hydrogen or a suitable protecting group, and R$^{14}$ is C$_1$-C$_6$ alkyl or —CH$_2$(C$_6$-C$_{10}$ aryl), wherein said C$_6$-C$_{10}$ aryl group is optionally substituted with at least one substituent selected from halogen, C$_1$-C$_6$ alkyl, —OH, —OCH$_3$, and —N(C$_1$-C$_6$ alkyl)$_2$;

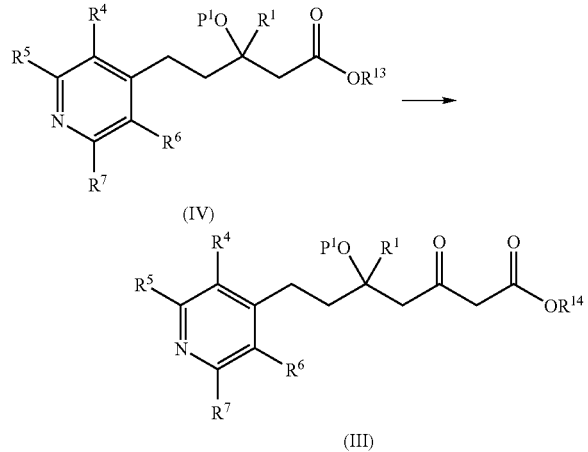

d) treating the compound of formula (III) with an acid or base to afford the compound of formula (II)

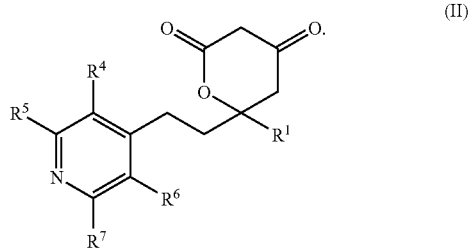

Further provided herein are such methods, wherein the compound of formula (II) is (IIa):

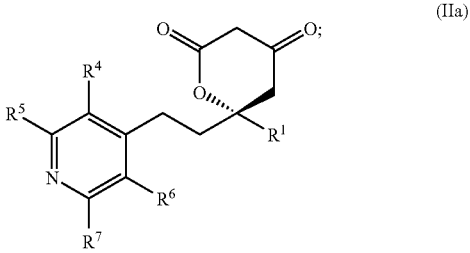

or wherein the compound of formula (II) is (IIb):

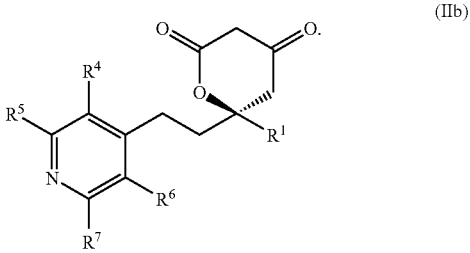

Also included herein are any of the above-described methods, wherein in the compound of formula (II):

R$^1$ is C$_3$-C$_6$ cycloalkyl;
R$^4$ is selected from hydrogen, C$_1$-C$_6$ alkyl, —(CR$^9$R$^{10}$)$_n$R$^{11}$, —CF$_3$, halogen, —OR$^{12a}$, —CN, and —NR$^{12a}$R$^{12b}$;
R$^5$ is selected from hydrogen, C$_1$-C$_6$ alkyl, —(CR$^9$R$^{10}$)$_n$R$^{11}$, —CF$_3$, halogen, —OR$^{12a}$, —CN, and —NR$^{12a}$R$^{12b}$;
R$^6$ is selected from hydrogen, C$_1$-C$_6$ alkyl, —(CR$^9$R$^{10}$)$_n$R$^{11}$, —CF$_3$, halogen, —OR$^{12a}$, —CN, and —NR$^{12a}$R$^{12b}$;
R$^7$ is selected from hydrogen, C$_1$-C$_6$ alkyl, —(CR$^9$R$^{10}$)$_n$R$^{11}$, —CF$_3$, halogen, —OR$^{12a}$, —CN, and —NR$^{12a}$R$^{12b}$;
each R$^9$ and R$^{10}$ is independently selected from hydrogen and C$_1$-C$_6$ alkyl, or R$^9$ and R$^{10}$, together with the carbon atom to which they are attached, form a C$_3$-C$_6$ cycloalkyl group;
each R$^{11}$ is independently selected from hydrogen, C$_1$-C$_6$ alkyl, halogen, —OR$^{12a}$, —CN, —CF$_3$, and —NR$^{12a}$R$^{12b}$;
each R$^{12a}$ and R$^{12b}$ is independently selected from hydrogen and C$_1$-C$_6$ alkyl; and
each n is independently chosen and is an integer from 0 to 5.

Furthermore, the present invention includes such above-described methods, wherein in the compound of formula (II):
R$^1$ is C$_3$-C$_6$ cycloalkyl;
R$^4$ is hydrogen;
R$^5$ is C$_1$-C$_6$ alkyl;
R$^6$ is hydrogen;
R$^7$ is C$_1$-C$_6$ alkyl;
each R$^9$ and R$^{10}$ is independently selected from hydrogen and C$_1$-C$_6$ alkyl, or R$^9$ and R$^{10}$, together with the carbon atom to which they are attached, form a C$_3$-C$_6$ cycloalkyl group;
R$^{11}$ is independently selected from hydrogen, C$_1$-C$_6$ alkyl, halogen, —OR$^{12a}$, —CN, —CF$_3$, and —NR$^9$R$^{10}$;
each R$^{12a}$ and R$^{12b}$ is independently selected from hydrogen and C$_1$-C$_6$ alkyl; and
each n is independently chosen and is an integer from 0 to 5.

Also included are any of the above-described methods, wherein in the compound of formula (II):
R$^1$ is cyclopentyl;
R$^4$ is hydrogen;
R$^5$ is —CH$_2$CH$_3$;
R$^6$ is hydrogen;
R$^7$ is —CH$_2$CH$_3$;
each R$^9$ and R$^{10}$ is independently selected from hydrogen and C$_1$-C$_6$ alkyl, or R$^9$ and R$^{10}$, together with the carbon atom to which they are attached, form a C$_3$-C$_6$ cycloalkyl group;
R$^{11}$ is independently selected from hydrogen, C$_1$-C$_6$ alkyl, halogen, —OR$^{12a}$, —CN, —CF$_3$, and —NR$^{12a}$R$^{12b}$; and
each R$^{12a}$ and R$^{12b}$ is independently selected from hydrogen and C$_1$-C$_6$ alkyl.

In still another aspect of the present invention are provided methods of preparing a stereoisomerically enriched compound of formula (Ia),

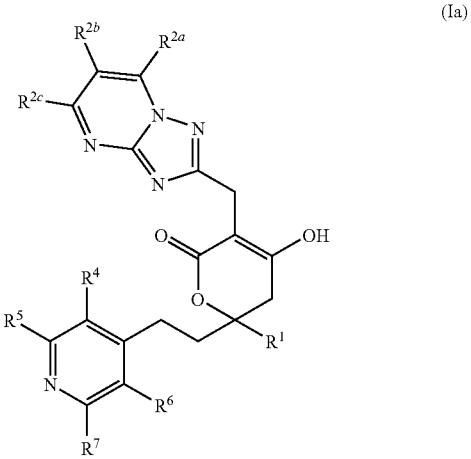

wherein:

$R^1$ is $C_1$-$C_6$ alkyl or $C_3$-$C_6$ cycloalkyl;

$R^{2a}$, $R^{2b}$, and $R^{2c}$ are each independently selected from hydrogen, halogen, $C_1$-$C_6$ alkyl, $C_3$-$C_6$ cycloalkyl, $-OR^{12a}$, $-CF_3$, $-CN$, and $-NR^{12a}R^{12b}$;

$R^4$ is selected from hydrogen, $C_1$-$C_6$ alkyl, $-(CR^9R^{10})_n R^{11}$, $-CF_3$, halogen, $-OR^{12a}$, $-CN$, and $-NR^{12a}R^{12b}$;

$R^5$ is selected from hydrogen, $C_1$-$C_6$ alkyl, $-(CR^9R^{10})_n R^{11}$, $-CF_3$, halogen, $-OR^{12a}$, $-CN$, and $-NR^{12a}R^{12b}$;

$R^6$ is selected from hydrogen, $C_1$-$C_6$ alkyl, $-(CR^9R^{10})_n R^{11}$, $-CF_3$, halogen, $-OR^{12a}$, $-CN$, and $-NR^{12a}R^{12b}$;

$R^7$ is selected from hydrogen, $C_1$-$C_6$ alkyl, $-(CR^9R^{10})_n R^{11}$, $-CF_3$, halogen, $-OR^{12a}$, $-CN$, and $-NR^{12a}R^{12b}$;

each $R^9$ and $R^{10}$ is independently selected from hydrogen and $C_1$-$C_6$ alkyl, or $R^9$ and $R^{10}$, together with the carbon atom to which they are attached, form a $C_3$-$C_6$ cycloalkyl group;

each $R^{11}$ is independently selected from hydrogen, $C_1$-$C_6$ alkyl, halogen, $-OR^{12a}$, $-CN$, $-CF_3$, and $-NR^9R^{10}$;

each $R^{12a}$ and $R^{12b}$ is independently selected from hydrogen and $C_1$-$C_6$ alkyl; and each n is independently chosen and is an integer from 0 to 5;

said method comprising:

a) treating a compound of formula (IV), wherein $R^1$, $R^4$, $R^5$, $R^6$, and $R^7$ are as hereinbefore defined and $P^1$ is hydrogen or a suitable protecting group, with a chiral, non-racemic base to afford a mixture of diastereomeric salts;

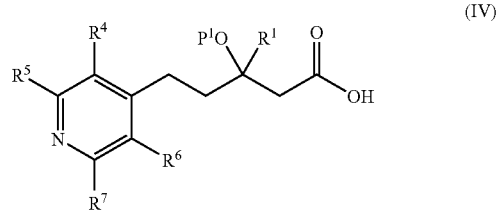

(IV)

b) separating said diastereomeric salts from each other;

c) converting said separated diastereomeric salts to a stereoisomerically enriched compound of formula (IV);

d) treating the stereoisomerically enriched compound of formula (IV), wherein $R^{13}$ is hydrogen, $C_1$-$C_6$ alkyl, $-Si(C_1$-$C_6$ alkyl)$_3$, or $-CH_2(C_6$-$C_{10}$ aryl), wherein said $C_6$-$C_{10}$ aryl group is optionally substituted with at least one substituent selected from halogen, $C_1$-$C_6$ alkyl, $-OH$, $-OCH_3$, and $-N(C_1$-$C_6$ alkyl)$_2$, with a combination of reagents to afford a stereoisomerically enriched compound of formula (III), wherein $R^{14}$ is hydrogen, $C_1$-$C_6$ alkyl, $-Si(C_1$-$C_6$ alkyl)$_3$, or $-CH_2(C_6$-$C_{10}$ aryl), wherein said $C_6$-$C_{10}$ aryl group is optionally substituted with at least one substituent selected from halogen, $C_1$-$C_6$ alkyl, $-OH$, $-OCH_3$, and $-N(C_1$-$C_6$ alkyl)$_2$;

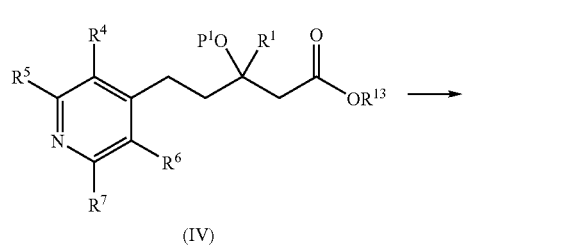

(IV)

-continued

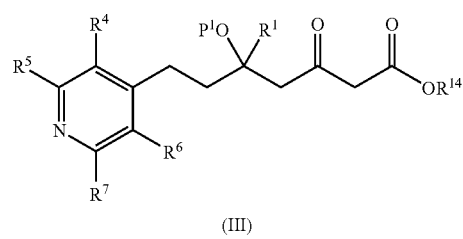

(III)

e) treating the stereoisomerically enriched compound of formula (III), wherein $P^1$ is hydrogen, with an acid or base to afford the stereoisomerically enriched compound of formula (II); and

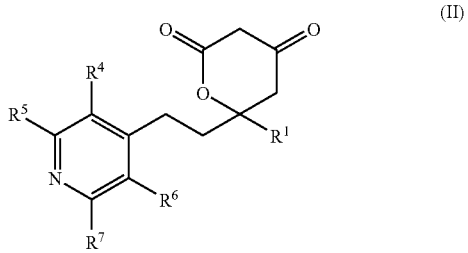

(II)

f) treating the stereoisomerically enriched compound of formula (II) with a compound of formula (IXa), to afford the stereoisomerically enriched compound of formula (Ia)

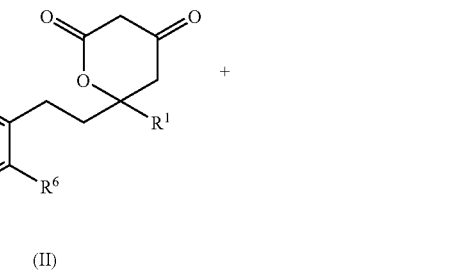

(II)

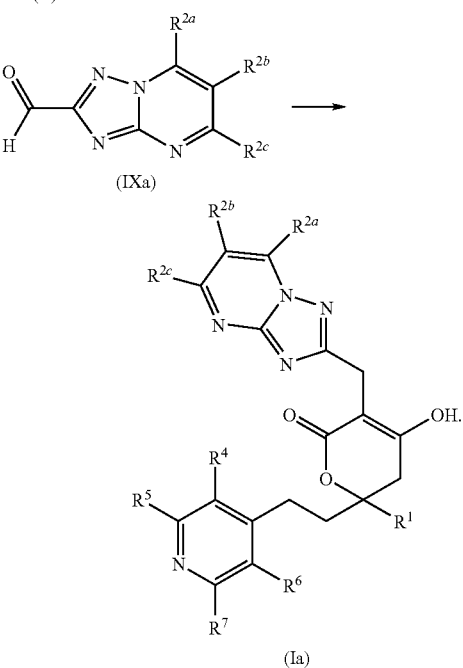

(Ia)

A further aspect of the present invention affords methods of preparing a stereoisomerically enriched compound of formula (II),

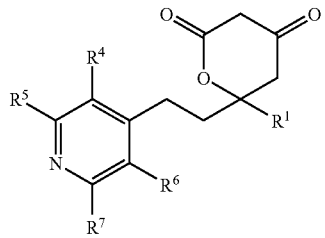

(II)

wherein:
R$^1$ is C$_1$-C$_6$ alkyl or C$_3$-C$_6$ cycloalkyl;
R$^4$ is selected from hydrogen, C$_1$-C$_6$ alkyl, —(CR$^9$R$^{10}$)$_n$R$^{11}$, —CF$_3$, halogen, —OR$^{12a}$, —CN, and —NR$^{12a}$R$^{12b}$;
R$^5$ is selected from hydrogen, C$_1$-C$_6$ alkyl, —(CR$^9$R$^{10}$)$_n$R$^{11}$, —CF$_3$, halogen, —OR$^{12a}$, —CN, and —NR$^{12a}$R$^{12b}$;
R$^6$ is selected from hydrogen, C$_1$-C$_6$ alkyl, —(CR$^9$R$^{10}$)$_n$R$^{11}$, —CF$_3$, halogen, —OR$^{12a}$, —CN, and —NR$^{12a}$R$^{12b}$;
R$^7$ is selected from hydrogen, C$_1$-C$_6$ alkyl, —(CR$^9$R$^{10}$)$_n$R$^{11}$, —CF$_3$, halogen, —OR$^{12a}$, —CN, and —NR$^{12a}$R$^{12b}$;
each R$^9$ and R$^{10}$ is independently selected from hydrogen and C$_1$-C$_6$ alkyl, or R$^9$ and R$^{10}$, together with the carbon atom to which they are attached, form a C$_3$-C$_6$ cycloalkyl group;
each R$^{11}$ is independently selected from hydrogen, C$_1$-C$_6$ alkyl, halogen, —OR$^{12a}$, —CN, —CF$_3$, and —NR$^{12a}$R$^{12b}$;
each R$^{12a}$ and R$^{12b}$ is independently selected from hydrogen and C$_1$-C$_6$ alkyl; and
each n is independently chosen and is an integer from 0 to 5;
said method comprising:
a) treating a compound of formula (IV), wherein R$^1$, R$^4$, R$^5$, R$^6$, and R$^7$ are as hereinbefore defined, and P$^1$ is hydrogen or a suitable protecting group, with a chiral, non-racemic base to afford a mixture of diastereomeric salts;

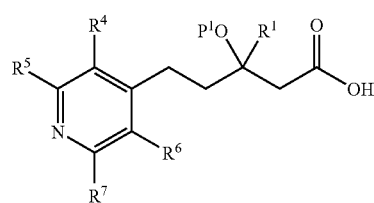

(IV)

b) separating said diastereomeric salts from each other;
c) converting said separated diastereomeric salts to a stereoisomerically enriched compound of formula (IV);
d) treating the stereoisomerically enriched compound of formula (IV), wherein P$^1$ is hydrogen or a suitable protecting group and R$^{13}$ is hydrogen, C$_1$-C$_6$ alkyl, —Si(C$_1$-C$_6$ alkyl)$_3$, or —CH$_2$(C$_6$-C$_{10}$ aryl), wherein said C$_6$-C$_{10}$ aryl group is optionally substituted with at least one substituent selected from halogen, C$_1$-C$_6$ alkyl, —OH, —OCH$_3$, and —N(C$_1$-C$_6$ alkyl)$_2$, with a combination of reagents to afford a stereoisomerically enriched compound of formula (III), wherein R$^{14}$ is hydrogen, C$_1$-C$_6$ alkyl, —Si(C$_1$-C$_6$ alkyl)$_3$, or —CH$_2$(C$_6$-C$_{10}$ aryl), wherein said C$_6$-C$_{10}$ aryl group is optionally substituted with at least one substituent selected from halogen, C$_1$-C$_6$ alkyl, —OH, —OCH$_3$, and —N(C$_1$-C$_6$ alkyl)$_2$; and

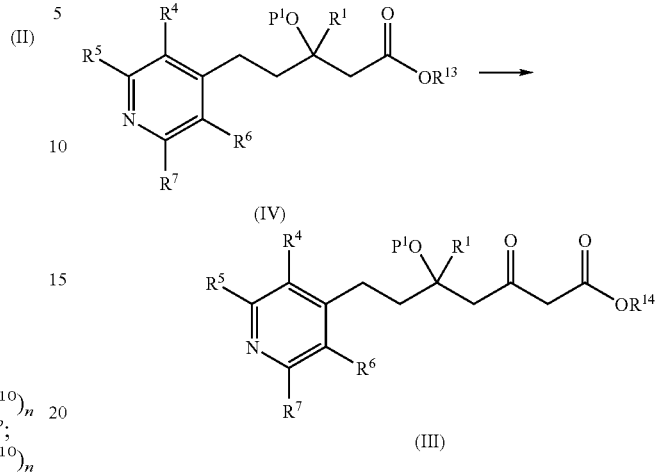

e) treating the stereoisomerically enriched compound of formula (III), wherein P$^1$ is hydrogen, with a base to afford the stereoisomerically enriched compound of formula (II)

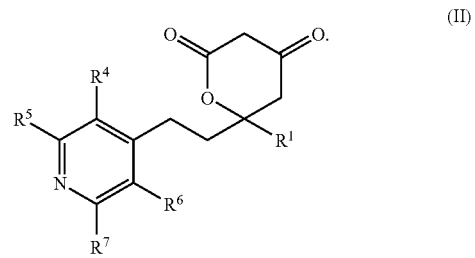

(II)

In a still further aspect of the present invention are provided methods of preparing a stereoisomerically enriched compound of formula (IV),

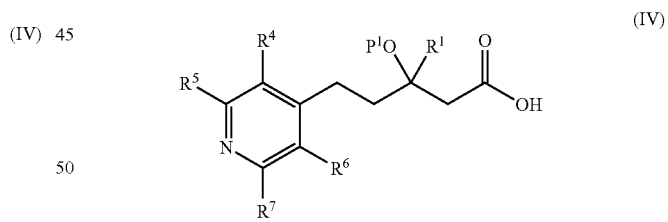

(IV)

wherein:
R$^1$ is C$_1$-C$_6$ alkyl or C$_3$-C$_6$ cycloalkyl;
R$^4$ is selected from hydrogen, C$_1$-C$_6$ alkyl, —(CR$^9$R$^{10}$)$_n$R$^{11}$, —CF$_3$, halogen, —OR$^{12a}$, —CN, and —NR$^{12a}$R$^{12b}$;
R$^5$ is selected from hydrogen, C$_1$-C$_6$ alkyl, —(CR$^9$R$^{10}$)$_n$R$^{11}$, —CF$_3$, halogen, —OR$^{12a}$, —CN, and —NR$^{12a}$R$^{12b}$;
R$^6$ is selected from hydrogen, C$_1$-C$_6$ alkyl —(CR$^9$R$^{10}$)$_n$R$^{11}$, —CF$_3$, halogen, —OR$^{12a}$, —CN, and —NR$^{12a}$R$^{12b}$;
R$^7$ is selected from hydrogen, C$_1$-C$_6$ alkyl, —(CR$^9$R$^{10}$)$_n$R$^{11}$, —CF$_3$, halogen, —OR$^{12a}$, —CN, and —NR$^{12a}$R$^{12b}$;
each R$^9$ and R$^{10}$ is independently selected from hydrogen and C$_1$-C$_6$ alkyl, or R$^9$ and R$^{10}$, together with the carbon atom to which they are attached, form of C$_3$-C$_6$ cycloalkyl group;

each $R^{11}$ is independently selected from hydrogen, $C_1$-$C_6$ alkyl, halogen, —$OR^{12a}$, —CN, —$CF_3$, and —$NR^{12a}R^{12b}$;

each $R^{12a}$ and $R^{12b}$ is independently selected from hydrogen and $C_1$-$C_6$ alkyl;

$P^1$ is hydrogen or a suitable protecting group; and each n is independently chosen and is an integer from 0 to 5;

said method comprising:

a) treating a compound of formula (IV) with a chiral, non-racemic base to form a mixture of diastereomeric salts;

b) separating said diastereomeric salts from each other; and c) converting said diastereomeric salts to a stereoisomerically enriched compound of formula (I).

Also included herein are any of the above-described methods, wherein said chiral, non-racemic base is a chiral, non-racemic amine; and wherein said chiral, non-racemic amine is selected from cis-1-amino-2-indanol, cinchonidine, 1-aminoindane, tert-leucinol, 2-amino-1,2-diphenylethanol, alpha-methylbenzylamine, and 2-amino-1-(4-nitrophenyl)-1,3-propanediol; and wherein said chiral, non-racemic amine is selected from (1R,2S)-(+)-cis-1-amino-2-indanol, (−)-cinchonidine, (R)-1-aminoindane, (S)-tert-leucinol, (1R,2S)-2-amino-1,2-diphenylethanol, (S)-alpha-methylbenzylamine, and (1R,2R)-(−)-2-amino-1-(4-nitrophenyl)-1,3-propanediol; and wherein said chiral, non-racemic amine is (1R,2R)-(−)-2-amino-1-(4-nitrophenyl)-1,3-propanediol.

In still another aspect of the present invention are provided compounds of formula (IV),

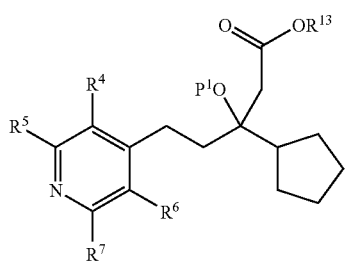

(IV)

wherein:

$R^4$ is selected from hydrogen, $C_1$-$C_6$ alkyl, —$(CR^9R^{10})_n R^{11}$, —$CF_3$, halogen, —$OR^{12a}$, —CN, and —$NR^{12a}R^{12b}$;

$R^5$ is selected from hydrogen, $C_1$-$C_6$ alkyl, —$(CR^9R^{10})_n R^{11}$, —$CF_3$, halogen, —$OR^{12a}$, —CN, and —$NR^{12a}R^{12b}$;

$R^6$ is selected from hydrogen, $C_1$-$C_6$ alkyl, —$(CR^9R^{10})_n R^{11}$, —$CF_3$, halogen, —$OR^{12a}$, —CN, and —$NR^{12a}R^{12b}$;

$R^7$ is selected from hydrogen, $C_1$-$C_6$ alkyl, —$(CR^9R^{10})_n R^{11}$, —$CF_3$, halogen, —$OR^{12a}$, —CN, and —$NR^{12a}R^{12b}$;

each $R^9$ and $R^{10}$ is independently selected from hydrogen and $C_1$-$C_6$ alkyl, or $R^9$ and $R^{10}$, together with the carbon atom to which they are attached, form a $C_3$-$C_6$ cycloalkyl group;

each $R^{11}$ is independently selected from hydrogen, $C_1$-$C_6$ alkyl, halogen, —$OR^{12a}$, —CN, —$CF_3$, and —$NR^{12a}R^{12b}$;

each $R^{12a}$ and $R^{12b}$ is independently selected from hydrogen and $C_1$-$C_6$ alkyl;

$R^{13}$ is hydrogen, $C_1$-$C_6$ alkyl, —Si($C_1$-$C_6$ alkyl)$_3$, or —$CH_2(C_6$-$C_{10}$ aryl), wherein said $C_6$-$C_{10}$ aryl group is optionally substituted with at least one substituent selected from halogen, $C_1$-$C_6$ alkyl, —OH, —$OCH_3$, and —N($C_1$-$C_6$ alkyl)$_2$ $P^1$ is hydrogen or a suitable protecting group; and each n is independently chosen and is an integer from 0 to 5.

Further included are such compounds, wherein $P^1$ is —Si($C_1$-$C_6$ alkyl)$_3$ or —$CH_2(C_6$-$C_{10}$ aryl), wherein said $C_6$-$C_{10}$ aryl group is optionally substituted with at least one substituent selected from halogen, $C_1$-$C_6$ alkyl, —OH, —$OCH_3$, and —N($C_1$-$C_6$ alkyl)$_2$.

Also included are such compounds, wherein:

$R^4$ is selected from hydrogen, $C_1$-$C_6$ alkyl, —$(CR^9R^{10})_n R^{11}$, —$CF_3$, halogen, —$OR^{12a}$, —CN, and —$NR^{12a}R^{12b}$;

$R^5$ is selected from hydrogen, $C_1$-$C_6$ alkyl, —$(CR^9R^{10})_n R^{11}$, —$CF_3$, halogen, —$OR^{12a}$, —CN, and —$NR^{12a}R^{12b}$;

$R^6$ is selected from hydrogen, $C_1$-$C_6$ alkyl —$(CR^9R^{10})_n R^{11}$, —$CF_3$, halogen, —$OR^{12a}$, —CN, and —$NR^{12a}R^{12b}$;

$R^7$ is selected from hydrogen, $C_1$-$C_6$ alkyl, —$(CR^9R^{10})_n R^{11}$, —$CF_3$, halogen, —$OR^{12a}$, —CN, and —$NR^{12a}R^{12b}$;

each $R^9$ and $R^{10}$ is independently selected from hydrogen and $C_1$-$C_6$ alkyl, or $R^9$ and $R^{10}$, together with the carbon atom to which they are attached, form a $C_3$-$C_6$ cycloalkyl group;

$R^{11}$ is —CN;

each $R^{12a}$ and $R^{12b}$ is independently selected from hydrogen and $C_1$-$C_6$ alkyl;

$R^{13}$ is hydrogen, $C_1$-$C_6$ alkyl, —Si($C_1$-$C_6$ alkyl)$_3$, or —$CH_2(C_6$-$C_{10}$ aryl), wherein said $C_6$-$C_{10}$ aryl group is optionally substituted with at least one substituent selected from halogen, $C_1$-$C_6$ alkyl, —OH, —$OCH_3$, and —N($C_1$-$C_6$ alkyl)$_2$;

$P^1$ is hydrogen or a suitable protecting group; and each n is independently chosen and is an integer from 0 to 5.

In still another aspect are such compounds, wherein:

$R^4$ is hydrogen;

$R^5$ is $C_1$-$C_6$ alkyl;

$R^6$ is hydrogen; and $R^7$ is $C_1$-$C_6$ alkyl;

Further provided herein are such compounds, wherein:

$R^4$ is hydrogen;

$R^5$ is —$CH_2CH_3$;

$R^6$ is hydrogen;

$R^7$ is —$CH_2CH_3$; and $R^{13}$ is hydrogen or $C_1$-$C_6$ alkyl.

In still a further aspect of the present invention are provided compounds of the formula:

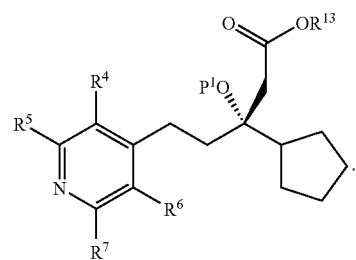

Also included herein are such compounds, wherein $P^1$ is —Si($C_1$-$C_6$ alkyl)$_3$ or —$CH_2(C_6$-$C_{10}$ aryl), wherein said $C_6$-$C_{10}$ aryl group is optionally substituted with at least one substituent selected from halogen, $C_1$-$C_6$ alkyl, —OH, —$OCH_3$, and —N($C_1$-$C_6$ alkyl)$_2$.

In still a further aspect of the present invention are compounds of the formula:

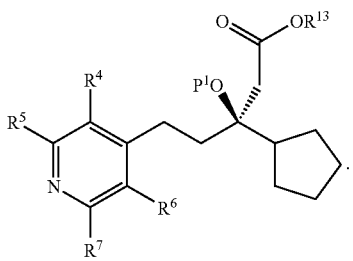

Also included herein are such compounds, wherein $P^1$ is —Si($C_1$-$C_6$ alkyl)$_3$ or —CH$_2$($C_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$.

In a further aspect of the present invention are afforded compounds of formula:

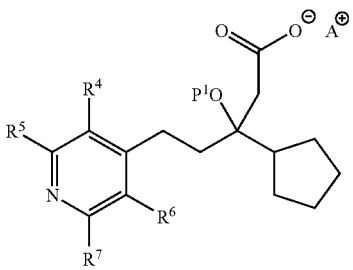

wherein:

$P^1$ is hydrogen or a suitable protecting group;

$R^4$ is selected from hydrogen, $C_1$-$C_6$ alkyl, —(CR$^9$R$^{10}$)$_n$R$^{11}$, —CF$_3$, halogen, —OR$^{12a}$, —CN, and —NR$^{12a}$R$^{12b}$;

$R^5$ is selected from hydrogen, $C_1$-$C_6$ alkyl, —(CR$^9$R$^{10}$)$_n$R$^{11}$, —CF$_3$, halogen, —OR$^{12a}$, —CN, and —NR$^{12a}$R$^{12b}$;

$R^6$ is selected from hydrogen, $C_1$-$C_6$ alkyl, —(CR$^9$R$^{10}$)$_n$R$^{11}$, —CF$_3$, halogen, —OR$^{12a}$, —CN, and —NR$^{12a}$R$^{12b}$;

$R^7$ is selected from hydrogen, $C_1$-$C_6$ alkyl, —(CR$^9$R$^{10}$)$_n$R$^{11}$, —CF$_3$, halogen, —OR$^{12a}$, —CN, and —NR$^{12a}$R$^{12b}$;

each $R^9$ and $R^{10}$ is independently selected from hydrogen and $C_1$-$C_6$ alkyl (or $R^9$ and $R^{10}$, together with the carbon atom to which they are attached, form a $C_3$-$C_6$ cycloalkyl group;

$R^{11}$ is —CN;

each $R^{12a}$ and $R^{12b}$ is independently selected from hydrogen and $C_1$-$C_6$ alkyl;

each n is independently chosen and is an integer from 0 to 5; and $A^+$ is a suitable counter-ion.

Also included herein are such compounds, wherein $P^1$ is —Si($C_1$-$C_6$ alkyl)$_3$ or —CH$_2$($C_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$.

Also included herein are such compounds, wherein:
$P^1$ is hydrogen;
$R^4$ is hydrogen;
$R^5$ is $C_1$-$C_6$ alkyl;
$R^6$ is hydrogen;
$R^7$ is $C_1$-$C_6$ alkyl; and
$A^+$ is a suitable counter-ion.

Further included are any of the above-described compounds, wherein said suitable counter-ion is derived from an amine base; and wherein said amine base is dicyclohexylamine; or wherein said amine base is a chiral, non-racemic amine base. Further included herein are such compounds, wherein said chiral, non-racemic amine is selected from one enantiomer of cis-1-amino-2-indanol, cinchonidine, 1-aminoindane, tert-leucinol, 2-amino-1,2-diphenylethanol, alpha-methylbenzylamine, and 2-amino-1-(4-nitrophenyl)-1,3-propanediol; or wherein said chiral, non-racemic amine base is selected from (1R,2S)-(+)-cis-1-amino-2-indanol, (−)-cinchonidine, (R)-1-aminoindane, (S)-tert-leucinol, (1R,2S)-2-amino-1,2-diphenylethanol, alpha-methylbenzylamine, and (1R,2R)-(−)-2-amino-1-(4-nitrophenyl)-1,3-propanediol; or wherein said chiral, non-racemic amine base is (1R,2R)-(−)-2-amino-1-(4-nitrophenyl)-1,3-propanediol.

In still another aspect of the present invention are provided compounds of formula (IIIa):

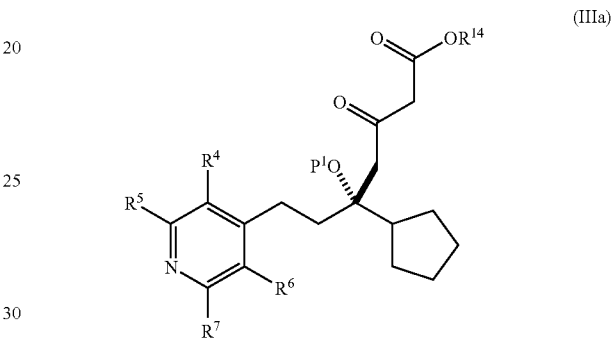

wherein:

$R^4$ is selected from hydrogen, $C_1$-$C_6$ alkyl, —(CR$^9$R$^{10}$)$_n$R$^{11}$, —CF$_3$, halogen, —OR$^{12a}$, —CN, and —NR$^{12a}$R$^{12b}$;

$R^5$ is selected from hydrogen, $C_1$-$C_6$ alkyl, —(CR$^9$R$^{10}$)$_n$R$^{11}$, —CF$_3$, halogen, —OR$^{12a}$, —CN, and —NR$^{12a}$R$^{12b}$;

$R^6$ is selected from hydrogen, $C_1$-$C_6$ alkyl, —(CR$^9$R$^{10}$)$_n$R$^{11}$, —CF$_3$, halogen, —OR$^{12a}$, —CN, and —NR$^{12a}$R$^{12b}$;

$R^7$ is selected from hydrogen, $C_1$-$C_6$ alkyl, —(CR$^9$R$^{10}$)$_n$R$^{11}$, —CF$_3$, halogen, —OR$^{12a}$, —CN, and —NR$^{12a}$R$^{12b}$;

each $R^9$ and $R^{10}$ is independently selected from hydrogen and $C_1$-$C_6$ alkyl, or $R^9$ and $R^{10}$, together with the carbon atom to which they are attached, form a $C_3$-$C_6$ cycloalkyl group;

each $R^{11}$ is independently selected from hydrogen, $C_1$-$C_6$ alkyl, halogen, —OR$^{12a}$, —CN, —CF$_3$, and —NR$^9$R$^{10}$;

each $R^{12a}$ and $R^{12b}$; is independently selected from hydrogen and $C_1$-$C_6$ alkyl;

$P^1$ is hydrogen or a suitable protecting group;

$R^{14}$ is $C_1$-$C_6$ alkyl or —CH$_2$($C_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$; and each n is independently chosen and is an integer from 0 to 5.

Also included herein are such compounds, wherein $P^1$ is —Si($C_1$-$C_6$ alkyl)$_3$ or —CH$_2$($C_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_8$ alkyl)$_2$.

Also included herein are such compounds, wherein:
$R^4$ is hydrogen;
$R^5$ is $C_1$-$C_6$ alkyl;
$R^6$ is hydrogen;
$R^7$ is $C_1$-$C_6$ alkyl;
$P^1$ is hydrogen; and
$R^{14}$ is hydrogen or $C_1$-$C_6$ alkyl.

Also included herein are such compounds, wherein:
$R^4$ is hydrogen;
$R^5$ is —CH$_2$CH$_3$;
$R^6$ is hydrogen;
$R^7$ is —CH$_2$CH$_3$;
$P^1$ is hydrogen; and
$R^{14}$ is hydrogen or C$_1$-C$_6$ alkyl.

In still another aspect of the present invention are provided compounds of formula (IIIb):

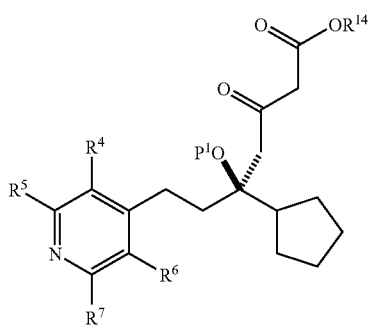

(IIIb)

wherein:
$R^4$ is selected from hydrogen, C$_1$-C$_6$ alkyl, —(CR$^9$R$^{10}$)$_n$R$^{11}$, —CF$_3$, halogen, —OR$^{12a}$, —CN, and —NR$^{12a}$R$^{12b}$;
$R^5$ is selected from hydrogen, C$_1$-C$_6$ alkyl, —(CR$^9$R$^{10}$)$_n$R$^{11}$, —CF$_3$, halogen, —OR$^{12a}$, —CN, and —NR$^{12a}$R$^{12b}$;
$R^6$ is selected from hydrogen, C$_1$-C$_6$ alkyl, —(CR$^9$R$^{10}$)$_n$R$^{11}$, —CF$_3$, halogen, —OR$^{12a}$, —CN, and —NR$^{12a}$R$^{12b}$;
$R^7$ is selected from hydrogen, C$_1$-C$_6$ alkyl, —(CR$^9$R$^{10}$)$_n$R$^{11}$, —CF$_3$, halogen, —OR$^{12a}$, —CN, and —NR$^{12a}$R$^{12b}$;
each $R^9$ and $R^{10}$ is independently selected from hydrogen and C$_1$-C$_6$ alkyl, or $R^9$ and $R^{10}$, together with the carbon atom to which they are attached, form a C$_3$-C$_6$ cycloalkyl group;
each $R^{11}$ is independently selected from hydrogen, C$_1$-C$_6$ alkyl, halogen, —OR$^{12a}$, —CN, —CF$_3$, and —NR$^9$R$^{10}$;
each $R^{12a}$ and $R^{12b}$ is independently selected from hydrogen and C$_1$-C$_6$ alkyl;
$P^1$ is hydrogen or a suitable protecting group;
$R^{14}$ is C$_1$-C$_6$ alkyl or —CH$_2$(C$_6$-C$_{10}$ aryl), wherein said C$_6$-C$_{10}$ aryl group is optionally substituted with at least one substituent selected from halogen, C$_1$-C$_6$ alkyl, —OH, —OCH$_3$, and —N(C$_1$-C$_6$ alkyl)$_2$; and
each n is independently chosen and is an integer from 0 to 5.

Also included herein are such compounds, wherein $P^1$ is —Si(C$_1$-C$_6$ alkyl)$_3$ or —CH$_2$(C$_6$-C$_{10}$ aryl), wherein said C$_6$-C$_{10}$ aryl group is optionally substituted with at least one substituent selected from halogen, C$_1$-C$_6$ alkyl, —OH, —OCH$_3$, and —N(C$_1$-C$_6$ alkyl)$_2$.

Also included herein are such compounds, wherein:
$R^4$ is hydrogen;
$R^5$ is C$_1$-C$_6$ alkyl;
$R^6$ is hydrogen;
$R^7$ is C$_1$-C$_6$ alkyl;
$P^1$ is hydrogen; and
$R^{14}$ is hydrogen or C$_1$-C$_6$ alkyl.

Also included herein are such compounds, wherein:
$R^4$ is hydrogen;
$R^5$ is —CH$_2$CH$_3$;
$R^6$ is hydrogen;
$R^7$ is —CH$_2$CH$_3$;
$P^1$ is hydrogen; and
$R^{14}$ is hydrogen or C$_1$-C$_6$ alkyl.

In yet another aspect of the present invention are afforded compounds of formula:

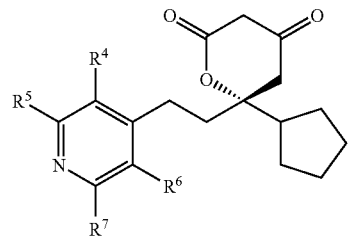

wherein:
$R^4$ is selected from hydrogen, C$_1$-C$_6$ alkyl, —(CR$^9$R$^{10}$)$_n$R$^{11}$, —CF$_3$, halogen, —OR$^{12a}$, —CN, and —NR$^{12a}$R$^{12b}$;
$R^5$ is selected from hydrogen, C$_1$-C$_6$ alkyl, —(CR$^9$R$^{10}$)$_n$R$^{11}$, —CF$_3$, halogen, —OR$^{12a}$, —CN, and —NR$^{12a}$R$^{12b}$;
$R^6$ is selected from hydrogen, C$_1$-C$_6$ alkyl, —(CR$^9$R$^{10}$)$_n$R$^{11}$, —CF$_3$, halogen, —OR$^{12a}$, —CN, and —NR$^{12a}$R$^{12b}$;
$R^7$ is selected from hydrogen, C$_1$-C$_6$ alkyl, —(CR$^9$R$^{10}$)$_n$R$^{11}$, —CF$_3$, halogen, —OR$^{12a}$, —CN, and —NR$^{12a}$R$^{12b}$;
each $R^9$ and $R^{10}$ is independently selected from hydrogen and C$_1$-C$_6$ alkyl, or $R^9$ and $R^{10}$, together with the carbon atom to which they are attached, form a C$_3$-C$_6$ cycloalkyl group;
each $R^{11}$ is independently selected from hydrogen, C$_1$-C$_6$ alkyl, halogen, —OR$^{12a}$, —CN, —CF$_3$, and —NR$^9$R$^{10}$;
each $R^{12a}$ and $R^{12b}$ is independently selected from hydrogen and C$_1$-C$_6$ alkyl;
$R^{14}$ is hydrogen or C$_1$-C$_6$ alkyl; and
each n is independently chosen and is an integer from 0 to 5.

Also included herein are such compounds, wherein:
$R^4$ is hydrogen;
$R^5$ is C$_1$-C$_6$ alkyl;
$R^6$ is hydrogen; and
$R^7$ is C$_1$-C$_6$ alkyl.

Also included herein are such compounds, wherein:
$R^4$ is hydrogen;
$R^5$ is —CH$_2$CH$_3$;
$R^6$ is hydrogen; and
$R^7$ is —CH$_2$CH$_3$.

In still a further aspect of the present invention are provided compounds of formula:

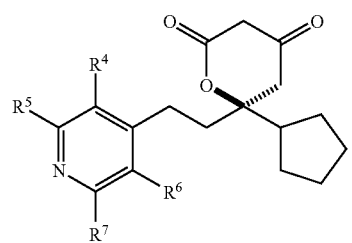

wherein:
$R^4$ is selected from hydrogen, C$_1$-C$_6$ alkyl, —(CR$^9$R$^{10}$)$_n$R$^{11}$, —CF$_3$, halogen, —OR$^{12a}$, —CN, and —NR$^{12a}$R$^{12b}$;
$R^5$ is selected from hydrogen, C$_1$-C$_6$ alkyl, —(CR$^9$R$^{10}$)$_n$R$^{11}$, —CF$_3$, halogen, —OR$^{12a}$, —CN, and —NR$^{12a}$R$^{12b}$;
$R^6$ is selected from hydrogen, C$_1$-C$_6$ alkyl, —(CR$^9$R$^{10}$)$_n$R$^{11}$, —CF$_3$, halogen, —OR$^{12a}$, —CN, and —NR$^{12a}$R$^{12b}$;

$R^7$ is selected from hydrogen, $C_1$-$C_6$ alkyl, —$(CR^9R^{10})_n$$R^{11}$, —$CF_3$, halogen, —$OR^{12a}$, —CN, and —$NR^{12a}R^{12b}$;

each $R^9$ and $R^{10}$ is independently selected from hydrogen and $C_1$-$C_6$ alkyl, or $R^9$ and $R^{10}$, together with the carbon atom to which they are attached, form a $C_3$-$C_6$ cycloalkyl group;

each $R^{11}$ is independently selected from hydrogen, $C_1$-$C_6$ alkyl, halogen, —$OR^{12a}$, —CN, —$CF_3$, and —$NR^9R^{10}$;

each $R^{12a}$ and $R^{12b}$ is independently selected from hydrogen and $C_1$-$C_6$ alkyl;

$R^{14}$ is hydrogen or $C_1$-$C_6$ alkyl; and each n is independently chosen and is an integer from 0 to 5.

Also included herein are such compounds, wherein:
$R^4$ is hydrogen;
$R^5$ is $C_1$-$C_6$ alkyl;
$R^6$ is hydrogen; and
$R^7$ is $C_1$-$C_6$ alkyl.

Also included herein are such compounds, wherein:
$R^4$ is hydrogen;
$R^5$ is —$CH_2CH_3$;
$R^6$ is hydrogen; and
$R^7$ is —$CH_2CH_3$.

In still a further aspect of the present invention are provided methods of preparing a compound of formula (Ie):

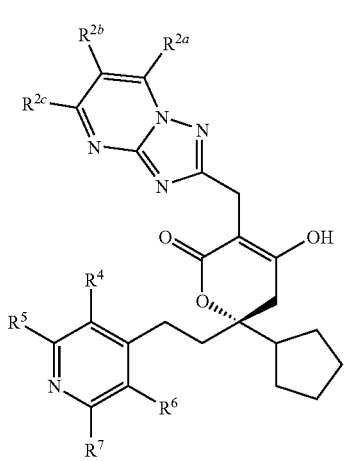

(Ie)

wherein:
$R^{2a}$, $R^{2b}$, and $R^{2c}$ are each independently selected from hydrogen, halogen, $C_1$-$C_6$ alkyl, $C_3$-$C_6$ cycloalkyl, —$OR^{12a}$, —$CF_3$, —CN, and —$NR^{12a}R^{12b}$;

$R^4$ is selected from hydrogen, $C_1$-$C_6$ alkyl, —$(CR^9R^{10})_n$$R^{11}$, —$CF_3$, halogen, —$OR^{12a}$, —CN, and —$NR^{12a}R^{12b}$;

$R^5$ is selected from hydrogen, $C_1$-$C_6$ alkyl, —$(CR^9R^{10})_n$$R^{11}$, —$CF_3$, halogen, —$OR^{12a}$, —CN, and —$NR^{12a}R^{12b}$;

$R^6$ is selected from hydrogen, $C_1$-$C_6$ alkyl, —$(CR^9R^{10})_n$$R^{11}$, —$CF_3$, halogen, —$OR^{12a}$, —CN, and —$NR^{12a}R^{12b}$;

$R^7$ is selected from hydrogen, $C_1$-$C_6$ alkyl, —$(CR^9R^{10})_n$$R^{11}$, —$CF_3$, halogen, —$OR^{12a}$, —CN, and —$NR^{12a}R^{12b}$;

each $R^9$ and $R^{10}$ is independently selected from hydrogen and $C_1$-$C_6$ alkyl, or $R^9$ and $R^{10}$, together with the carbon atom to which they are attached, form a $C_3$-$C_6$ cycloalkyl group;

each $R^{11}$ is independently selected from hydrogen, $C_1$-$C_6$ alkyl, halogen, —$OR^{12a}$, —CN, —$CF_3$, and —$NR^{12a}R^{12b}$;

each $R^{12a}$ and $R^{12b}$; is independently selected from hydrogen and $C_1$-$C_6$ alkyl; and each n is independently chosen and is an integer from 0 to 5; said method comprising treating a compound of formula (IIa), wherein $R^4$, $R^5$, $R^6$, and $R^7$ are as hereinbefore defined, with a compound of formula (IXa)

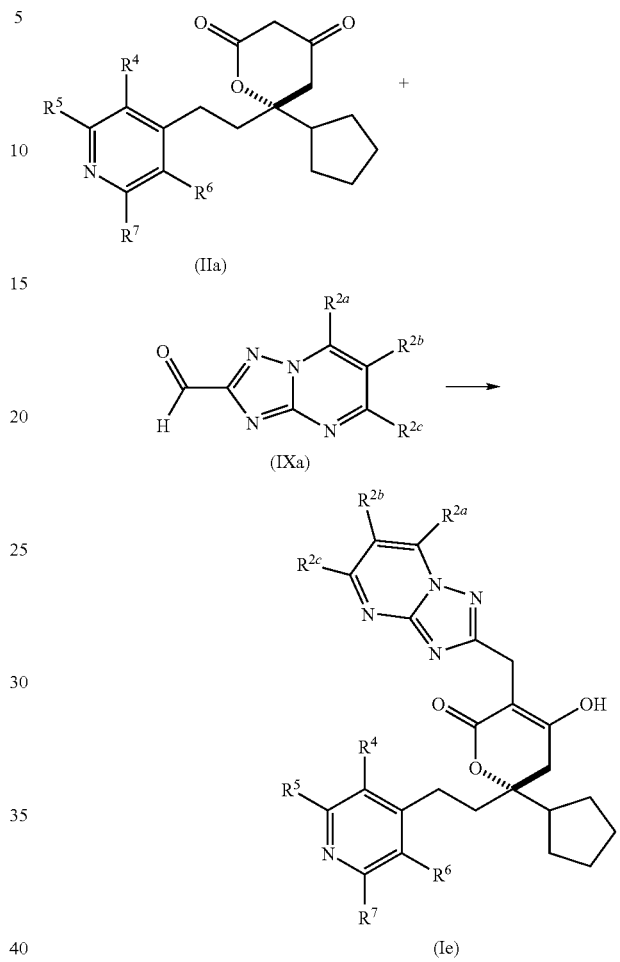

to afford the compound of formula (Ie).

Also included herein are such methods, wherein:
$R^{2a}$, $R^{2b}$, and $R^{2c}$ are each independently selected from hydrogen, halogen, $C_1$-$C_6$ alkyl, $C_3$-$C_6$ cycloalkyl, —$OR^{12a}$, —$CF_3$, —CN, and —$NR^{12a}R^{12}$;

$R^4$ is hydrogen;
$R^5$ is $C_1$-$C_6$ alkyl;
$R^6$ is hydrogen;
$R^7$ is $C_1$-$C_6$ alkyl; and each $R^{12a}$ and $R^{12b}$ is independently selected from hydrogen and $C_1$-$C_6$ alkyl.

Also included herein are such methods, wherein:
$R^{2a}$, $R^{2b}$, and $R^{2c}$ are each independently selected from hydrogen, halogen, and $C_1$-$C_6$ alkyl;
$R^4$ is hydrogen;
$R^5$ is —$CH_2CH_3$;
$R^6$ is hydrogen; and
$R^7$ is —$CH_2CH_3$.

In yet another aspect of the present invention are afforded methods of preparing a compound of formula (If):

(If)

[Chemical structure showing formula (If)]

wherein:

$R^2$, $R^{2b}$, and $R^{2c}$ are each independently selected from hydrogen, halogen, $C_1$-$C_6$ alkyl, $C_3$-$C_6$ cycloalkyl, —$OR^{12a}$, —$CF_3$, —CN, and —$NR^{12a}R^{12b}$;

$R^4$ is selected from hydrogen, $C_1$-$C_6$ alkyl, —$(CR^9R^{10})_n$ $R^{11}$, —$CF_3$, halogen, —$OR^{12a}$, —CN, and —$NR^{12a}R^{12b}$;

$R^5$ is selected from hydrogen, $C_1$-$C_6$ alkyl, —$(CR^9R^{10})_n$ $R^{11}$, —$CF_3$, halogen, —$OR^{12a}$, —CN, and —$NR^{12a}R^{12b}$;

$R^6$ is selected from hydrogen, $C_1$-$C_6$ alkyl, —$(CR^9R^{10})_n$ $R^{11}$, —$CF_3$, halogen, —$OR^{12a}$, —CN, and —$NR^{12a}R^{12b}$;

$R^7$ is selected from hydrogen, $C_1$-$C_6$ alkyl, —$(CR^9R^{10})_n$ $R^{11}$, —$CF_3$, halogen, —$OR^{12a}$, —CN, and —$NR^{12a}R^{12b}$;

each $R^9$ and $R^{10}$ is independently selected from hydrogen and $C_1$-$C_6$ alkyl, or $R^9$ and $R^{10}$, together with the carbon atom to which they are attached, form a $C_3$-$C_6$ cycloalkyl group;

each $R^{11}$ is independently selected from hydrogen, $C_1$-$C_6$ alkyl, halogen, —$OR^{12a}$, —CN, —$CF_3$, and —$NR^{12a}R^{12b}$;

each $R^{12a}$ and $R^{12b}$ is independently selected from hydrogen and $C_1$-$C_6$ alkyl; and each n is independently chosen and is an integer from 0 to 5;

said method comprising treating a compound of formula (IIa), wherein $R^4$, $R^5$, $R^6$, and $R^7$ are as hereinbefore defined, with a compound of formula (IXa)

[Chemical structure (IIa)]

+

[Chemical structure (IXa)] →

-continued

[Chemical structure showing formula (If)]

(If)

to afford the compound of formula (If).

Also included herein are such methods, wherein:

$R^{2a}$, $R^{2b}$, and $R^{2c}$ are each independently selected from hydrogen, halogen, $C_1$-$C_6$ alkyl, $C_3$-$C_6$ cycloalkyl, —$OR^{12a}$, —$CF_3$, —CN, and —$NR^{12a}R^{12b}$;

$R^4$ is hydrogen;

$R^5$ is $C_1$-$C_6$ alkyl;

$R^6$ is hydrogen;

$R^7$ is $C_1$-$C_6$ alkyl; and each $R^{12a}$ and $R^{12b}$ is independently selected from hydrogen and $C_1$-$C_6$ alkyl.

Also included herein are such methods, wherein:

$R^{2a}$, $R^{2b}$, and $R^{2c}$ are each independently selected from hydrogen, halogen, and $C_1$-$C_6$ alkyl;

$R^4$ is hydrogen;

$R^5$ is —$CH_2CH_3$;

$R^6$ is hydrogen; and $R^7$ is —$CH_2CH_3$.

Further provided herein is a crystalline form of (R)-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one. Said crystalline form exhibits any one of a characteristic peak in the powder x-ray diffraction pattern, expressed in degrees two-theta, selected from of about 7.1; or of about 12.1; or of about 16.1; or of about 17.5; or of about 23.5.

In still another aspect is provided a crystalline form of (R)-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one exhibiting characteristic peaks in the powder x-ray diffraction pattern, expressed in degrees two-theta, selected from of about 7.1 and of about 12.1; or of about 7.1 and of about 16.1; or of about 7.1 and of about 17.5; or of about 7.1 and of about 23.5; or of about 12.1 and of about 16.1; or of about 12.1 and of about 17.5; or of about 12.1 and of about 23.5; or of about 16.1 and of about 17.5; or of about 16.1 and of about 23.5; or of about 17.5 and of about 23.5

In still another aspect is provided a crystalline form of (R)-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one exhibiting characteristic peaks in the powder x-ray diffraction pattern, expressed in degrees two-theta, selected from of about 7.1, of about 12.1 and of about 16.1; or of about 7.1, of about 12.1, and of about 17.5; or of about 7.1, of about 12.1, and of about 23.5; or of about 12.1, of about 16.1, and of about 17.5; or of about 12.1, of about 16.1, and of about 23.5; or of about 16.1, of about 17.5, and of about 23.5; or of about 7.1 of about 17.5, and of about 23.5; or of about 7.1, of about 12.1, and of about 23.5; or of about 7.1, of about 16.1, and of about 23.5.

In still another aspect is provided a crystalline form of (R)-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one exhibiting characteristic peaks in the powder x-ray diffraction pattern, expressed in degrees two-theta, of about 7.1, of about 12.1, of about 16.1, of about 17.5, and of about 23.5.

Also provided herein is a crystalline form of (R)-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one exhibiting characteristic peaks in the solid state NMR spectrum, expressed in ppm, at about 154.6, about 153.0, about 151.2, about 146.4, about 146.0, about 121.6, about 120.4, about 119.7, about 118.8, about 110.2, about 100.7, and about 100.3.

In another embodiment is provided a crystalline form of (R)-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one exhibiting a melting temperature in the range of between about 162° C. and about 165° C.

Also provided herein is a crystalline form of (R)-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one exhibiting any combination of any number of characteristic peaks in the powder x-ray diffraction pattern described above and any number of any characteristic peaks in the solid state NMR spectrum described above. For example, in one embodiment is provided a crystalline form of (R)-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one exhibiting a characteristic peak in the powder x-ray diffraction pattern, expressed in degrees two-theta, at about 7.1, and a peak in the solid state NMR spectrum, expressed in ppm, at about 154.6.

In still another embodiment is provided a crystalline form of (R)-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one exhibiting a characteristic peak in the powder x-ray diffraction pattern, expressed in degrees two-theta, at about 7.1, a peak in the solid state NMR spectrum, expressed in ppm, at about 154.6, and a melting temperature in the range of between about 162° C. and about 165° C.

The invention also relates to a method for the treatment of Hepatitis C virus (HCV) in an HCV-infected mammal, such as a human, comprising administering to said mammal an amount of a crystalline form of (R)-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one, or a pharmaceutically acceptable salt thereof, that is effective in treating HCV. In other embodiments are provided such methods, wherein said crystalline form of (R)-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one exhibits any one of a characteristic peak in the powder x-ray diffraction pattern, expressed in degrees two-theta, selected from of about 7.1; or of about 12.1; or of about 16.1; or of about 17.5; or of about 23.5.

In a further aspect of the present invention are provided methods for the treatment of a mammal, such as a human, suffering from infection with Hepatitis C virus, comprising administering to said mammal a Hepatitis C virus-inhibiting amount of a crystalline form of (R)-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one, or a pharmaceutically acceptable salt thereof. In other embodiments are provided such methods, wherein said crystalline form of (R)-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one exhibits any one of a characteristic peak in the powder x-ray diffraction pattern, expressed in degrees two-theta, selected from of about 7.1; or of about 12.1; or of about 16.1; or of about 17.5; or of about 23.5.

Also provided herein are pharmaceutical compositions comprising a crystalline form of (R)-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one, or a pharmaceutically acceptable salt thereof, and a pharmaceutically acceptable carrier. In other embodiments are provided such pharmaceutical compositions, wherein said crystalline form of (R)-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one exhibits any one of a characteristic peak in the powder x-ray diffraction pattern, expressed in degrees two-theta, selected from of about 7.1; or of about 12.1; or of about 16.1; or of about 17.5; or of about 23.5.

Further provided herein are pharmaceutical compositions for the treatment of Hepatitis C virus (HCV) in a mammal, such as a human, comprising an amount of a crystalline form of (R)-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one, or a pharmaceutically acceptable salt thereof, that is effective in treating Hepatitis C virus in an infected mammal, and a pharmaceutically acceptable carrier. In other embodiments are provided such pharmaceutical compositions, wherein said crystalline form of (R)-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one exhibits any one of a characteristic peak in the powder x-ray diffraction pattern, expressed in degrees two-theta, selected from of about 7.1; or of about 12.1; or of about 16.1; or of about 17.5; or of about 23.5.

The present invention is also directed to methods of inhibiting Hepatitis C virus replication in an HCV-infected mammal, such as a human, comprising administering to said mammal a Hepatitis C virus replication-inhibiting amount of a crystalline form of (R)-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one, or a pharmaceutically acceptable salt thereof. In other embodiments are provided such methods, wherein said crystalline form of (R)-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one exhibits any one of a characteristic peak in the powder x-ray diffraction pattern, expressed in degrees two-theta, selected from of about 7.1; or of about 12.1; or of about 16.1; or of about 17.5; or of about 23.5.

The present invention also relates to the use of a crystalline form of (R)-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one, or a pharmaceutically acceptable salt thereof, in the preparation of a medicament for the treatment of a mammal suffering from infection with Hepatitis C virus. The medicament may comprise a Hepatitis C virus-inhibiting amount of a crystalline form of (R)-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one, or a pharmaceutically acceptable salt thereof, and a pharmaceutically acceptable carrier or carriers. In other embodiments are provided such medicaments, wherein said crystalline form of (R)-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one exhibits any one of a characteristic peak in the powder x-ray diffraction pattern, expressed in degrees two-theta, selected from of about 7.1; or of about 12.1; or of about 16.1; or of about 17.5; or of about 23.5.

As used herein, the terms "comprising" and "including" are used in their open, non-limiting sense.

The term "hydrogen," as used herein, means a substituent "—H."

The term "$C_1$-$C_6$ alkyl", as used herein, means saturated monovalent hydrocarbon radicals having straight or branched moieties, and containing from 1 to 6 carbon atoms. Examples of such groups include, but are not limited to, methyl, ethyl, propyl, iso-propyl, n-butyl, iso-butyl, tert-butyl, and such.

The term "$C_3$-$C_8$ cycloalkyl," as used herein, means a saturated or partially saturated, monocyclic, or fused or spiro polycyclic, ring structure having a total of from 3 to 8 carbon ring atoms (but no heteroatoms). Exemplary cycloalkyls include cyclopropyl, cyclobutyl, cyclopentyl, cyclopentenyl, cyclohexyl, cycloheptyl, ⌊ damantin, and like groups. The term "cyclopentyl," as used herein, means a cycloalkyl group composed of 5 carbon atoms and 9 hydrogen atoms and can be represented by the chemical formula

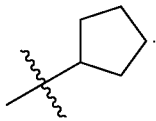

The term "$C_6$-$C_{10}$ aryl", as used herein, means a group derived from an aromatic hydrocarbon by removal of one hydrogen and containing a total of from 6 to 10 carbon atoms. The term "phenyl" and the symbol "Ph," as used herein, refer to a $C_6H_5$ group.

The term "halogen," as used herein, means fluorine, chlorine, bromine, or iodine. The term "fluoro" means fluorine, "chloro" means chlorine, "bromo" means bromine, and "iodo" means iodine.

The term "cyano," means a group —C≡N, wherein there is a triple bond between the carbon atom and the nitrogen atom. A cyano group is also written herein as "—CN."

The term "trifluoromethyl," means a group —$CF_3$.

The term "treating," as used herein with respect to a chemical transformation or series of chemical transformations, refers to a chemical process or processes in which two or more reactants are allowed to come into contact with each other to effect a chemical reaction, change, or transformation. For example, when reactant A and reactant B are allowed to come into contact with each other to afford a new chemical compound(s) C, A is said to have been "treated" with B to afford C.

The term "protecting," as used herein, refers to a process in which a functional group in a chemical compound is selectively masked by a non-reactive functional group in order to allow a selective reaction(s) to occur elsewhere on said chemical compound. Such non-reactive functional groups are herein termed "protecting groups." For example, the term "hydroxyl protecting group," as used herein refers to those groups that are capable of selectively masking the reactivity of a hydroxyl (—OH) group. The term "suitable protecting group," as used herein refers to those protecting groups that are useful in the preparation of the compounds of the present invention. Such groups are generally able to be selectively introduced and removed using mild reaction conditions that do not interfere with other portions of the subject compounds. Protecting groups that are suitable for use in the processes and methods of the present invention are known to those of ordinary skill in the art. For example, suitable protecting groups for a ⌊ damanti (—OH) group include, but are not limited to, trialkylsilyl ethers (such as —Si($CH_3$)$_3$), alkyl ethers (such as —$CH_3$), unsubstituted and substituted benzyl ethers (such as —$CH_2C_6H_5$ and para-methoxybenzyl ether). The chemical properties of such protecting groups, methods for their introduction, and their removal can be found, for example, in T. Greene and P. Wuts, *Protective Groups in Organic Synthesis* (3$^{rd}$ ed.), John Wiley & Sons, NY (1999). The terms "deprotecting," "deprotected," or "deprotect," as used herein, are meant to refer to the process of removing a protecting group from a compound.

The terms "hydrolyze," "hydrolyzing," "hydrolysis," and "hydrolyzed," as used herein, all mean and refer to a chemical reaction in which an ester, an amide, or both are converted into their corresponding carboxylic acid derivatives, through the action of a proton ($H^+$) or hydroxyl anion (—OH), such as would be present in either an acidic or basic aqueous solution.

The term "leaving group," as used herein, refers to a chemical functional group that generally allows a nucleophilic substitution reaction to take place at the atom to which it is attached. For example, in acid chlorides of the formula Cl—C(O)R, wherein R is alkyl, aryl, or heterocyclic, the —Cl group is generally referred to as a leaving group because it allows nucleophilic substitution reactions to take place at the carbonyl carbon to which it is attached. Suitable leaving groups are known to those of ordinary skill in the art and can include halides, aromatic heterocycles, cyano, amino groups (generally under acidic conditions), ammonium groups, alkoxide groups, carbonate groups, ⌊ damant, and ⌊ damanti groups that have been activated by reaction with compounds such as carbodiimides. For example, suitable leaving groups can include, but are not limited to, chloride, bromide, iodide, cyano, imidazole, and ⌊ damanti groups that have been allowed to react with a carbodiimide such as dicyclohexylcarbodiimide (optionally in the presence of an additive such as hydroxybenzotriazole) or a carbodiimide derivative.

The term "combination of reagents," means a chemical reagent, or more than one reagent when necessary, that can be used to affect a desired chemical reaction. The choice of a particular reagent, or combination or reagents, will depend on factors that are familiar to those of ordinary skill in the art and include, but are not limited to, the identity of the reactants, the presence of other functional groups in the reactants, the solvent or solvents used in a particular chemical reaction, the temperature at which the chemical reaction will be performed, and the method or methods of purification of the desired chemical reaction product. The choice of a reagent, or combination of reagents, required to affect a particular chemical reaction are within the knowledge of one of ordinary skill in the art and such a choice can be made without undue experimentation. In the present invention, compounds of formula (I) can be treated with, for example, an anion of a malonate derivative, such as a malonate ester. For example, compounds of formula (I) can be treated with a magnesium malonate ester, such as ethyl magnesium malonate, to afford a compound of formula (III). In such a case, the magnesium malonate ester would be termed the "reagent." If the magnesium malonate ester were prepared in situ and used without isolation or further purification, it would be termed a "combination of reagents."

The term "base," as used herein, means a so-called Bronsted-Lowry base. A Bronsted-Lowry base is a reagent that is capable of accepting a proton ($H^+$) from an acid present in a reaction mixture. Examples of Bronsted-Lowry bases include, but are not limited to, inorganic bases such as sodium carbonate, sodium bicarbonate, sodium hydroxide, potassium carbonate, potassium bicarbonate, potassium hydroxide, and cesium carbonate, inorganic bases such as triethylamine, diisopropylethylamine, diisopropylamine, dicyclohexylamine, morpholine, pyrrolidone, piperidine, pyridine, 4-N,N-dimethylaminopyridine (DMAP), and imidazole.

The term "acid," as used herein, refers to both suitable Bronsted-Lowry and Lewis acids. Bronsted-Lowry acids are those compounds or reagents that are capable of donating a proton ($H^+$) to a base present in a reaction mixture. Bronsted-Lowry acids include both inorganic and organic acids. Inorganic acids include, but are not limited to, hydrochloric acid, hydrobromic acid, hydroiodic acid, sulfuric acid, and nitric acid. Organic acids include, but are not limited to, sulfonic acids (such as methanesulfonic acid, trifluoromethane sulfonic, and tosic acid), and carboxylic acids (formic acid, acetic acid, and benzoic acid). A Lewis acid is a chemical compound that is capable of accepting an electron pair from a corresponding Lewis base to form a so-called Lewis adduct by coordination. A Lewis base is a chemical compound that is capable of donating an electron pair to a corresponding Lewis acid. Suitable Lewis acids include, but are not limited to, aluminium (III) chloride, titanium (II) chloride, titanium (I) chloride, tin (II) chloride, and tin (I) chloride.

The term "chiral, non-racemic base," as used herein, means a basic compound that can exist in an enantiomeric form and is not present in an equal amount with its corresponding opposite enantiomer. For example, the compound 2-phenylglycinol exists as two enantiomers of opposite configuration, the so-called (R)- and (S)-enantiomers. If the (R)- and the (S)-enantiomers are present in equal amounts, such a mixture is said to be "racemic." If, however, one enantiomer is present in an amount greater than the other, the mixture is said to be "non-racemic."

The term "stereoisomers" refers to compounds that have identical chemical constitution, but differ with regard to the arrangement of their atoms or groups in space. In particular, the term "enantiomers" refers to two stereoisomers of a compound that are non-superimposable mirror images of one another. The terms "racemic" or "racemic mixture," as used herein, refer to a 1:1 mixture of enantiomers of a particular compound. The term "diastereomers", on the other hand, refers to the relationship between a pair of stereoisomers that comprise two or more asymmetric centers and are not mirror images of one another.

The term "stereochemically-enriched" product, when used herein, refers to a reaction product wherein a particular stereoisomer is present in a statistically significant greater amount relative to the other possible stereoisomeric products. For example, a product that comprises more of one enantiomer than the other would constitute a stereochemically enriched product. Similarly, a product that comprises more of one diastereoisomer than others would also constitute a stereochemically enriched product. The methods and processes contained herein are said to afford a "stereochemically enriched" product. In such cases, the methods and processes contained herein begin with a mixture of stereoisomeric compounds in which all possible stereoisomers are present in about an equal amount and afford a product in which at least one stereoisomer is present in a statistically significant greater amount than the others.

The term "diastereomeric," as used herein refers to the relationship between a pair of stereoisomers that comprise two or more asymmetric centers and are non-superimposable mirror images of one another. The phrases "diastereomeric salt," or "diastereomeric salts," as used herein means a salt of a diastereomeric compound, wherein "diastereomer" is as defined herein.

The term "racemic," as used herein, means a composition comprising a 1:1 ratio of enantiomers. The term "scalemic," as used herein, means a composition comprising an unequal amount of enantiomers. For example, a composition comprising a 1:1 mixture of the (R)- and (S)-enantiomers of a compound of the present invention is termed a racemic composition or mixture. As an additional example, a composition comprising a 2:1 mixture of (R)- and (S)-enantiomers of a compound of the present invention is termed a scalemic composition or mixture. It is specifically contemplated that the methods of the present invention may be advantageously used to prepare a scalemic compound of the present invention from a racemic compound of the present invention.

The terms "resolution" and "resolving" mean a method of physically separating stereoisomeric compounds from a mixture of stereoisomers, such as a racemic mixture comprising two enantiomers of a particular compound. As used herein, "resolution" and "resolving" are meant to include both partial and complete resolution.

The terms "separating" or "separated," as used herein, mean a process of physically isolating at least two different chemical compounds from each other. For example, if a chemical reaction takes place and produces at least two products, (A) and (B), the process of isolating both (A) and (B) from each other is termed "separating" (A) and (B). It is specifically contemplated that the separations of the present invention may be partial or complete as determined by analytical techniques known to those of ordinary skill in the art and those described herein.

The term "converting," as used herein, means allowing a chemical reaction to take place with a starting material or materials to produce a different chemical product. For example, if chemical reactants (A) and (B) are allowed to react with each other to produce product (C), starting materials (A) and (B) can be said to have "converted" to product (C), or it can be said that (A) was "converted" to (C), or that (B) was "converted" to (C).

The term "suitable counter-ion," as used herein, means an ion or ions opposite in charge to the ion present in the compound or compounds of the invention such that the overall complex or salt has a neutral charge. For example, if the compound of the present invention contains an overall negative one (−1) charge, a suitable counter ion would be one with an overall positive one (+1) charge that would afford an overall neutral charge for the complex or salt. Examples of suitable positive (+) counter-ions include, but are not limited to, sodium ion ($Na^+$), potassium ion ($K^+$), cesium ion ($Cs^+$), and protonated amines (such as protonated triethylamine, protonated dicyclohexylamine, protonated morpholine, or protonated pyridine). Alternatively, if the compound of the invention contains an overall positive one (+1) charge, a suitable counter-ion would be one with an overall negative one (−1) charge that would afford an overall neutral charge for the complex or salt. Examples of suitable negative (−) counter-ions include, but are not limited to, fluoride (F⁻), chloride (Cl⁻), bromide (Br⁻), iodide (I⁻), hydroxide (⁻OH), and acetate (⁻O—C(O)CH₃). It is also possible that the suitable counter-ion in the compounds of the present invention, including the compounds used in the methods of the present invention, may have more than a single charge associated with them. For example, if the compound of the invention contains a negative one (−1) charge, the suitable counter-ion may contain a plus two (+2) charge, such that two compounds of the invention with negative one charges are associated with one suitable counter-ion. Examples, of suitable counter-ions with more than one positive charge include, but are not limited to calcium (Ca²⁺). Finally, it is also contemplated that the compounds of the present invention may contain more than one charge, such that more than one suitable counter-ion may be required to afford an overall neutral complex or salt. For example, the compound of the present invention may contain more than one negative one (−1) charges, such that two suitable counter-ions, each with a plus one (+1) charge, are required to afford an overall neutral complex or salt.

The term "substituted," means that the specified group or moiety bears one or more substituents. The term "unsubstituted," means that the specified group bears no substituents. The term "optionally substituted" means that the specified group is unsubstituted or substituted by one or more substituents.

Solutions of individual stereoisomeric compounds of the present invention may rotate plane-polarized light. The use of either a "(+)" or "(−)" symbol in the name of a compound of the invention indicates that a solution of a particular stereoisomer rotates plane-polarized light in the (+) or (−) direction, as measured using techniques known to those of ordinary skill in the art.

The term "HCV," as used herein, refers to Hepatitis C virus.

The terms "inhibiting Hepatitis C virus" and "inhibiting Hepatitis C virus replication" mean inhibiting Hepatitis C virus replication either in vitro or in vivo, such as in a mammal, such as a human, by contacting the Hepatitis C virus with an HCV-replication inhibiting amount of a compound of the present invention, or a pharmaceutically acceptable salt or solvate thereof. Such inhibition may take place in vivo, such as in a mammal, such as a human, by administering to the mammal a Hepatitis C virus-inhibiting amount of a compound of the present invention. The amount of a compound of the present invention necessary to inhibit replication of the HCV virus either in vitro or in vivo, such as in a mammal, such as a human, can be determined using methods known to those of ordinary skill in the art. For example, an amount of a compound of the invention may be administered to a mammal, either alone or as part of a pharmaceutically acceptable formulation. Blood samples may then be withdrawn from the mammal and the amount of Hepatitis C virus in the sample may be quantified using methods known to those of ordinary skill in the art. A reduction in the amount of Hepatitis C virus in the sample compared to the amount found in the blood before administration of a compound of the invention would represent inhibition of the replication of Hepatitis C virus in the mammal. The administration of a compound of the invention to the mammal may be in the form of single dose or a series of doses over successive days.

The term "HCV-inhibiting agent," as used herein, means a crystalline form of (R)-6-cyclopentyl-6-(2-(2,6- diethylpyridin-4-yl)ethyl)-3-((5,7-dimethyl-[1,2,4]triazolo[1,5-a]pyrimidin-2-yl)methyl)-4-hydroxy-5,6-dihydropyran-2-one, or a pharmaceutically acceptable salt thereof.

The term "HCV-inhibiting amount," as used herein, refers to an amount of a compound of the present invention that is sufficient to inhibit the replication of the Hepatitis C virus when administered to a mammal, such as a human.

The term "HCV polymerase-inhibiting amount," as used herein, means an amount of a compound of the present invention that is sufficient to inhibit the function of the Hepatitis C virus polymerase enzyme when the compound is placed in contact with the enzyme.

The term "treating", as used herein with respect to the treatment of HCV-infected mammals, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

The phrase "pharmaceutically acceptable salt(s)", as used herein, unless otherwise indicated, includes salts of acidic or basic groups, which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of the present invention are those that form non-toxic acid addition salts, i.e., salts containing pharmacologically acceptable anions, such as the acetate, benzenesulfonate, benzoate, bicarbonate, bisulfate, bitartrate, borate, bromide, calcium [ damanti, camsylate, carbonate, chloride, clavulanate, citrate, dihydrochloride, [ damanti, edislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, [ damantin/diphosphate, polygalacturonate, salicylate, stearate, subacetate, succinate, tannate, tartrate, teoclate, tosylate, triethiodode, and valerate salts.

The phrases "therapeutically effective amount," "effective amount," and "HCV-inhibiting amount," are intended to mean the amount of an inventive agent that, when administered to a mammal in need of treatment, is sufficient to effect treatment for injury or disease conditions alleviated by the inhibition of HCV RNA replication such as for potentiation of anti-cancer therapies or inhibition of neurotoxicity consequent to stroke, head trauma, and neurodegenerative diseases. The amount of a given HCV-inhibiting agent used in the method of the invention that will be therapeutically effective will vary depending upon factors such as the particular HCV-inhibiting agent, the disease condition and the severity thereof, the identity and characteristics of the mammal in need thereof, which amount may be routinely determined by artisans.

DETAILED DESCRIPTION

Figure 1:
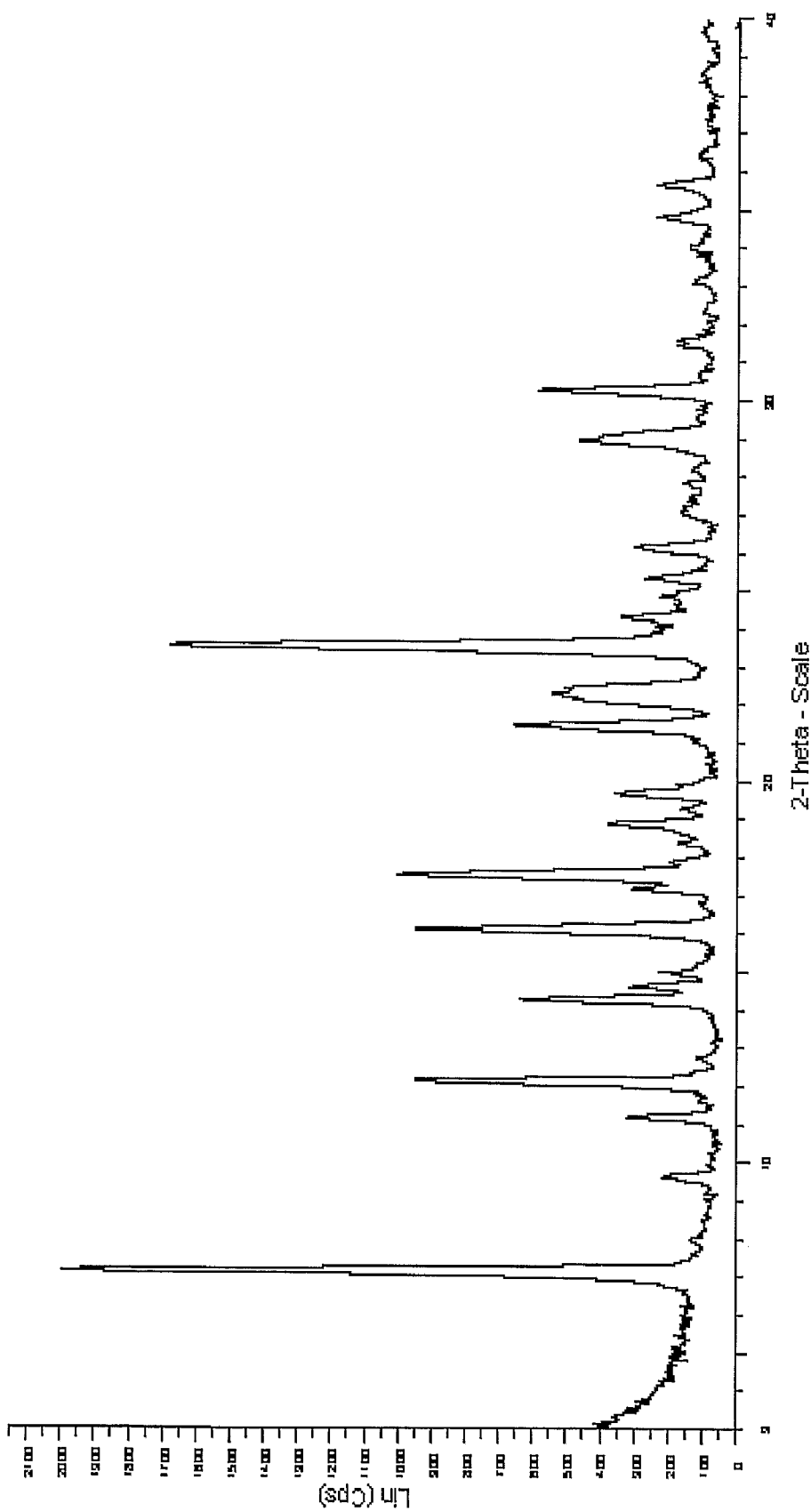
FIG. 1 is a representative powder x-ray diffraction pattern of a crystalline form of (R)-6-cyclopentyl-6-(2-(2,6-diethylpyrdin-4-yl)ethyl)-3-((5,7-dimethyl-[1,2,4]triazolo[1,5-a]pyrimidin-2-yl)methyl)-4-hydroxy-5,6-dihydropyran-2-one.

In accordance with a convention used in the art, the symbol

is used in structural formulas herein to depict the bond that is the point of attachment of the moiety or substituent to the core or backbone structure. In accordance with another convention, in some structural formulae herein the carbon atoms and their bound hydrogen atoms are not explicitly depicted, e.g.,

represents a methyl group,

represents an ethyl group,

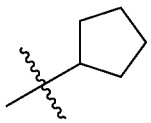

represents a cyclopentyl group, etc.

The compounds of the present invention may exist in several tautomeric forms. For example, a compound of the invention may exist in a form in which two ketones are present on a ring of the compound, as shown in (A) below. Alternatively, the compounds of the present invention may exist in at least two different enol forms, as shown in compounds (B) and (C) below. These three forms may be in equilibrium and the compounds of the invention may exist in more than one of these forms at the same time. For example, in a particular compound of the invention, a certain percentage of the molecules may be present in form (A) while the remainder are present in form (B) or form (C). Which form predominates in a particular compound of the invention depends on several factors that include, but are not limited to, whether the compound is in solid, liquid, or crystalline form, whether the compound is dissolved in a solvent and the identity of the solvent, the environmental temperature, and the relative humidity. It is specifically contemplated that when the compounds of the present invention are drawn in a particular form, form (A) for example, all the tautomeric forms, forms (B) and (C) for example, are included as well.

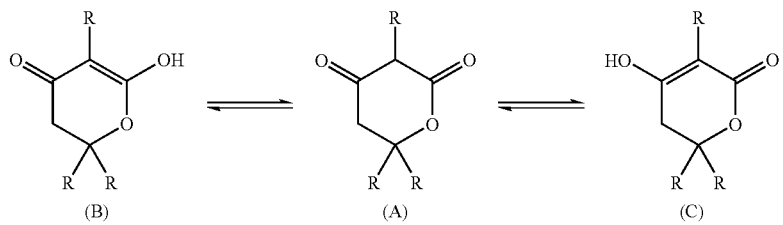

The compounds of the present invention may have asymmetric carbon atoms. The carbon-carbon bonds of the compounds of the present invention may be depicted herein using a solid line ( —— ), a solid wedge ( ▬ ), or a dotted wedge ( ⋯⋯ ). The use of a solid line to depict bonds to asymmetric carbon atoms is meant to indicate that all possible stereoisomers at that carbon atom are included. The use of either a solid or dotted wedge to depict bonds to asymmetric carbon atoms is meant to indicate that only the stereoisomer shown is meant to be included. It is possible that compounds of the invention may contain more than one asymmetric carbon atom. In those compounds, the use of a solid line to depict bonds to asymmetric carbon atoms is meant to indicate that all possible stereoisomers are meant to be included. The use of a solid line to depict bonds to one or more asymmetric carbon atoms in a compound of the invention and the use of a solid or dotted wedge to depict bonds to other asymmetric carbon atoms in the same compound is meant to indicate that a mixture of diastereomers is present.

Diastereomeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomeric mixture by reaction with an appropriate optically active compound (e.g., a chiral, non-racemic base), separating the diastereomers and converting (e.g., hydrolyzing) the individual diastereomers to the corresponding pure enantiomers. All such isomers, including diastereomeric mixtures and pure enantiomers are considered as part of the invention.

Alternatively, individual stereoisomeric compounds of the present invention may be prepared in enantiomerically enriched form by asymmetric synthesis. Asymmetric synthesis may be performed using techniques known to those of skill in the art, such as the use of asymmetric starting materials that are commercially available or readily prepared using methods known to those of ordinary skill in the art, the use of asymmetric auxiliaries that may be removed at the completion of the synthesis, or the resolution of intermediate compounds using enzymatic methods. The choice of such a method will depend on factors that include, but are not limited to, the availability of starting materials, the relative efficiency of a method, and whether such methods are useful for the compounds of the invention containing particular functional groups. Such choices are within the knowledge of one of ordinary skill in the art.

Furthermore, a "stereoselective process" is one that produces a particular stereoisomer of a reaction product in preference to other possible stereoisomers of that product. Enantioselectivity is generally quantified as "enantiomeric excess" (ee) defined as follows: [% enantiomeric excess A(ee)=(% enantiomer A)−(% enantiomer B)], where A and B are the enantiomeric products formed from the starting materials.

When the compounds of the present invention contain asymmetric carbon atoms, the derivative salts, prodrugs and solvates may exist as single stereoisomers, racemates, and/or mixtures of enantiomers and/or diastereomers. All such single stereoisomers, racemates, and mixtures thereof are intended to be within the scope of the present invention.

As generally understood by those skilled in the art, an optically pure compound is one that is enantiomerically pure. Preferably, an optically pure compound according to the present invention comprises at least 90% of a single stereoisomer (80% enantiomeric excess), more preferably at least 95% (90% e.e.), even more preferably at least 97.5% (95% e.e.), and most preferably at least 99% (98% e.e.).

The crystal forms comprising the present invention have been characterized using powder X-ray diffractometry (PXRD), solid state NMR (ssNMR), and differential scanning calorimetry (DSC). One of ordinary skill in the art will appreciate that an X-ray diffraction pattern, a solid state NMR spectrum, and a differential scanning calorimetry scan may be obtained with a measurement error that is dependent upon the measurement conditions employed. In particular, it is generally known that intensities in an X-ray diffraction pattern may fluctuate depending upon measurement conditions employed. It should be further understood that relative intensities may also vary depending upon experimental conditions and, accordingly, the exact order of intensity should not be taken into account. Additionally, a measurement error of diffraction angle for a conventional X-ray diffraction pattern is typically about 0.1 expressed in degrees 2-theta, and such degree of measurement error should be taken into account as pertaining to the aforementioned diffraction angles. Furthermore, a measurement error of ppm in a solid state NMR spectrum is typically about 0.2 ppm, and such degree of measurement error should be taken into account as pertaining to the aforementioned diffraction angles. Further, all reference to "ppm" in relation to peaks in a solid state NMR spectrum are in relation to an external standard of crystalline [ damantine, setting its upfield resonance to 29.5 ppm. Consequently, it is to be understood that a crystal form of the present invention is not limited to a crystal form that provides an X-ray diffraction pattern, ssNMR spectrum, or DSC trace that are completely identical to the X-ray diffraction pattern, ssNMR spectrum, or DSC trace depicted in the accompanying Figures disclosed herein. Any crystal form that provides an X-ray diffraction pattern, ssNMR spectrum, or DSC trace substantially identical to the one disclosed in the accompanying Figures falls within the scope of the present invention. The ability to ascertain substantial identities of an X-ray diffraction pattern, ssNMR spectrum, or DSC trace is within the purview of one of ordinary skill in the art.

If a derivative used in the method of the invention is a base, a desired salt may be prepared by any suitable method known to the art, including treatment of the free base with an inorganic acid, such as hydrochloric acid; hydrobromic acid; sulfuric acid; nitric acid; phosphoric acid; and the like, or with an organic acid, such as acetic acid; maleic acid; succinic acid; mandelic acid; fumaric acid; malonic acid; pyruvic acid; oxalic acid; glycolic acid; salicylic acid; pyranosidyl acid, such as glucuronic acid or galacturonic acid; alpha-hydroxy acid, such as citric acid or tartaric acid; amino acid, such as aspartic acid or glutamic acid; aromatic acid, such as benzoic acid or cinnamic acid; sulfonic acid, such as p-toluenesulfonic acid or ethanesulfonic acid; and the like.

If a derivative used in the method of the invention is an acid, a desired salt may be prepared by any suitable method known to the art, including treatment of the free acid with an inorganic or organic base, such as an amine (primary, secondary, or tertiary); an alkali metal or alkaline earth metal hydroxide; or the like. Illustrative Examples of suitable salts include organic salts derived from amino acids such as glycine and arginine; ammonia; primary, secondary, and tertiary amines; and cyclic amines, such as piperidine, morpholine, and piperazine; as well as inorganic salts derived from sodium, calcium, potassium, magnesium, manganese, iron, copper, zinc, aluminum, and lithium.

The compounds of the present invention can be prepared as follows. It is to be understood that the specifics of the methods described herein are only representative of those that one of ordinary skill in the art could use to prepare the compounds of the present invention. Suitable alternatives and equivalents, including alternative reagents, solvents, and temperatures, among other aspects of the presently claimed invention, can be immediately envisioned and used by those of ordinary skill in the art without undue experimentation to prepare the compounds of the present invention. Therefore, none of the descriptions that follow are meant to, and should not be construed to, limit the scope of the presently claimed invention in any way.

The compounds of formula (Ia),

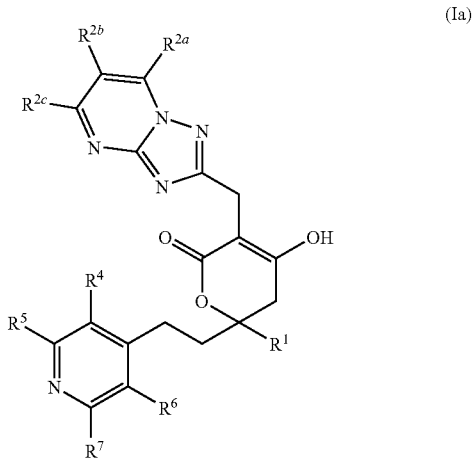

(Ia)

wherein:

$R^1$ is $C_1$-$C_6$ alkyl or $C_3$-$C_6$ cycloalkyl;

$R^{2a}$, $R^{2b}$, and $R^{2c}$ are each independently selected from hydrogen, halogen, $C_1$-$C_6$ alkyl, $C_3$-$C_6$ cycloalkyl, —$OR^{12a}$, —$CF_3$, —CN, and —$NR^{12a}R^{12b}$;

$R^4$ is selected from hydrogen, $C_1$-$C_6$ alkyl, —$(CR^9R^{10})_n R^{11}$, —$CF_3$, halogen, —$OR^{12a}$, —CN, and —$NR^{12a}R^{12b}$;

$R^5$ is selected from hydrogen, $C_1$-$C_6$ alkyl, —$(CR^9R^{10})_n R^{11}$, —$CF_3$, halogen, —$OR^{12a}$, —CN, and —$NR^{12a}R^{12b}$;

$R^6$ is selected from hydrogen, $C_1$-$C_6$ alkyl, —$(CR^9R^{10})_n R^{11}$, —$CF_3$, halogen, —$OR^{12a}$, —CN, and —$NR^{12a}R^{12b}$;

$R^7$ is selected from hydrogen, $C_1$-$C_6$ alkyl, —$(CR^9R^{10})_n R^{11}$, —$CF_3$, halogen, —$OR^{12a}$, —CN, and —$NR^{12a}R^{12b}$;

each $R^9$ and $R^{10}$ is independently selected from hydrogen and $C_1$-$C_6$ alkyl, or $R^9$ and $R^{10}$, together with the atom to which they are attached, form a $C_3$-$C_6$ cycloalkyl group;

each $R^{11}$ is independently selected from hydrogen, $C_1$-$C_6$ alkyl, halogen, —$OR^{12}$, —CN, —$CF_3$, and —$NR^{12a}R^{12b}$;

each $R^{12a}$ and $R^{12b}$; is independently selected from hydrogen and $C_1$-$C_6$ alkyl; and each n is independently chosen and is an integer from 0 to 5; can be prepared by reaction of compounds of formula (II), wherein $R^1$ and $R^2$ are as defined herein, with compounds of formula (IX),

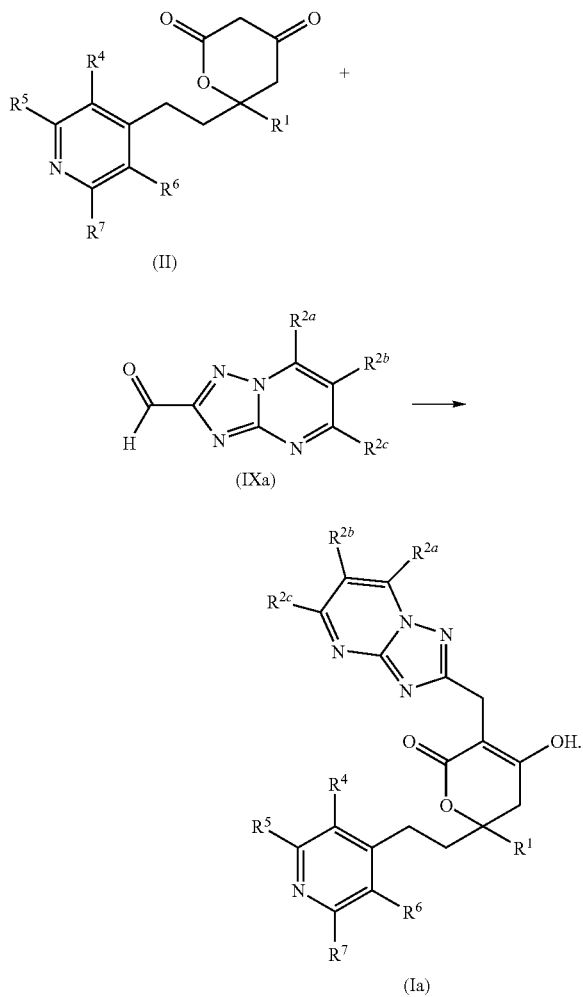

These reactions are generally performed in the presence of a reducing agent, such as a borane source or hydrogen in the presence of suitable catalyst. Suitable borane sources include, but are not limited to, diborane, borane-THF, borane-dimethylsulfide, borane-trimethylamine complex, borane-dimethylamine complex, borane t-butyl amine complex, and borane-pyrdine complex. Suitable catalysts for use in the presence of a reducing agent such as hydrogen include, but are not limited to, nickel, palladium, platinum, rhodium and ruthenium. Furthermore, such reactions are performed in a solvent or mixture of solvents that will not interfere with desired chemical reaction. Furthermore, appropriate solvents include those that are known to those of skill in the art to be compatible with the reaction conditions and include alkyl esters and aryl esters, alkyl, heterocyclic, and aryl ethers, hydrocarbons, alkyl and aryl alcohols, alkyl and aryl halogenated compounds, alkyl or aryl nitriles, alkyl and aryl ketones, and non-protic heterocyclic solvents. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, benzene, toluene, anisole, xylenes, and pyridine, or any mixture of the above solvents. Additionally, water may be used as a co-solvent if it will not interfere with the desired transformation. Finally, such reactions can be performed at a temperature in the range of from about 0° C. to about 75° C., preferably in the range of from about −20° C. to about 32° C., most preferably at room or ambient temperature. The choice of a particular reducing agent, solvent, and temperature will depend on several factors including, but not limited to, the identity of the particular reactants and the functional groups present in such reactants. Such choices are within the knowledge of one of ordinary skill in the art and can be made without undue experimentation.

Alternatively, compounds of formula (Ia) may be prepared by reaction of a compound of formula (II) with a compound of formula (Ixb), wherein X is a suitable leaving group. Suitable leaving groups include, but are not limited to, halides (such as chloride, bromide, and iodide), and activated esters (such as methanesulfonate, trifluoromethane sulfonate, and tosyl esters). Such reactions can be performed in the presence of a suitable base. Suitable bases include, but are not limited to, sodium carbonate, sodium bicarbonate, potassium carbonate, cesium carbonate, sodium hydroxide, potassium hydroxide, sodium hydride, lithium hydride, potassium hydride, lithium diisopropylamide, pyridine, triethylamine, tributylamine, triethanolamine, N-methylmorpholine, N-ethyl-N,N-diisopropylamine, and 4-N,N-dimethylaminopyridine. Furthermore, appropriate solvents include those that are known to those of skill in the art to be compatible with the reaction conditions and include alkyl, heterocyclic, and aryl ethers, hydrocarbons, alkyl and aryl halogenated compounds, alkyl or aryl nitriles, and non-protic heterocyclic solvents. For example, suitable solvents include, but are not limited to, dimethoxyethane, diisopropyl ether, chlorobenzene, dimethyl formamide, dimethyl acetamide, propionitrile, butyronitrile, diethyl ether, methyl-t-butyl ether, diphenyl ether, methylphenyl ether, tetrahydrofuran, 2-methyltetrahydrofuran, 1,4-dioxane, pentane, hexane, heptane, acetonitrile, benzonitrile, benzene, toluene, anisole, xylenes, and pyridine, or any mixture of the above solvents. Additionally, water may be used as a co-solvent if it will not interfere with the desired transformation. Finally, such reactions can be performed at a temperature in the range of from about 0° C. to about 150° C., preferably in the range of from about 0° C. to about 32° C., most preferably at room or ambient temperature. Such choices are within the knowledge of one of ordinary skill in the art and can be made without undue experimentation.

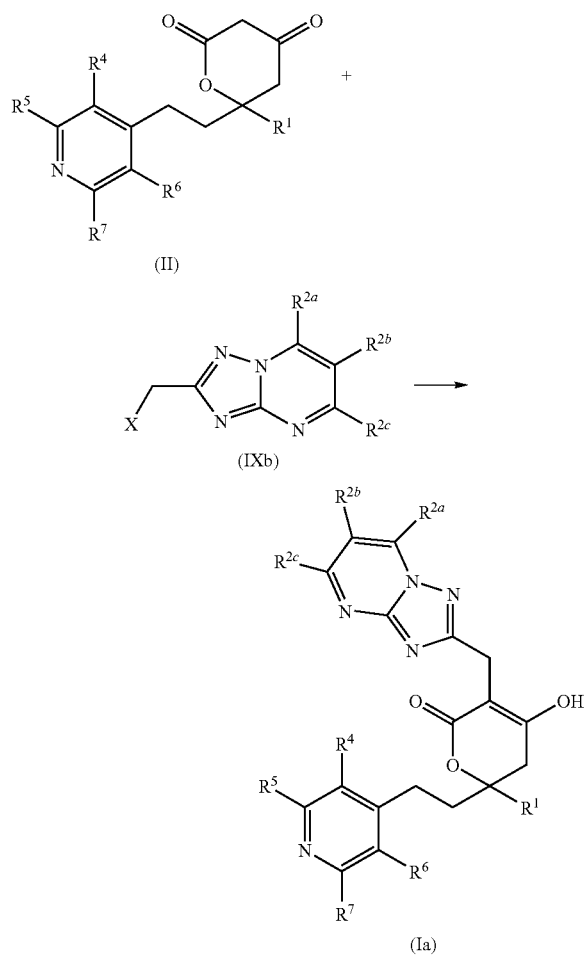

Compounds of formula (II), wherein $R^1$, $R^4$, $R^5$, $R^6$, and $R^7$ are as hereinbefore defined,

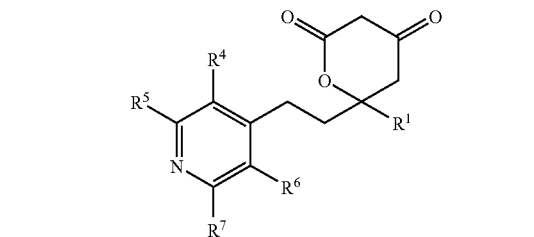

can be prepared from compounds of formula (III), wherein $R^1$, $R^4$, $R^5$, $R^6$, and $R^7$ are as hereinbefore defined and $R^{14}$ is $C_1$-$C_6$ alkyl or benzyl, by reaction with a suitable acid or base.

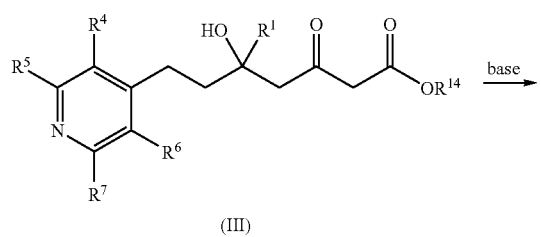

-continued

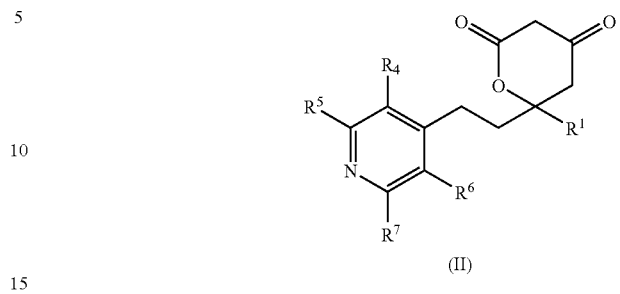

Suitable bases for use in these reactions include inorganic bases and organic bases. Suitable inorganic bases include, but are not limited to, sodium carbonate, sodium bicarbonate, potassium carbonate, potassium bicarbonate, sodium hydroxide, sodium hydride, potassium hydride, and cesium carbonate. Preferably, the base is potassium carbonate. Suitable organic bases include, but are not limited to, pyridine, triethylamine, tributylamine, triethanolamine, N-methylmorpholine, N-ethyl-N,N-diisopropylamine, DBU, and 4-N,N-dimethylaminopyridine. These reactions can also be performed in the presence of a catalytic amount of a suitable acid. Suitable acids include both Bronsted-Lowry and Lewis acids. Furthermore, these reactions are generally performed in a solvent or mixture of solvents that will not interfere with desired chemical reaction. Furthermore, appropriate solvents include those that are known to those of skill in the art to be compatible with the reaction conditions and include alkyl esters and aryl esters, alkyl, heterocyclic, and aryl ethers, hydrocarbons, alkyl and aryl alcohols, alkyl and aryl halogenated compounds, alkyl or aryl nitriles, alkyl and aryl ketones, and non-protic heterocyclic solvents. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent if it will not interfere with the desired transformation. Finally, such reactions can be performed at a temperature in the range of from about 0° C. to about 100° C., or in the range of from about 25° C. to about 100° C., or in the range of from about 35° C. to about 75° C., or in the range of from about 45° C. to about 55° C., or at about 50° C. The choice of a particular solvent, and temperature will depend on several factors including, but not limited to, the identity of the particular reactants and the functional groups present in such reactants. Such choices are within the knowledge of one of ordinary skill in the art and can be made without undue experimentation.

Alternatively, the compounds of formula (II), wherein $R^1$, $R^4$, $R^5$, $R^6$, and $R^7$ are as hereinbefore defined, can be prepared from compounds of formula (III), wherein $R^1$, $R^4$, $R^5$, $R^6$, and $R^7$ are as hereinbefore defined, and $R^{14}$ is hydrogen, by reaction with a suitable reagent, or a combination of suitable reagents, to affect cyclization.

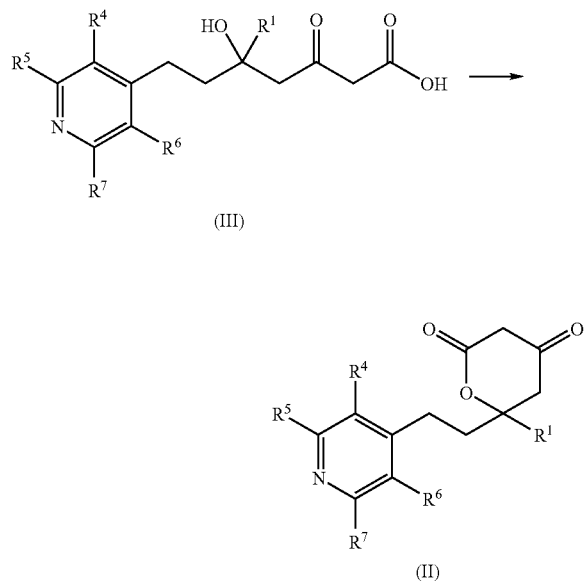

Such reactions may be performed in the presence of a reagent or combination of reagents that will convert the carboxylic —OH group into a suitable leaving group, such as chlorine or an imidazole group, for example. The term "a suitable leaving group" means a chemical group that is capable of being displaced when a suitable nucleophilic group, such as a hydroxyl group, reacts with the carbonyl carbon in the carboxyl group in the compounds of formula (III). Such suitable leaving groups can be introduced in the compounds of formula (III) wherein $R^{14}$ is hydrogen, by reaction of the compound of formula (III) with a suitable reagent or combination of reagents known to those of ordinary skill in the art. For example, a compound of formula (III), wherein $R^{14}$ is hydrogen, may be allowed to react with phosgene (ClC(O)Cl), triphosgene ((Cl)$_3$C(O)(Cl)$_3$), SOCl$_2$, or (COCl)$_2$, to afford a so-called acid chloride, that is where the carboxy hydroxyl group has been replaced with a chlorine atom. Furthermore, the compounds of formula (III) may be converted to compounds wherein the carboxy hydroxyl group is replaced by another type of suitable leaving group, such as an imidazole group. Such compounds can be prepared using a suitable reagent or combination of reagents such as carbonyl diimidazole. These types of reactions may be performed in the presence of a suitable base, such as triethylamine for example, and in an aprotic solvent that will not interfere with the desired chemical reaction, chloroform or dichloromethane for example. Furthermore, such reactions may be performed at a temperature in the range from about −78° C. to about 75° C., or in the range of from about 0° C. to about 50° C., or from about 0° C. to about 25° C. The choice of a suitable reagent to convert the carboxyl group into an acid chloride, for example, a suitable solvent, and a suitable temperature are all choices within the knowledge of one of ordinary skill in the art and can be made without undue experimentation.

The compounds of formula (III), wherein the carboxy hydroxyl group has been converted to an appropriate leaving group, an acid chloride for example, may then be converted to compounds of formula (II) by reaction in the presence of a suitable base. Suitable bases include, but are not limited to, inorganic bases and organic bases. Suitable inorganic bases include, but are not limited to, sodium carbonate, sodium bicarbonate, potassium carbonate, potassium bicarbonate, and cesium carbonate. Suitable organic bases include, but are not limited to, pyridine, triethylamine, diethylisopropyl amine, and 4-N,N-dimethylaminopyridine. Furthermore, appropriate solvents include those that are known to those of skill in the art to be compatible with the reaction conditions and include alkyl esters and aryl esters, alkyl, heterocyclic, and aryl ethers, hydrocarbons, alkyl and aryl alcohols, alkyl and aryl halogenated compounds, alkyl or aryl nitriles, alkyl and aryl ketones, and non-protic heterocyclic solvents. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. The particular choices of activating agent, solvent, base, and temperature to affect the desired transformation are all choices within the knowledge of one of ordinary skill in the art and can be made without undue experimentation.

Compounds of formula (III), wherein $R^1$, $R^4$, $R^5$, $R^6$, and $R^7$ are as hereinbefore defined, $P^1$ is hydrogen or a suitable protecting group, and $R^{14}$ is $C_1$-$C_6$ alkyl, —Si($C_1$-$C_6$ alkyl)$_3$, or —CH$_2$($C_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$, can be prepared from compounds of formula (IV), wherein $R^1$, $R^4$, $R^5$, $R^6$, and $R^7$ are as hereinbefore defined, $P^1$ is hydrogen or a suitable protecting group, and $R^{13}$ is hydrogen, $C_1$-$C_6$ alkyl, —Si($C_1$-$C_6$ alkyl)$_3$, or —CH$_2$($C_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$, or from compounds of formula (IVa), wherein $R^1$, $R^4$, $R^5$, $R^6$, and $R^7$ are as hereinbefore defined, $P^1$ is hydrogen or a suitable protecting group, and L is a suitable leaving group, as shown below.

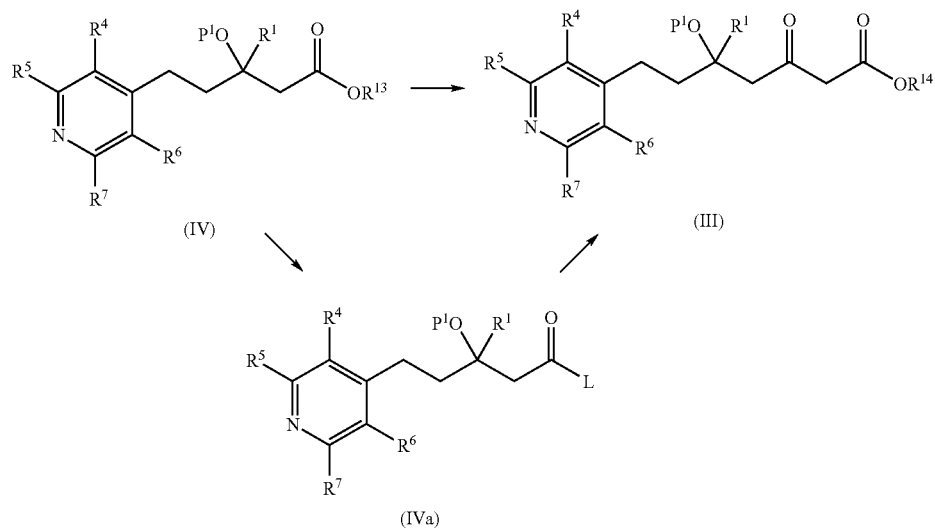

(IV)  (III)  (IVa)

The compound of formula (IV) wherein $R^{13}$ is hydrogen may be allowed to react with a reagent or combination of reagents that will convert the carboxy hydroxyl group to a suitable leaving group —OA. Such groups include activated esters, such as various benzoyl esters, such as a 2,6-dinitrobenzoyl ester or a perfluorobenzoyl ester, mixed anhydrides, or an intermediate derived from reaction of the caboxy group with a carbodiimide, such as diethyl carbodiimide or diisopropyl carbodiimide. These intermediate compounds can be prepared by reaction of the carboxy group with a suitable reagent, such as a carbodiimide, in a solvent that will not interfere with the desired chemical reaction, such as chloroform, dichloromethane, or tetrahydrofuran, and at a temperature of from about −78° C. to about 100° C., or in the range of from about 0° C. to about 75° C., or in the range of from about 0° C. to about 50° C. The compound of formula (IV) containing the suitable leaving group —OA can be isolated or can be allowed to react in the next step without any further purification. The compound containing the suitable leaving group —OA can then be allowed to react with a reagent or combination of reagents to provide the compound of formula (III). Such suitable reagents include, but are not limited to, malonate anions derived from deprotonation of a malonate derivative with a suitable base, and magnesium malonate esters, such as methyl magnesium malonate and ethyl magnesium malonate. Furthermore, appropriate solvents include those that are known to those of skill in the art to be compatible with the reaction conditions and include alkyl esters and aryl esters, alkyl, heterocyclic, and aryl ethers, hydrocarbons, alkyl and aryl alcohols, alkyl and aryl halogenated compounds, alkyl or aryl nitrites, alkyl and aryl ketones, and non-protic heterocyclic solvents. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Furthermore, they are performed at a temperature in the range of from about 0° C. to about 150° C., or in the range of from about 0° C. to about 75° C., or in the range of from about 20° C. to about 75° C., or in the range of from about 25° C. to about 50° C., or at about 40° C. The particular choice of reagent or combination or reagents, solvent or solvents, and temperature are within the knowledge of one of ordinary skill in the art and can be made without undue experimentation.

Alternatively, the compounds of formula (III) can be prepared from compounds of formula (IV), wherein $R^{13}$ is $C_1$-$C_6$ alkyl, —Si($C_1$-$C_6$ alkyl)$_3$, or —CH$_2$($C_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$, by reaction with a reagent or combination of reagents to provide the compound of formula (III). Such suitable reagents include, but are not limited to magnesium malonate esters, such as methyl magnesium malonate and ethyl magnesium malonate. Such suitable reagents include, but are not limited to, malonate anions derived from deprotonation of a malonate derivative with a suitable base, and magnesium malonate esters, such as methyl magnesium malonate and ethyl magnesium malonate. Furthermore, appropriate solvents include those that are known to those of skill in the art to be compatible with the reaction conditions and include alkyl esters and aryl esters, alkyl, heterocyclic, and aryl ethers, hydrocarbons, alkyl and aryl alcohols, alkyl and aryl halogenated compounds, alkyl or aryl nitrites, alkyl and aryl ketones, and non-protic heterocyclic solvents. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Furthermore, they are performed at a temperature in the range of from about 0° C. to about 150° C., or in the range of from about 0° C. to about 75° C., or in the range of from about 20° C. to about 75° C., or in the range of from about 25° C. to about 50° C., or at about 40° C. The particular choice of reagent or combination or reagents, solvent or solvents, and temperature are within the knowledge of one of ordinary skill in the art and can be made without undue experimentation.

Additionally, the compounds of formula (III) can be prepared from compounds of formula (IVa), wherein $R^1$, $R^4$, $R^5$, $R^6$, and $R^7$ are as hereinbefore defined, $P^1$ is hydrogen or a suitable protecting group, and L is a suitable leaving group, by reaction with a reagent or combination of reagents to provide the compound of formula (III). Suitable leaving groups include, but are not limited to, chloride, bromide, iodide, and imidazole. Compounds with suitable leaving groups can be prepared from compounds of formula (IV) wherein $R^{13}$ is —OH by reaction with an activating reagent or combination of activating reagents capable of replacing the carboxy hydroxyl group with L. Such activating reagents include, but are not limited to, thionyl chloride ($SOCl_2$), phosgene, triphosgene, oxalyl chloride, and carbonyldiimidazole. These reactions are typically performed in the presence of a base that will not interfere with the desired chemical reaction, such as triethylamine, ethyldiisopropylamine, pyridine, or 4-N,N-dimethylaminopyridine. Furthermore, the reactions are performed in an aprotic solvent that will not interfere with the desired chemical reaction such as tetrahydrofuran, methylbutyl ether, diisopropyl ether, diethyl ether, toluene, chloroform, dichloromethane, or 1,2-dichloroethane, for example. Furthermore, such reactions are performed at a temperature in the range of from about −78° C. to about 100° C., or in the range of from about −50° C. to about 100° C., or in the range of from about 0° C. to about 75° C., or in the range of from about 0° C. to about 50° C., or in the range of from about 0° C. to about 25° C. After conversion of a compound of formula (IV) to a compound of formula (IVa), the compound of formula (IVa) may be allowed to react with a reagent or combination of reagents capable of converting the compound of formula (IVa) to one of formula (III). Such suitable reagents include, but are not limited to magnesium malonate esters, such as methyl magnesium malonate and ethyl magnesium malonate. These reactions are performed in a solvent or mixture of solvents that will not interfere with the desired chemical reaction, such as diethyl ether, methyl t-butyl ether, and tetrahydrofuran, or mixtures thereof. Furthermore, they are performed at a temperature in the range of from about 0° C. to about 100° C., or in the range of from about 0° C. to about 75° C., or in the range of from about 20° C. to about 75° C., or in the range of from about 25° C. to about 50° C., or at about 40° C. The particular choice of reagent or combination or reagents, solvent or solvents, and temperature are within the knowledge of one of ordinary skill in the art and can be made without undue experimentation.

The reaction of compounds of formula (IV), (IVa), or suitably activated derivatives thereof, with a reagent or combination or reagents to afford a compound of formula (III) may require the introduction of a suitable protecting group, $P^1$, for the tertiary hydroxyl group in the compounds of formula (IV). Such protecting groups should be capable of being introduced into the compound of formula (IV) under conditions that will selectively protect such hydroxyl group. Such reagents and conditions are well-known to those of ordinary skill in the art and can be found, for example, in T. Greene and P. Wuts, *Protective Groups in Organic Synthesis* ($3^{rd}$ ed.), John Wiley & Sons, NY (1999). For example, a silyl protecting group, such as a triisopropyl silyl group, can be introduced into the compound of formula (IV) to selectively protect the tertiary hydroxyl group. Such a group can be introduced using an activated silane reagent, such as triisopropyl silyl chloride for example, in the presence of a base, such as triethylamine for example, and in an aprotic solvent, chloroform for example. The protected compound of formula (IV) may then be allowed to react as described above to afford a compound of formula (III) in protected form. The protected compound (III) can then be deprotected using conditions known to those of ordinary skill in the art. For example, if the tertiary hydroxyl group in the compound of formula (III) is protected with as a silyl ether, for example, it can be deprotected using a fluoride source, tetrabutylammonium fluoride for example, in a solvent such as THF and at a temperature in the range of from about 0° C. to about 100° C., or in the range of from about 0° C. to about 25° C. Whether the tertiary hydroxyl group in the compound of formula (IV) requires protection prior to conversion to the compound of formula (III) is within the knowledge of one of ordinary skill in the art and such a choice can be made without undue experimentation.

Reagents such as magnesium malonate esters, methyl magnesium malonate or ethyl magnesium malonate for example, are either commercially available or can be prepared using methods known to those of ordinary skill in the art. For example, ethyl magnesium malonate can be prepared by reaction of magnesium ethoxide with ethyl malonic acid, as shown below.

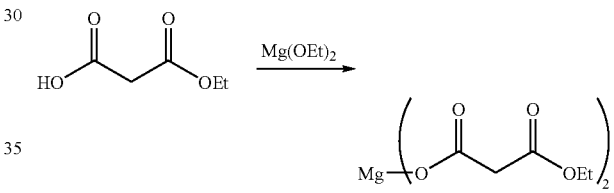

Compounds of formula (IV), wherein $R^1$, $R^4$, $R^5$, $R^6$, and $R^7$ are as hereinbefore defined, $P^1$ is hydrogen, and $R^{13}$ is hydrogen, can be prepared from compounds of formula (IV),

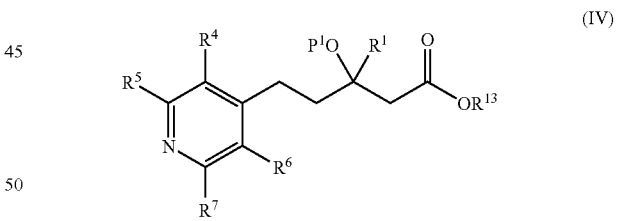

wherein $R^{13}$ is $C_1$-$C_6$ alkyl, —Si($C_1$-$C_6$ alkyl)$_3$, or —CH$_2$ ($C_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$, by hydrolysis with a suitable acid or base in an aqueous solvent. Suitable bases include, but are not limited to, lithium hydroxide, sodium hydroxide, potassium hydroxide, sodium carbonate, and potassium carbonate. Suitable acids include, but are not limited to, hydrochloric acid, hydrobromic acid, hydroiodic acid, and sulfuric acid. These reactions can be performed in a solvent or mixture of solvents that will not interfere with the desired chemical reaction including, but not limited to, diethyl ether, methyl tert-butyl ether, tetrahydrofuran, methyl alcohol, ethyl alcohol, iso-propyl alcohol, n-propyl alcohol, and tert-butyl alcohol. Water may be advantageously used as a co-solvent in these reactions. Furthermore, these reactions are typically performed at a temperature in the range from about −78° C. to about 50° C., or in the range from about −35° C. to about 50° C., or in the range of from about −35° C. to about 25° C.

Compounds of formula (IV), wherein $R^1$, $R^4$, $R^5$, $R^6$, and $R^7$ are as hereinbefore defined, $P^1$ is hydrogen or a suitable protecting group, and $R^{13}$ is hydrogen, $C_1$-$C_6$ alkyl, —Si($C_1$-$C_6$ alkyl)$_3$, or —CH$_2$($C_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$, can be prepared by reaction of a compound of formula (V), wherein $R^1$, $R^4$, $R^5$, $R^6$, and $R^7$ are as hereinbefore defined, with a compound of formula (X), wherein $R^{13}$ is hydrogen, $C_1$-$C_6$ alkyl, —Si($C_1$-$C_6$ alkyl)$_3$, or —CH$_2$($C_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$, as shown below.

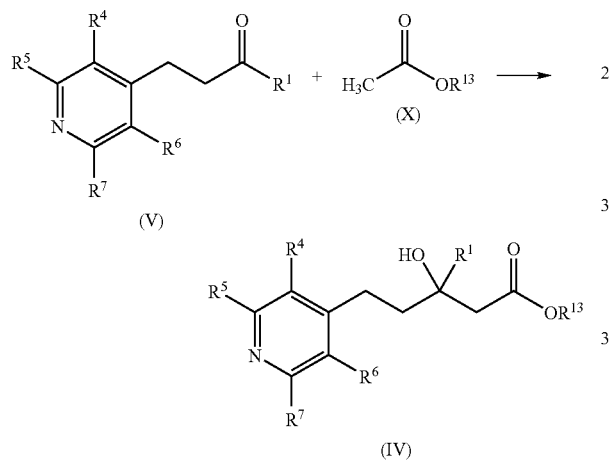

These reactions can be performed in the presence of strong base to first react with the compound of formula (X) to afford an anion. Suitable strong bases for such reactions include lithium hexamethyl disilylazide (LiHMDS), sodium hexamethyl disilazide, potassium hexamethyl disilazide, lithium diisopropyl amide, and magnesium diisopropylamide. Furthermore, such reactions can be performed in the presence of a solvent that will not interfere with the desired chemical reaction. Suitable solvents include, but are not limited to, neat solutions of the compound of formula (X), diethyl ether, methyl tert-butyl ether, and tetrahydrofuran. Additionally, such reactions can be performed at a temperature in the range of from about −78° C. to about 25° C., or in the range of from about −50° C. to about 25° C., or from about −35° C. to about 25° C., or in the range of from about −35° C. to about 0° C.

Alternatively, compounds of formula (IV) can be prepared by reaction of a compound of formula (V) with a silylketene acetal as shown below, wherein R is, for example, a $C_1$-$C_6$ alkyl group, and $R^{13}$ is as hereinbefore defined. These reactions can be performed in the presence of a catalytic or stoichiometric amount of a suitable Lewis acid that include, but are not limited to, aluminum (III) chloride, titanium (II) chloride, titanium (IV) chloride, tin (II) chloride, and tin (IV) chloride. Furthermore, such reactions can be performed in the presence of a solvent that will not interfere with the desired chemical reaction. Suitable solvents include, but are not limited to, diethyl ether, methyl tert-butyl ether, dichloromethane, dichloroethane, and tetrahydrofuran. Additionally, such reactions can be performed at a temperature in the range of from about −78° C. to about 25° C., or in the range of from about −50° C. to about 25° C., or from about −35° C. to about 25° C., or in the range of from about −35° C. to about 0° C.

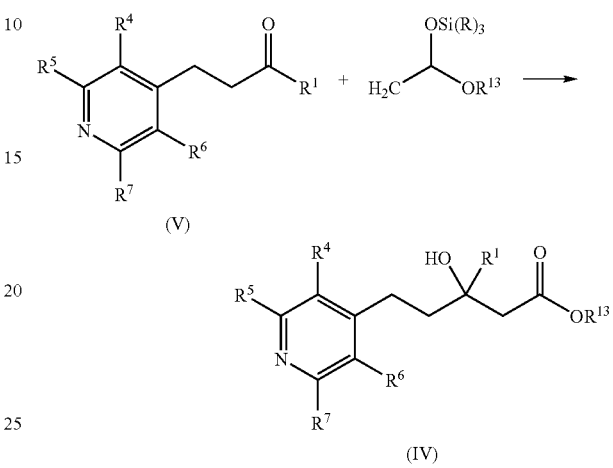

The compounds of formula (IV), wherein $R^1$, $R^4$, $R^5$, $R^6$, and $R^7$ are as hereinbefore defined, $P^1$ is hydrogen or a suitable protecting group, and $R^{13}$ is hydrogen can be resolved or stereoisomerically enriched. Such compounds can be stereoisomerically enriched by allowing them to react with a chiral, non-racemic base to form a mixture of diastereomeric salts. Such diastereomeric salts can then be separated using techniques well-known to those of ordinary skill in the art, such as fractional crystallization. For example, a mixture of the diastereomeric salts can be dissolved in a suitable solvent and one diastereomeric salt may then crystallize from the solution after which time it may be collected, washed and dried. Suitable chiral, non-racemic bases include amine bases include, but are not limited to, one enantiomer of cis-1-amino-2-indanol, cinchonidine, 1-aminoindane, tert-leucinol, 2-amino-1,2-diphenylethanol, alpha-methylbenzylamine, and 2-amino-1-(4-nitrophenyl)-1,3-propanediol. For example, a compound of formula (IV), wherein $R^1$, $R^4$, $R^5$, $R^6$, and $R^7$ are as hereinbefore defined, $P^1$ is hydrogen or a suitable protecting group, such as a trialkylsilyl ether, and $R^{13}$ is hydrogen, may be allowed to react with (1R,2R)-(−)-2-amino-1-(4-nitrophenyl)-1,3-propanediol in a suitable solvent, such as tetrahydrofuran to afford a mixture of diastereomeric salts. The solution containing the mixture of diastereomeric salts can then be allowed to slowly cool so that only one of the diastereomeric salts is appreciably soluble in the cooled solvent. The remaining diastereomeric salt may then precipitate out of the solution in the form of a crystalline solid comprising one diastereomeric salt in substantially pure form. The desired stereoisomerically enriched compound of formula (IV) may then be obtained from either the precipitated diastereomeric salt or from the diastereomeric salt that remained in solution. The compound of formula (IV), wherein $R^{13}$ is hydrogen, may then be obtained from the substantially pure diastereomeric salt by reaction with a suitable acidic compound, such as citric acid.

Compounds of formula (X), wherein $R^{13}$ is hydrogen, $C_1$-$C_6$ alkyl, —Si($C_1$-$C_6$ alkyl)$_3$, or —CH$_2$($C_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$, are either commercially available or can be prepared according to methods known to those of ordinary skill in the art.

Compounds of formula (V), wherein $R^1$, $R^4$, $R^5$, $R^6$, and $R^7$ are as hereinbefore defined, can be prepared from reaction of compounds of formula (VI), wherein $R^1$ is hereinbefore defined, with a compound of formula (VII), wherein $R^4$, $R^5$, $R^6$, and $R^7$ are as defined herein and X is a group suitable for use in a palladium-catalyzed (Pd-catalyzed) Heck-type coupling reaction. Heck-type coupling reactions can be performed using a palladium based catalyst. Suitable catalysts include, but are not limited to, Pd(Oac)$_2$, PdCl$_2$, and Pd(PPh$_3$)$_4$. Furthermore, such reactions can be performed in the presence of a base, such as triethylamine, sodium acetate, lithium acetate, potassium acetate, sodium carbonate, potassium carbonate, or cesium carbonate. These reactions may be performed in a solvent that will not interfere with the desired chemical reaction. Furthermore, appropriate solvents include those that are known to those of skill in the art to be compatible with the reaction conditions and include alkyl esters and aryl esters, alkyl, heterocyclic, and aryl ethers, hydrocarbons, alkyl and aryl alcohols, alkyl and aryl halogenated compounds, alkyl or aryl nitriles, alkyl and aryl ketones, amides, and non-protic heterocyclic solvents. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, N-methylpyrrolidinone, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Next, these reactions can be performed at a temperature in the range from about 0° C. to about 150° C., or in the range of from about 25° C. to about 150° C., or in the range of from about 25° C. to about 100° C., or in the range of from about 45° C. to about 100° C., or in the range of from about 45° C. to about 75° C. Last, in the compounds of formula (VII), X is a group that is suitable for use in Heck-type reactions. Suitable groups include chloride, bromide, iodide, and triflate (—OSO$_2$CF$_3$).

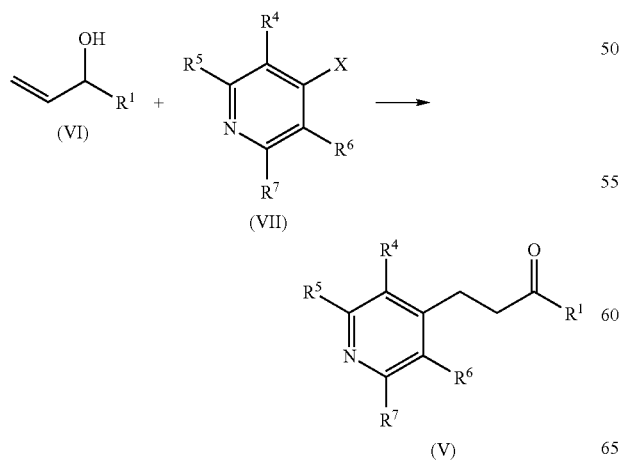

Compounds of formula (VII) are either commercially available or can be prepared by methods known to those of ordinary skill in the art.

Compounds of formula (VI), wherein $R^1$ is as hereinbefore defined, can be prepared by reaction of compounds of formula (X), wherein $R^1$ is as hereinbefore defined, and a compound of formula (XI),

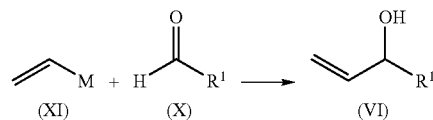

wherein M is a suitable metal, as shown. In the compounds of formula (XI), M is chosen from a suitable metal, such as a magnesium derivative, such as magnesium bromide, or lithium. These reactions can be performed in an aprotic solvent, such as diethyl ether, methyl tert-butyl ether, or tetrahydrofuran for example. Additionally, these reactions can be performed at a temperature in the range of from about −78° C. to about 50° C., or in the range of from about −78° C. to about 25° C., or in the range of from about −78° C. to about 0° C.

Compounds of formula (XI), wherein M is a suitable metal group, are either commercially available or can be prepared by methods known to those of ordinary skill in the art. For example, the compound of formula (XI) wherein M is —MgBr can be prepared from vinyl bromide and a suitable magnesium precursor, such as magnesium metal or activated Reike magnesium. These reactions are can be performed in an aprotic solvent such as diethyl ether, methyl tert-butyl ether, or tetrahydrofuran, and at a temperature in the range of from about 0° C. to about 25° C. Compounds of formula (XI) wherein M is Li can be prepared from vinyl halides, such as vinyl bromide or iodide and a suitable alkyl lithium reagent, such as butyl lithium or tert-butyl lithium. These reactions can be performed in an aprotic solvent such as diethyl ether, methyl tert-butyl ether, or tetrahydrofuran, and at a temperature in the range of from about 0° C. to about 25° C.

Compounds of formula (X), wherein $R^1$ is as hereinbefore defined, are either commercially available or can be prepared by reaction of a compound of formula (XII), wherein L is a suitable leaving group, with a compound of formula (XIII), $R^1$ is as hereinbefore defined and M is a suitable metal. In the compounds of formula (XII), L is a suitable leaving group, such a —N(CH$_3$)$_2$ group. In the compounds of formula (XIII), M is a suitable metal such as —MgBr or Li. These reactions are can be performed in an aprotic solvent such as diethyl ether, methyl tert-butyl ether, or tetrahydrofuran, and at a temperature in the range of from about 0° C. to about 25° C.

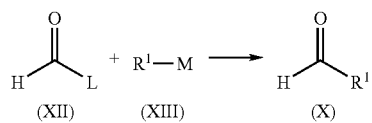

Compounds of formula (XII) are either commercially available or can be prepared by methods known to those of ordinary skill in the art.

Compounds of formula (XIII) wherein M is a suitable metal are either commercially available or can be prepared by methods known to those of ordinary skill in the art. For example, the compound of formula (XIII) wherein M is —MgBr can be prepared from vinyl bromide and a suitable magnesium precursor, such as magnesium metal or activated Rieke magnesium. These reactions are can be performed in an aprotic solvent such as diethyl ether, methyl tert-butyl ether, or tetrahydrofuran, and at a temperature in the range of from about 0° C. to about 25° C. Compounds of formula (XIII) wherein M is Li can be prepared from a suitable halide, such as a bromide or iodide and a suitable alkyl lithium reagent, such as butyl lithium or tert-butyl lithium. These reactions can be performed in an aprotic solvent such as diethyl ether, methyl tert-butyl ether, or tetrahydrofuran, and at a temperature in the range of from about 0° C. to about 25° C.

Compounds of formula (IX), such as (Ixa) below, are either commercially available or can be prepared using methods known to those of ordinary skill in the art. For example, the compound of formula (Ixa) was prepared by reaction of glycolic acid with aminoguanidine bicarbonate to afford (5-amino-1H-1,2,4-triazol-3-yl)methanol. The product was then allowed to react with 2,4-pentanedione to provide (5,7-dimethyl[1,2,4]triazolo[1,5-a]pyrimidin-2-yl)methanol, which was then oxidized using 2,2,6,6-tetramethyl-1-piperidinyloxy and iodobenzene diacetate to afford 5,7-dimethyl[1,2,4]triazolo[1,5-a]pyrimidine-2-carbaldehyde.

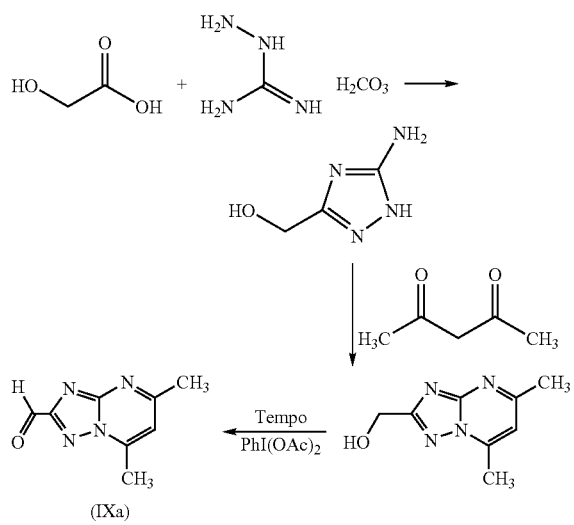

(IXa)

Administration of a crystalline form of (R)-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one, or a pharmaceutically acceptable salt thereof, may be performed according to any of the accepted modes of administration available to those skilled in the art. Illustrative Examples of suitable modes of administration include oral, nasal, parenteral, topical, transdermal, and rectal. Oral and intravenous deliveries are preferred.

A crystalline form of (R)-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one, or a pharmaceutically acceptable salt thereof, may be administered as a pharmaceutical composition in any suitable pharmaceutical form. Suitable pharmaceutical forms include solid, semisolid, liquid, or [ damantine[ formulations, such as tablets, powders, capsules, suppositories, suspensions, liposomes, and aerosols. The HCV-inhibiting agent may be prepared as a solution using any of a variety of methodologies. For Example, the HCV-inhibiting agent can be dissolved with acid (e.g., 1 M HCl) and diluted with a sufficient volume of a solution of 5% dextrose in water (D5W) to yield the desired final concentration of HCV-inhibiting agent (e.g., about 15 mM). Alternatively, a solution of D5W containing about 15 mM HCl can be used to provide a solution of the HCV-inhibiting agent at the appropriate concentration. Further, the HCV-inhibiting agent can be prepared as a suspension using, for example, a 1% solution of carboxymethylcellulose (CMC).

Acceptable methods of preparing suitable pharmaceutical forms of the pharmaceutical compositions are known or may be routinely determined by those skilled in the art. For Example, pharmaceutical preparations may be prepared following conventional techniques of the pharmaceutical chemist involving steps such as mixing, granulating, and compressing when necessary for tablet forms, or mixing, filling, and dissolving the ingredients as appropriate, to give the desired products for oral, parenteral, topical, intravaginal, intranasal, intrabronchial, intraocular, intraaural, and/or rectal administration.

Pharmaceutical compositions of the invention may also include suitable excipients, diluents, vehicles, and carriers, as well as other pharmaceutically active agents, depending upon the intended use. Solid or liquid pharmaceutically acceptable carriers, diluents, vehicles, or excipients may be employed in the pharmaceutical compositions. Illustrative solid carriers include starch, lactose, calcium sulfate damantin, terra alba, sucrose, talc, gelatin, pectin, acacia, magnesium stearate, and stearic acid. Illustrative liquid carriers include syrup, peanut oil, olive oil, saline solution, and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., solution), or a nonaqueous or aqueous liquid suspension.

A dose of the pharmaceutical composition may contain at least a therapeutically effective amount of an HCV-inhibiting agent and preferably is made up of one or more pharmaceutical dosage units. The selected dose may be administered to a mammal, for example, a human, in need of treatment mediated by inhibition of HCV activity, by any known or suitable method of administering the dose, including topically, for example, as an ointment or cream; orally; rectally, for example, as a suppository; parenterally by injection; intravenously; or continuously by intravaginal, intranasal, intrabronchial, intraaural, or intraocular infusion. When the composition is administered in conjunction with a cytotoxic drug, the composition can be administered before, with, and/or after introduction of the cytotoxic drug. However, when the composition is administered in conjunction with radiotherapy, the composition is preferably introduced before radiotherapy is commenced.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15$^{th}$ Ed. (1975).

It will be appreciated that the actual dosages of the HCV-inhibiting agent used in the pharmaceutical compositions of this invention will be selected according to the particular composition formulated, the mode of administration and the particular site, and the host and condition being treated. Optimal dosages for a given set of conditions can be ascertained by those skilled in the art using conventional dosage-determination tests. For oral administration, e.g., a dose that may be employed is from about 0.001 to about 1000 mg/kg body weight, or from about 0.1 to about 100 mg/kg body weight, or from about 1 to about 50 mg/kg body weight, or from about 0.1 to about 1 mg/kg body weight, with courses of treatment repeated at appropriate intervals. The dosage forms of the pharmaceutical formulations described herein may contain an amount of a crystalline form of ®-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one, or a pharmaceutically acceptable salt thereof, deemed appropriate by one of ordinary skill in the art. For example, such dosage forms may contain from about 1 mg to about 1500 mg of the compound, or a pharmaceutically acceptable salt thereof, or may contain from about 20 mg to about 1600 mg, or from about 5 mg to about 1500 mg, or from about 5 mg to about 1250 mg, or from about 10 mg to about 1250 mg, or from about 25 mg to about 1250 mg, or from about 25 mg to about 1000 mg, or from about 50 mg to about 1000 mg, or from about 50 mg to about 750 mg, or from about 75 mg to about 750 mg, or from about 100 mg to about 750 mg, or from about 125 mg to about 750 mg, or from about 150 mg to about 750 mg, or from about 150 mg to about 500 mg of the compound, or a pharmaceutically acceptable salt or solvate thereof.

The crystalline form of ®-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one, or a pharmaceutically acceptable salt thereof, may be applied as a sole therapy or may involve one or more other antiviral substances, for example those selected from, for example, HCV inhibitors such as interferon alphacon-1, natural interferon, interferon beta-1a, interferon omega, interferon gamma-1b, pegylated forms of IFN-α (Pegasys or PEG-INTRON), interleukin-10, BILN 2061 (serine protease), amantadine (Symmetrel), thymozine alpha-1, ribavirin, viramidine; HIV inhibitors such as nelfinavir, delavirdine, indinavir, nevirapine, saquinavir, and tenofovir. Such conjoint treatment may be achieved by way of the simultaneous, sequential or separate dosing of the individual components of the treatment.

While embodiments of the invention will been illustrated by reference to specific examples below, those skilled in the art will recognize that variations and modifications may be made to the examples through routine experimentation and practice of the invention. Thus, the invention is intended not to be limited by the following examples, but to be defined by the appended claims and their equivalents.

In the following examples, unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

EXAMPLES

In the examples described below, unless otherwise indicated, all temperatures in the following description are in degrees Celsius (° C.) and all parts and percentages are by weight, unless indicated otherwise.

Various starting materials and other reagents were purchased from commercial suppliers, such as Aldrich Chemical Company or Lancaster Synthesis Ltd., and used without further purification, unless otherwise indicated.

The reactions set forth below were performed under a positive pressure of nitrogen, argon or with a drying tube, at ambient temperature (unless otherwise stated), in anhydrous solvents. Analytical thin-layer chromatography was performed on glass-backed silica gel 60° F. 254 plates (Analtech (0.25 mm)) and eluted with the appropriate solvent ratios (v/v). The reactions were assayed by high-pressure liquid chromatography (HPLC) or thin-layer chromatography (TLC) and terminated as judged by the consumption of starting material. The TLC plates were visualized by UV, phosphomolybdic acid stain, or iodine stain.

$^1$H-NMR spectra were recorded on a Bruker instrument operating at 300 MHz and $^{13}$C-NMR spectra were recorded at 75 MHz. NMR spectra are obtained as DMSO-$d_6$ or CDCl$_3$ solutions (reported in ppm), using chloroform as the reference standard (7.25 ppm and 77.00 ppm) or DMSO-$d_6$ (2.50 ppm and 39.52 ppm). Other NMR solvents were used as needed. When peak multiplicities are reported, the following abbreviations are used: s=singlet, d=doublet, t=triplet, m=multiplet, br=broadened, dd=doublet of doublets, dt=doublet of triplets. Coupling constants, when given, are reported in Hertz.

Infrared spectra were recorded on a Perkin-Elmer FT-IR Spectrometer as neat oils, as KBr pellets, or as CDCl$_3$ solutions, and when reported are in wave numbers (cm$^{-1}$). The mass spectra were obtained using LC/MS with APCI or ESI ionization methods. All melting points are uncorrected.

In the following examples and preparations, "Et" means ethyl, "Ac" means acetyl, "Me" means methyl, "Ph" means phenyl, "HCl" means hydrochloric acid, "EtOAc" means ethyl acetate, "Na$_2$CO$_3$" means sodium carbonate, "NaOH" means sodium hydroxide, "NaCl" means sodium chloride, "Net$_3$" means triethylamine, "THF" means tetrahydrofuran, "H$_2$O" means water, "NaHCO$_3$" means sodium hydrogen carbonate, "K$_2$CO$_3$" means potassium carbonate, "MeOH" means methanol, "i-PrOAc" means isopropyl acetate, "MgSO$_4$" means magnesium sulfate, "DMSO" means dimethylsulfoxide, "CH$_2$Cl$_2$" means methylene chloride, "MTBE" means methyl t-butyl ether, "DMF" means dimethyl formamide, "CH$_3$CN" means acetonitrile, "KOH" means potassium hydroxide, "CDI" means carbonyl diimidazole, "DABCO" means 1,4-diazabicyclo[2.2.2]octane, "IPE" means isopropyl ether, "MTBE" means methyl tert-butyl ether, "L-DBTA" means dibenzoyl-L-tartaric acid, "IPAC" means isopropyl acetate, "h" means hours, "min" means minutes, "mol" means moles, and "rt" means room temperature.

Example 1

Preparation of the glycolate salt of (5-amino-1H-1,2,4-triazol-3-yl)methanol

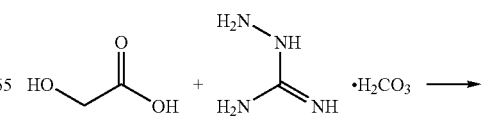

-continued

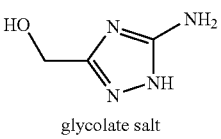

glycolate salt

Glycolic acid (1 L, 70% in water, 11.51 mol) was added to a 5 L flask. To the solution was slowly added aminoguanidine bicarbonate (783.33 g, 5.755 mol) in portions to control significant bubbling. As solids are added, the solution cools due to endothermic dissolution. The solution was gently heated to maintain an internal temp of 25° C. during addition. Ten minutes after complete addition of aminoguanidine bicarbonate, conc. Nitric acid (6.8 mL) was carefully added. The solution was heated to an internal temperature of 104-108° C. (mild reflux) for 22 h. The heating was discontinued and the solution allowed to cool, with stirring. At an internal temp of about 81° C., solids began to crystallize. After the internal temperature was just below 80° C., ethanol (absolute, 375 mL) was slowly added to the mixture. After the internal temp had cooled to about 68° C., the cooling was sped up by the use of an ice/water bath. After cooling below rt, the solution became very thick but remained stirrable at all times. The slurry was stirred for 2 h at T<10° C., then filtered and the solids rinsed with ethanol (900 mL cold, then 250 mL rt). The solids were dried overnight in a vacuum oven (about 25 mmHg, 45-50° C.) to provide 815.80 g (75%) of (5-amino-1H-1,2,4-triazol-3-yl)methanol as the glycolate salt. $^1$H (300 MHz, $d_6$-DMSO): 3.90 (s, 2), 4.24 (s, 2).

Example 2

Preparation of (5,7-dimethyl[1,2,4]triazolo[1,5-a]pyrimidin-2-yl)methanol

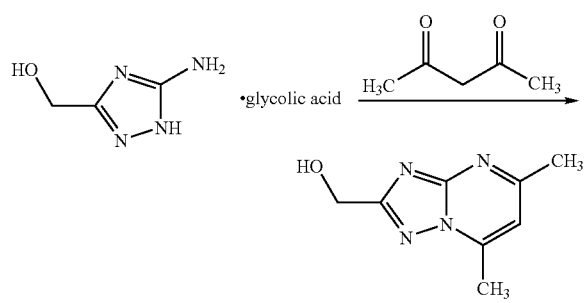

To a 2 L, 3-neck flask was charged glycolate salt of (5-amino-1H-1,2,4-triazol-3-yl)methanol (99.93 g, 0.526 mol), 2,4 pentanedione (0.578 mols, 60 mL), acetic acid (6.70 mL), and EtOH (550 mL). The mixture was heated to a slight reflux. One hour after adding the reagents, the resulting solution was cooled to ambient temperature, and $CH_2Cl_2$ (500 mL) and Celite (25.03 g) were added. After stirring for 1 h, the mixture was filtered through a 4" Buchner funnel packed with celite (20 g) and rinsed with EtOH (100 mL). The solution was distilled to 5 vols then cooled to 0° C. for 1-2 hours. The slurry was filtered and the cake was rinsed with cold EtOH (2×100 mL). The solids were dried to provide 76.67 g (81.7%) of the title compound.

$^1$H NMR (300 MHz, $d_6$-DMSO): 2.57 (s, 3), 2.71 (d, 3, J=0.8), 4.63 (uneven d, 2, J=5.7), 5.49 (t, 1, J=6.2), 7.13 (d, 1, J=0.8).

Example 3

Preparation of 5,7-dimethyl[1,2,4]triazolo[1,5-a]pyrimidine-2-carbaldehyde

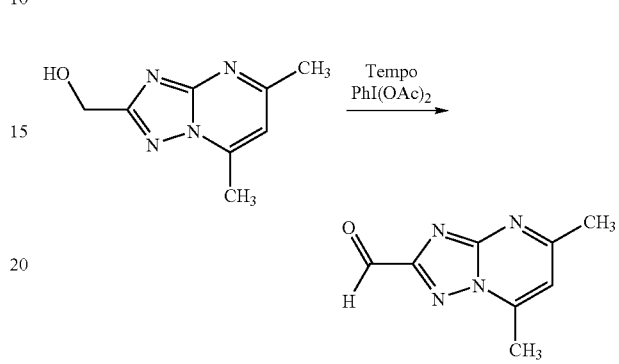

To a 10 L reactor was sequentially charged $CH_2Cl_2$ (5.1 L), (5,7-dimethyl[1,2,4]triazolo[1,5-a]pyrimidin-2-yl)methanol (680 g, 3.816 mol), and iodobenzene diacetate (1352 g, 4.197 mol). As the iodobenzene diacetate dissolves, there is a significant endotherm (typically down to 15-16° C.). The jacket was set to 23° C. The mixture was warmed to ambient temperature and Tempo (2,2,6,6-tetramethyl-1-piperidinyloxy, free radical, 43.75 g, 0.28 mol) added in a single charge. The reaction was stirred until 5% of the starting alcohol remained by HPLC. Once the starting material is adjudged to be less than about 5%, the over-oxidized product begins to be observed. Allowing the reaction to run to further completion leads to an overall diminished yield of the desired product. For this reaction, the desired reaction completion was reached in 2.75 h. MTBE (5.1 L) was then slowly charged to the reactor, causing the product to precipitate, and the slurry stirred for an additional 30 mins. The mixture was filtered, washed twice with 1:1 DCM/MTBE (2×1 L), and dried in a vacuum oven overnight at 50° C. to provide 500.3 g (74%) of 5,7-dimethyl[1,2,4]triazolo[1,5-a]pyrimidine-2-carbaldehyde as an off-white solid. $^1$H NMR (300 MHz, $d_6$-DMSO): 2.64 (s, 3), 2.78 (d, 3, J=0.8), 7.36 (d, 1, J=0.9), 10.13 (s, 1).

Example 4

Preparation of the dibenzoyl-L-tartaric acid salt of 1-cyclopentyl-3-(2,6-diethylpyridin-4-yl)propan-1-one

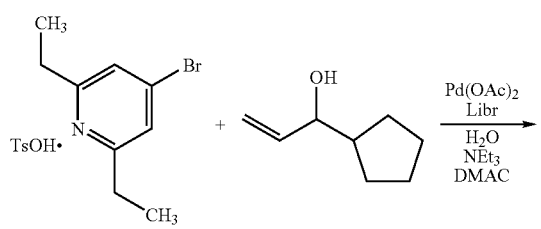

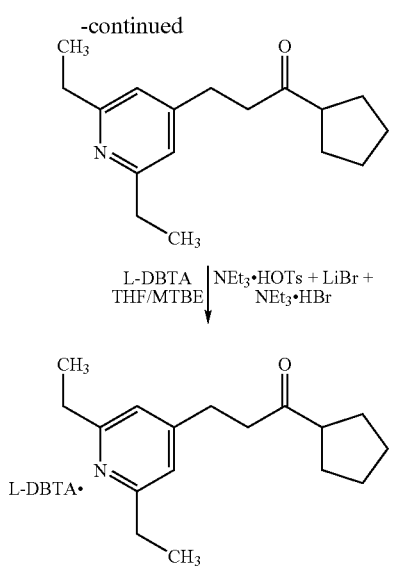

A nitrogen-purged, 5-L, 3-neck flask containing 4-bromo-2,6-diethylpyridine (250.0 g, 0.6472 mol) was sequentially charged with LiBr (112.42 g, 1.2944 mol), 1-cyclopentyl-prop-2-en-1-ol (89.84 g, 0.7119 mol), DMAc (625 mL), and H₂O (55.0 mL). The mixture was cooled to 5-10° C. and was then purged (subsurface) with N₂ for 30 minutes. The flask was charged with Et₃N (198.5 mL, 1.4242 mol) and Pd(Oac)₂ (3.63 g, 0.0162 mol), followed by a careful purge of the headspace. The reaction was heated until the internal temperature reached 95° C. After stirring at 95° C. for three hours, an aliquot was removed and analyzed by HPLC, showing >99% conversion to 1-cyclopentyl-3-(2,6-diethylpyridin-4-yl)propan-1-one. The reaction was then cooled to 30° C. over 20 min. The flask was charged with H₂O (1500 mL), and MTBE (1500 mL). The solution was stirred well for 5 minutes before the mixture was allowed to settle and the aqueous layer was removed. To the organic layer was charged Celite (62.50 g), and Darco G-60 (6.25 g). The slurry was stirred for 20 minutes at 20-25° C. The slurry was then filtered using a Buchner funnel dressed with Celite. The filter cake was rinsed with MTBE (250 mL). The organic layer was extracted with 5% sodium bicarbonate solution (500 mL) and the phases separated. The organic layer was transferred to a 5 L, three-neck flask, and MTBE added to achieve a total reaction volume of 1750 mL. Additional MTBE (1500 mL) was added and atmospherically distilled until an internal volume of 1750 mL was reached. After cooling below 40° C., a sample was removed for analysis of water content. After cooling to 20-25° C., MTBE (250 mL) was added to bring the total volume to 2000 mL and the solution was seeded with crystals of the dibenzoyl-L-tartaric acid salt of 1-cyclopentyl-3-(2,6-diethylpyridin-4-yl)propan-1-one (130 mg), which were prepared according to this procedure. A solution of dibenzoyl-L-tartaric acid (231.89 g, 0.6472 mol) in THF (900 mL) was added over 25 minutes. The slurry was granulated for 1 hour, the mixture was filtered, and the cake rinsed with MTBE (450 mL). The solids were dried in a vacuum oven at 50° C. for 12 h to provide 366.70 g (92% yield) of the title compound. ¹H NMR (300 MHz, d₆-DMSO): 1.19 (t, 6, J=7.6), 1.47-1.81 (m, 8), 2.73 (q, 4, J=7.6), 2.73-2.98 (m, 5), 5.86 (s, 2), 7.00 (s, 2), 7.55-7.63 (m, 4), 7.68-7.75 (m, 2), 7.98-8.04 (m, 4).

Example 5

Preparation of 3-cyclopentyl-5-(2,6-diethylpyridin-4-yl)-3-hydroxypentanoic acid

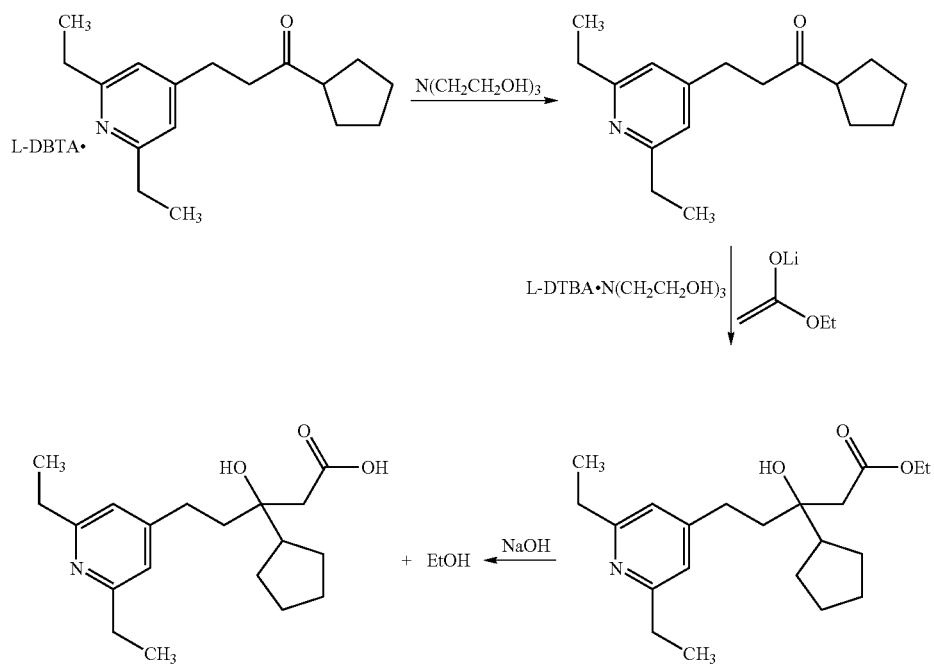

A 3-L, 3-neck flask was charged with the dibenzoyl-L-tartaric acid salt of 1-cyclopentyl-3-(2,6-diethylpyridin-4-yl)propan-1-one (174.95 g, 0.2832 mol), MTBE (875 mL), water (875 mL), and triethanolamine (113.0 mL, 0.8513 mol). After stirring for 2 h at rt, an aliquot of the aqueous phase was removed and analyzed by HPLC, showing no detectable starting material. The solution was transferred to a separatory funnel and the layers separated. The lower aqueous phase was discarded and the upper org. phase was washed with water (150 mL). The organic layer was added to a flask set up for distillation. The solution was distilled down to approx. 183 mL and an aliquot was removed and analyzed for water content. The dry solution of 1-cyclopentyl-3-(2,6-diethylpyridin-4-yl)propan-1-one (th. Wt=73.47 g) in MTBE was used directly in the next step.

A clean 2-L, 3-neck flask was charged with LiHMDS (1.0 M in THF, 355 mL, 0.355 mol) and purged with nitrogen. The flask was cooled to −34° C. An addition funnel was then charged with EtOAc (35 mL, 0.3583 mol) and this reagent was slowly added to the reaction vessel at such a rate that the low temperature of the vessel could be maintained. After complete EtOAc addition another addition funnel was charged with the 1-cyclopentyl-3-(2,6-diethylpyridin-4-yl)propan-1-one solution (crude MTBE soln from prior reaction, theor. 73.47 g, 0.2832 mol) and rinsed over with THF (anhydrous, 5 mL). The 1-cyclopentyl-3-(2,6-diethylpyridin-4-yl)propan-1-one solution was slowly added to the reaction flask at such a rate that the low internal temperature could be maintained. Five minutes after complete addition, a reaction aliquot was removed and analyzed by HPLC, showing less than 1% 1-cyclopentyl-3-(2,6-diethylpyridin-4-yl)propan-1-one. Ten minutes after complete ketone addition, the bath was switched to 0° C. Once the internal temperature had warmed to −10° C., 1M NaOH (510 mL) was added. After complete NaOH soln addition, the reaction was heated to 50° C. After 21 hours the reaction solution was cooled below 30° C. and an aliquot of both layers was removed and analyzed for completion. The mixture was added to a separatory funnel with MTBE (350 mL) and the phases were mixed well and separated. An aliquot of the organic phase was analyzed by HPLC, verifying no significant product, and this layer was discarded. The aqueous phase was added to a flask with CH$_2$Cl$_2$ (350 mL). Concentrated aqueous HCl (about 100 mL) was slowly added to the aqueous phase until the pH=5. The mixture was added back to a separatory funnel and mixed well. The phases were separated and the aqueous layer was extracted a second time with CH$_2$Cl$_2$ (150 mL). The organic layers were combined and charged to a clean flask set up for distillation. The solution was distilled down to 370 mL then displaced with THF by addition of solvent portions followed by continued distillation down to 370 mL after each addition. When the distillation head temp. held steady at 65° C. for 30 min an aliquot was removed and analyzed by $^1$H NMR, showing a 12.5:1 ratio of THF:CH$_2$Cl$_2$. The solution of 3-cyclopentyl-5-(2,6-diethylpyridin-4-yl)-3-hydroxypentanoic acid in THF was used directly in the next step.

Example 6a

Preparation of the (1R,2R)-(−)-2-amino-1-(4-nitrophenyl)-1,3-propanediol salt of (R)-3-cyclopentyl-5-(2,6-diethylpyridin-4- yl)-3-hydroxypentanoic acid

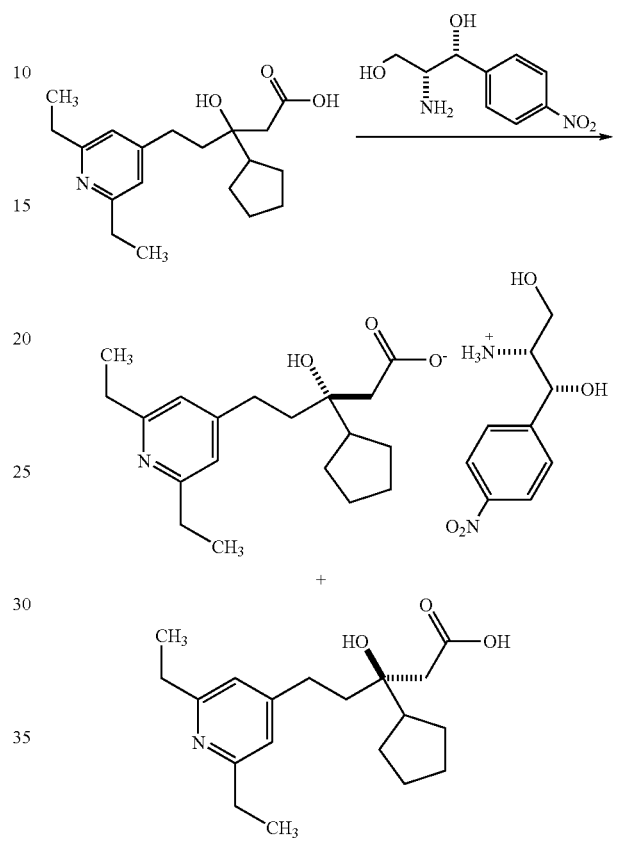

A 2-L, 3-neck flask was sequentially charged with a solution of 3-cyclopentyl-5-(2,6-diethylpyridin-4-yl)-3-hydroxypentanoic acid (crude from last step, theoretical 95.28 g, 0.1792 mol, in about 300 mL), (1R,2R)-(−)-2-amino-1-(4-nitrophenyl)-1,3-propanediol (38.03 g, 0.1792 moles) and THF (415 mL). A seed crystal of the (1R,2R)-(−)-2-amino-1-(4-nitrophenyl)-1,3-propanediol salt of (R)-3-cyclopentyl-5-(2,6-diethylpyridin-4-yl)-3-hydroxypentanoic acid, prepared according to this procedure, was added and the mixture was stirred and heated to 65° C., then held at this temperature for 16 h. The slurry was cooled slowly to rt and stirred for at least 1 h. The slurry was filtered and the cake rinsed with THF (100 mL). The filtrate (solution of (S)-3-cyclopentyl-5-(2,6-diethylpyridin-4-yl)-3-hydroxypentanoic acid in THF) was used directly in the next procedure. The solids were dried to provide 67.09 g (42%) of the (1R,2R)-(−)-2-amino-1-(4-nitrophenyl)-1,3-propanediol salt of (R)-3-cyclopentyl-5-(2,6-diethylpyridin-4-yl)-3-hydroxypentanoic acid as an off-white crystalline solid. Chiral HPLC analysis of the product showed a 92.1:7.9 ratio of the (1R,2R)-(−)-2-amino-1-(4-nitrophenyl)-1,3-propanediol salt of &3-cyclopentyl-5-(2,6-diethylpyridin-4-yl)-3-hydroxypentanoic acid to (S)-3-cyclopentyl-5-(2,6-diethylpyridin-4-yl)-3-hydroxypentanoic acid.

HPLC conditions: The solid was dissolved in methanol. HPLC conditions: Chirobiotic TAG column, 4.6×250 mm, 40° C. column chamber, flow rate=0.5 mL/min, mobile phase=100% MeOH (0.05% TEA, 0.05% HOAc). Gradient: Initial flow rate=0.5 mL/min; 10 min flow rate=0.5 mL/min; 10.10 min flow rate=2.00 mL/min; 35 min flow rate=2.00 mL/min; 36 min flow rate=0.5 mL/min. Percentages reported are at 265 nm. Retention times: (1R,2R)-(−)-2-amino-1-(4-nitrophenyl)-1,3-propanediol=>30 min; (S)-3-cyclopentyl-5-(2,6-diethylpyridin-4-yl)-3-hydroxypentanoic acid=5.8 min; ®-3-cyclopentyl-5-(2,6-diethylpyridin-4-yl)-3-hydroxypentanoic acid=7.2 min. $^1$H NMR (300 MHz, $d_6$-DMSO): 1.19 (t, 6, J=7.6), 1.38-1.62 (m, 8), 1.65-1.75 (m, 2), 1.93-2.07 (m, 1), 2.23 (d, 1, J=14.4), 2.31 (d, 1, J=14.4), 2.56 (m, 2), 2.64 (q, 4, J=7.6), 2.91-2.99 (m, 1), 3.22 (dd, 1, J=5.8, 11.1), 3.42 (dd, 1, J=4.8, 11.1), 4.77 (d, 1, J=6.2), 6.0 (br s, 6), 6.84 (s, 2), 7.62 (d, 2, J=8.7), 8.20 (d, 2, J=8.8).

Example 6b

Recrystallization of the (1R,2R)-(−)-2-amino-1-(4-nitrophenyl)-1,3-propanediol salt of ®-3-cyclopentyl-5-(2,6-diethylpyridin-4-yl)-3-hydroxypentanoic acid A 2-L, 3-neck flask was charged with the (1R,2R)-(−)-2-amino-1-(4-nitrophenyl)-1,3-propanediol salt of ®-3-cyclopentyl-5-(2,6-diethylpyridin-4-yl)-3-hydroxypentanoic acid (66.20 g, 0.1245 moles) and 2 B EtOH (970 mL absolute EtOH+5 mL toluene). The slurry was stirred and heated to reflux. After holding at reflux for 40 min, all the solids had dissolved and the solution was cooled to an internal temp of about 65° C. over 30 min, and the solution was then seeded with crystals of the title compound. The solution was allowed to cool to 50° C. and held for an additional 2 h. The solution was then cooled slowly to room temperature over about 2 hours. The cooled solution was stirred at rt for an additional 10 h. The mixture was then filtered and the solids rinsed with 2 B EtOH (75 mL). The solids were dried to provide 52.72 g (80%) of product as an off-white crystalline solid that was then dried under vacuum (30 mm Hg) with a nitrogen bleed at 50° C. for 12 h. Chiral HPLC analysis showed product with 96% ee. For determination of e.e., the solid was dissolved in MeOH. HPLC conditions: Chirobiotic TAG column, 4.6×250 mm, 40° C. column chamber, flow rate=0.5 mL/min, 100% MeOH (0.05% TEA, 0.05% HOAc). Gradient: Initial flow rate=0.5 mL/min; 10 min flow rate=0.5 mL/min; 10.10 min flow rate=2.00 mL/min; 35 min flow rate=2.00 mL/min; 36 min flow rate=0.5 mL/min. Percentages reported are at 265 nm. Retention times: (1R,2R)-(−)-2-amino-1-(4-nitrophenyl)-1,3-propanediol=>30 min, (S)-3-cyclopentyl-5-(2,6-diethylpyridin-4-yl)-3-hydroxypentanoic acid=5.8 min, ®-3- cyclopentyl-5-(2,6-diethylpyridin-4-yl)-3-hydroxypentanoic acid=7.2 min.

Example 7

Preparation of 1-cyclopentyl-3-(2,6-diethylpyridin-4-yl)propan-1-one from (S)-3-cyclopentyl-5-(2,6-diethylpyridin-4-yl)-3-hydroxypentanoic acid

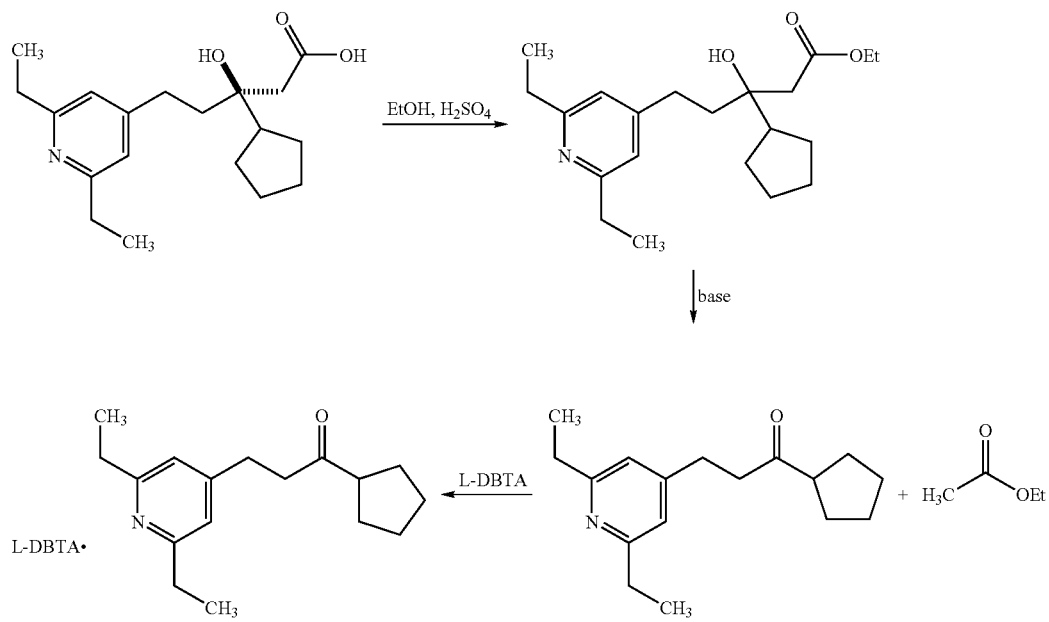

A flask was charged with a solution of (S)-3-cyclopentyl-5-(2,6-diethylpyridin-4-yl)-3-hydroxypentanoic acid (crude from last step, theoretical 15 g, 0.0470 mol, in about 200 mL THF) and ethanol (100 mL, 1.7126 mol). To the solution, $H_2SO_4$ (5.0 mL, 0.0938 mol) was added slowly. The solution was heated at reflux for 18 h. When the reaction was judged to be complete by HPLC, the solution was cooled and added to a separatory funnel with 0.5M NaOH (400 mL) and then extracted with MTBE (200 mL). The phases were separated and the organic layer was washed with aqueous acetic acid $H_2O$ (100 mL $H_2O$+3.0 mL HOAc). The phases were separated and the organic layer was washed with 0.5 M NaOH (100 mL). The phases were separated and the organic layer was washed with saturated aqueous NaCl solution (25 mL). The organic layer was distilled at atmospheric pressure down to an internal volume of 150 mL. The solvent was displaced by toluene via atmospheric distillation by adding toluene (100 mL), distilling down to 200 mL internal volume, and repeating this procedure two more times. The final solution was distilled down to an internal volume of 130 mL. An aliquot was removed and analyzed by KF titration. The solution was cooled to rt and a solution of KotBu (1.0M in THF, 4.7 mL, 0.0047 mol) was added in one portion. After 5 min, an aliquot was removed and analyzed by HPLC. The solution was added to a separatory funnel with 1M HCl (60 mL). The phases were mixed well and separated, transferring the product to the aqueous phase. The organic phase was extracted once with water (10 mL) and the aqueous phases combined. The organic phase was discarded. To the aqueous phase was added MTBE (60 mL) and 1M NaOH (70 mL) and the phases mixed well. The phases were separated and the organic phase extracted with saturated aqueous NaCl solution (25 mL). MTBE was added to bring the volume up to 125 mL. The solution was cooled to rt and seeded with crystals of the dibenzoyl-L-tartaric acid salt of 1-cyclopentyl-3-(2,6-diethylpyridin-4-yl)propan-1-one (prepared according to Example 4). In a separate vessel, L-DBTA (16.89 g, 0.0471 mol) was dissolved in THF (65 mL). The solution of L-DBTA was added to the 1-cyclopentyl-3-(2,6-diethylpyridin-4-yl)propan-1-one solution over 45 min, and the slurry granulated for 1 h. The slurry was filtered and the cake washed with MTBE (50 mL). The solids were dried to provide 19.54 g of the dibenzoyl-L-tartaric acid salt of 1-cyclopentyl-3-(2,6-diethylpyridin-4-yl)propan-1-one (67%) as an off-white solid.

Example 8a

Preparation of the dibenzoyl-L-tartaric acid salt of (R)-6-cyclopentyl-6-(2-(2,6-diethylpyridin-4-yl)ethyl)-4-hydroxy-5,6-dihydropyran-2-one

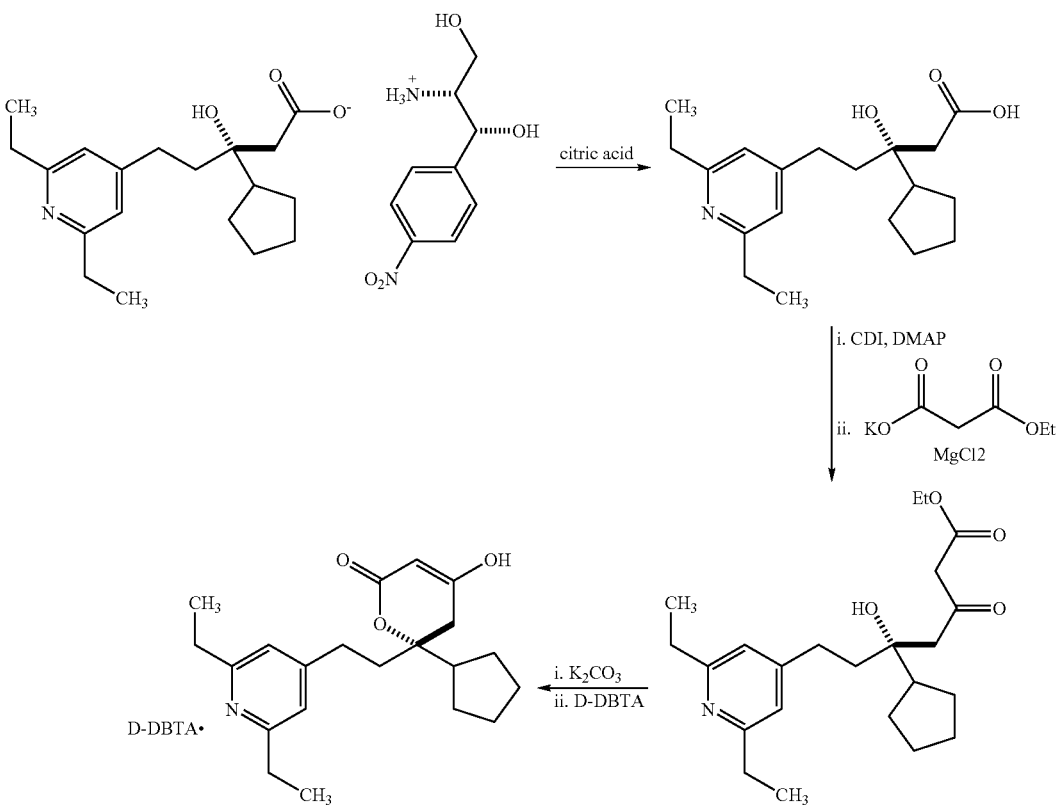

A nitrogen-purged flask containing the (1R,2R)-(−)-2-amino-1-(4-nitrophenyl)-1,3-propanediol salt of (R)-3-cyclopentyl-5-(2,6-diethylpyridin-4-yl)-3-hydroxypentanoic acid (20.00 g, 0.0376 mol) was charged with $CH_2Cl_2$ (200 mL) and $H_2O$ (100 mL). The pH of the mixture was adjusted to pH 4.75 with 40% aqueous citric acid (10 mL) and was stirred for 60 minutes. The layers were allowed to settle for 30 minutes and separated. The upper (aqueous) layer was charged $CH_2Cl_2$ (50 mL), stirred 15 minutes, and was then allowed to settle. The organic layer was combined with the first organic layer and dried with sodium sulfate. The dried organic was concentrated under reduced pressure. The (R)-3-cyclopentyl-5-(2,6-diethylpyridin-4-yl)-3-hydroxypentanoic acid residue was dissolved in THF (47 mL) and this solution added to a slurry of carbonyl diimidazole (9.00 g, 0.0555 mol) and 4-N,N-dimethylaminopyridine (DMAP, 0.45 g, 0.0037 mol) in THF (106 mL) over 5 minutes. Upon complete acyl-imidazole formation, the solution was added to a slurry of potassium ethyl malonate (12.57 g, 0.0738 mol) and magnesium chloride (7.38 g, 0.0775 mol) in 106 mL THF over 5 minutes. The slurry was allowed to stir at 20-25° C. for 30 hours. An aliquot was removed and analyzed by HPLC, showing 96% conversion to ®-ethyl 5-cyclopentyl-7-(2,6-diethylpyridin-4-yl)-5-hydroxy-3-oxoheptanoate. The flask was charged with $H_2O$ (64 mL), and MTBE (118 mL). The mixture was stirred well for 5 minutes before it was allowed to settle and the aqueous (lower) layer was removed. To the organic layer was charged brine (52 mL). The mixture was stirred well for 5 minutes before it was allowed to settle and the aqueous (lower) layer was removed. The organic layer was then displaced via atmospheric distillation with methanol (2×210 mL) until a total volume of 140 mL was achieved. MTBE (105 mL) was added followed by powdered potassium carbonate (7.65 g, 0.0554 mol), and the slurry heated to reflux for 12 hours. After cooling to 40° C., MTBE (140 mL) and water (140 mL) were added. The mixture was stirred well for 5 minutes before it was allowed to settle and the aqueous (lower) layer was isolated. The organic layer was extracted with water (30 mL) and the aqueous layers were combined. $CH_2Cl_2$ (140 mL) was added to the aqueous layer and the pH adjusted to 6.4 with 40% aqueous citric acid (29 mL). The aqueous layer was extracted a second time with $CH_2Cl_2$ (25 mL). The combined organic layers were then displaced fully into MTBE (140 mL final volume) via atmospheric distillation, cooled, and added slowly to a solution of dibenzoyl-D-tartaric acid (9.92 g, 0.0277 mol) in MTBE (100 mL). The slurry was heated to reflux for 1 hour, then allowed to cool to 20-25° C. The mixture was filtered, and the cake rinsed with MTBE (50 mL). The solids were dried in a vacuum oven at 50° C. for 12 h to provide 16.40 g (62%) of the title compound.

Example 8b

Preparation of the dibenzoyl-L-tartaric acid salt of ®-6-cyclopentyl-6-(2-(2,6-diethylpyridin-4-yl)ethyl)-4-hydroxy-5,6-dihydropyran-2-one A nitrogen-purged flask containing the (1R,2R)-(−)-2-amino-1-(4-nitrophenyl)-1,3-propanediol salt of ®-3-cyclopentyl-5-(2,6-diethylpyridin-4-yl)-3-hydroxypentanoic acid (50.00 g, 0.0940 mol) was charged with $CH_2Cl_2$ (500 mL) and $H_2O$ (250 mL). The pH of the resulting suspension was adjusted to pH 4.6 to 4.8 (a measured pH of 4.75 is preferred) with 40% aqueous citric acid (21 mL) and was stirred for 30 minutes. The layers were allowed to settle for 30 minutes and separated. The upper (aqueous) layer was charged with $CH_2Cl_2$ (100 mL), stirred 15 minutes, and allowed to settle. The organic layer was combined with the first organic layer. The upper (aqueous) layer was again charged with $CH_2Cl_2$ (100 mL), stirred 15 minutes, and allowed to settle. This organic layer was also combined with the first organic layer. A sample of each of the combined organic layers and the aqueous layer was taken for HPLC analysis. The combined organic layers were atmospherically distilled until a total volume of 120 mL was reached. THF (100 mL) was charged and atmospheric distillation continued until a total volume of 120 mL was reached. The THF charge and displacement was repeated 3 times. A sample was removed and analyzed by NMR and KF. The resulting solution was added to a slurry of CDI (22.86 g, 0.1410 mol) and DMAP (1.15 g, 0.0094 mol) in THF (250 mL) over 15 minutes. The addition funnel was then rinsed with 10 mL THF which was then added to the CDI slurry. After stirring 15 minutes, a sample was removed and analyzed by HPLC. Upon complete acyl-imidazole formation, the solution was added to a slurry of potassium ethyl malonate (32.00 g, 0.1880 mol) and magnesium chloride (18.80 g, 0.1974 mol) in 250 mL THF at 20-25° C. over 25 minutes. The slurry was allowed to stir at 20-25° C. for 21 hours. An aliquot was removed and analyzed by HPLC, showing 96% conversion to ®-ethyl 5-cyclopentyl-7-(2,6-diethylpyridin-4-yl)-5-hydroxy-3-oxoheptanoate. The flask was charged with $H_2O$ (162 mL), and MTBE (300 mL). The mixture was stirred well for 5 minutes before it was allowed to settle and the yellow aqueous (lower) layer was removed. To the organic layer was charged brine (100 mL). The mixture was stirred well for 5 minutes before it was allowed to settle and the aqueous (lower) layer was removed. The organic layer was then atmospherically distilled down to 350 mL total volume. MTBE (250 mL) was charged and the solution distilled to 350 mL total volume. Additional MTBE (250 mL) was charged and the solution distilled at a temperature of at least 55° C. to 350 mL total volume. A sample was removed for KF titration. Methanol (250 mL) was charged and the solution was then atmospherically distilled until a total volume of 350 mL was achieved. Methanol (250 mL) was charged and then the solution was atmospherically distilled until a total volume of 350 mL was achieved and a temperature of ~66° C. was achieved. Powdered potassium carbonate (19.49 g, 0.1410 mol) was added and the slurry heated to reflux for 4 hours. A sample was removed for HPLC analysis showing >99% completion. After cooling to 22° C., MTBE (350 mL) and water (350 mL) were added. The mixture was stirred well for 5 minutes before it was allowed to settle and the product rich aqueous (lower) layer was isolated. The organic layer was extracted with water (100 mL) and the aqueous layers were combined. To the combined aqueous layers was charged MTBE (100 mL). The mixture was stirred well for 5 minutes before it was allowed to settle and the product rich aqueous (lower) layer was isolated. $CH_2Cl_2$ (350 mL) was added to the aqueous layer and the pH adjusted to 6.0-6.4 with 40% aqueous citric acid (75 mL). The aqueous layer was extracted a second time with $CH_2Cl_2$ (100 mL). The combined organic layers were then atmospherically distilled to 250 mL total volume. MTBE (400 mL) was charged and the solution was atmospherically distilled at a temperature of at least 55° C. until 250 mL final volume was reached. After cooling the solution to 20-25° C., a prepared solution of dibenzoyl-D-tartaric acid (23.58 g, 0.0658 mol) in MTBE (125 mL) was added over 10 minutes. The resulting slurry was heated to reflux for 4 hours, then allowed to cool to 20-25° C. and stirred an additional 4 hours. The slurry was filtered, and the cake rinsed with MTBE (125 mL). The solids were dried in a vacuum oven at 50° C. for 12 h to provide 38.19 g (58%) of the title compound. HPLC conditions: aliquots were withdrawn and dissolved in $CH_3CN/H_2O$ (40:60). HPLC conditions: Kromasil C4 column, 5 μm, 4.6×150 mm, 40° C. column chamber, flow rate=1.0 mL/min, 40% $CH_3CN$/60% aqueous (1.0 mL 70% $HClO_4$ in 1 L $H_2O$) isocratic. Percentages reported are at 254 nm. Approximate retention times: ®-3-cyclopentyl-5-(2,6-diethylpyridin-4-yl)-3-hydroxypentanoic acid=3.4 min; methyl 5-cyclopentyl-7-(2,6-diethylpyridin-4-yl)-5-hydroxy-3-oxoheptanoate=7.3 min; ®-6-cyclopentyl-6-(2-

(2,6-diethylpyridin-4-yl)ethyl)-4-hydroxy-5,6-dihydropyran-2-one=3.9 min; D-DBTA=5.5 min.

Example 9a

Preparation of (R)-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one

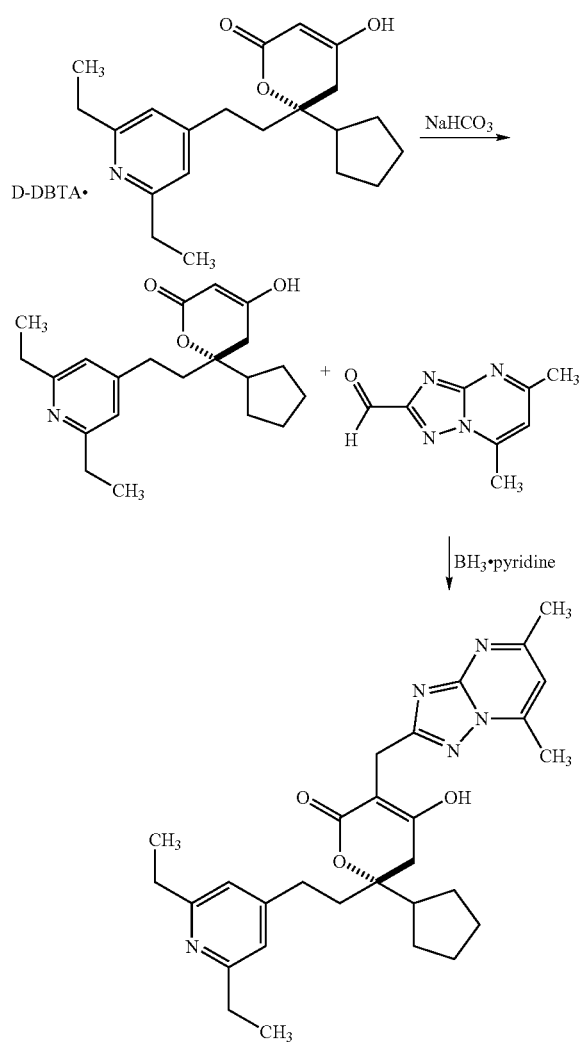

A flask was charged with the dibenzoyl-L-tartaric acid salt of (R)-6-cyclopentyl-6-(2-(2,6-diethylpyridin-4-yl)ethyl)-4-hydroxy-5,6-dihydropyran-2-one (this material contained 1.5 eq DBTA counterion, 4.00 g, theor. 0.00454 mol), 2-MeTHF (40 mL), MTBE (40 mL), and water (20 mL). A solution of 5% aq NaHCO₃ (about 20 mL) was added until the pH was 7.4. The solution pH was back-adjusted to pH=7.2 with a small amount of 40% citric acid solution. The phases were separated and the aqueous layer was extracted with 2-MeTHF (25 mL). The combined organic layers were dried with $Na_2SO_4$ and concentrated to an oil. The oil was used directly in the subsequent condensation. To the crude (R)-6-cyclopentyl-6-(2-(2,6-diethylpyridin-4-yl) ethyl)-4-hydroxy-5,6-dihydropyran-2-one was added methanol (32 mL) and the solution cooled to −40° C. To the cold solution was added pyridine-borane complex (1.30 mL, 0.01287 mol) and 5,7-dimethyl-[1,2,4]triazolo[1,5-a]pyrimidine-2-carbaldehyde (1.41 g, 0.00800 mol). The solution was warmed to 0° C. over 45 min then stirred for an additional 2 h. The reaction was quenched by the addition of water (10 mL) and the mixture stirred at rt overnight. To the mixture was added 1M HCl (10 mL), and the solution was stirred for 3 h. Isopropyl acetate (57 mL) was added and the pH adjusted to 7 by the addition of 1M NaOH. The phases were separated and the organic layer extracted with water (25 mL×2). The aqueous phases were extracted further with $CH_2Cl_2$ (100 ml, 2×25 mL). The combined IPAc and $CH_2Cl_2$ layers were dried ($Na_2SO_4$), filtered, and concentrated to yield 3.41 g of crude (R)-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one. To the residue was added isopropyl acetate (46 mL) and EtOH (2.5 mL) and the mixture heated to reflux until homogeneous. The solution was allowed to cool slowly to rt and stirred overnight. The slurry was filtered, the solids rinsed with IPAc (13 mL), and dried to provide 1.74 g (76%) of (R)-6-cyclopentyl-6-(2-(2,6-diethylpyridin-4-yl)ethyl)-3- ((5,7-dimethyl-[1,2,4]triazolo[1,5-a]pyrimidin-2-yl)methyl)-4-hydroxy-5,6-dihydropyran-2-one as an off-white solid.

Example 9b

Preparation of (R)-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-6,6-dihydropyran-2-one A 500 mL flask was charged with the dibenzoyl-L-tartaric acid salt of (R)-6-cyclopentyl-6-(2-(2,6-diethylpyridin-4-yl) ethyl)-4- hydroxy-5,6-dihydropyran-2-one (15.00 g, 0.02137 moles), THF (75 mL), MeOH (75 mL), pyridine-borane (4.25 mL, 0.034 moles), and 5,7-dimethyl-[1,2,4]triazolo[1,5-a] pyrimidine-2-carbaldehyde (5.65 g, 0.03207 moles) was added last. The resulting mixture was stirred at rt and an aliquot was removed after 1.25 h and analyzed by HPLC showing 13.5%(R)-6-cyclopentyl-6-(2-(2,6-diethylpyridin-4-yl)ethyl)-4-hydroxy-5,6-dihydropyran-2-one. Stirring was continued for an additional 2 h, and HPLC analysis of an aliquot then showed 4.8% of (R)-6-cyclopentyl-6-(2-(2,6-diethylpyridin-4-yl)ethyl)-4-hydroxy-5,6-dihydropyran-2-one remaining. The reaction solution was charged with $CH_2Cl_2$ (150 mL) and water (150 mL), and the phases were stirred overnight. The lower organic layer was removed and to the upper aqueous layer was charged $CH_2Cl_2$ (25 mL), the phases were mixed well and separated and the aqueous layer was discarded. The organic layers were combined and charged to a flask containing water (150 mL) and triethanolamine (7.1 mL, 0.0535 mol), mixed well then separated. The lower organic layer was removed and to the upper aqueous layer was charged $CH_2Cl_2$ (25 mL), the phases were mixed well, separated, and the aqueous layer was discarded. To the combined organic layers was charged water (100 mL) and 1M NaOH (25 mL), the phases were mixed well, separated, and the lower organic layer was discarded. To the upper aqueous layer was charged $CH_2Cl_2$ (75 mL) and 1N HCl was added until the pH=6.91 (~25 mL added), the phases were mixed well, separated, and the aqueous layer was discarded. The combined organic layers were extracted with water (3.2 volumes). The layers were separated and the organic layer was transferred to a clean flask marked with a 75 mL volume line. The organic layer was distilled atmospherically to 75 mL. To the flask was charged isopropyl acetate (75 mL×2) followed by distillation down to 75 mL total volume after each addition. The flask was seeded and cooled to rt and stirred overnight. The reaction was filtered and the cake was washed with isopropyl acetate (25 ml). The solids were dried to provide 7.20 g (67%) of Ⓡ-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one as an off-white powder, which was dried in a vacuum oven (~25 in Hg at 50° C.) for 12 h. For HPLC monitoring, aliquots were withdrawn and dissolved in $CH_3CN/H_2O$ 40:60). HPLC conditions: Kromasil C4 column, 5 μm, 4.6×150 mm, 40° C. column chamber, low rate=1.0 mL/min, 40% $CH_3CN$/60% aqueous (1.0 mL 70% $HclO_4$ in 1 L $H_2O$) isocratic. Percentages reported are at 254 nm. Retention times: Ⓡ-6-cyclopentyl-6-(2-(2,6-diethylpyridin-4-yl)ethyl)-4-hydroxy-5,6-dihydropyran-2-one=3.85 min; Ⓡ-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one=3.56 min; DBTA=5.14 min; $BH_3$.pyr=3.36 min.

Example 10

Recrystallization of Ⓡ-6-cyclopentyl-6-(2-(2,6-diethylpyridin-4-yl) ethyl)-3-((5,7-dimethyl-[1,2,4]triazolo[1,5-a]pyrimidin-2-yl)methyl)-4-hydroxy-5,6-dihydropyran-2-one A 200 mL flask was charged with Ⓡ-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one (10.05 g, 0.01995 mol) and THF (70 mL). The mixture was stirred and heated to 30 to 35° C. to provide a homogeneous solution. The solution was filtered through a 0.45 μm Teflon filter, and rinsed with THF (10 mL). The filtrate was added to a flask set up for atmospheric distillation and isopropyl acetate (IPAC, 50 mL) was added. The solution was concentrated by distillation to an internal volume of 100 mL. Isopropyl acetate (50 mL) was added and distillation continued at atmospheric pressure until the internal volume reached 100 mL. The solution was seeded with Ⓡ-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one and additional IPAC (30 mL) was added. The solution was again distilled to an internal volume of 100 mL and was cooled over about 1 h to 50° C. The solution was held at 50° C. for an additional 1.5 h, cooled over about 2 h to rt, and stirred overnight. The resulting slurry was filtered and rinsed with IPAC (30 mL). The resulting solids were dried to provide 9.41 g (94%) of the title compound as an off-white powder that was vacuum dried (~25 in Hg, 50° C.) for 12 h.

Example 11

Characterization of crystalline Ⓡ-6-cyclopentyl-6-(2-(2,6-diethylpyridin- 4-yl) ethyl)-3-((5,7-dimethyl-[1,2,4]triazolo[1,5-a]pyrimidin-2-yl)methyl)-4-hydroxy-5,6-dihydropyran-2-one The solid form of Ⓡ-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one prepared using the above-described methods was characterized by powder x-ray diffraction (PXRD), solid state NMR (ssNMR), and differential scanning calorimetry (DSC). The material was found to be crystalline and was anhydrous. The results from each of these analyses is presented below.

A. X-Ray Power Diffraction

The X-ray powder diffraction pattern was generated with a Siemens D5000 diffractometer using copper radiation. The instrument was equipped with a line focus X-ray tube. The tube voltage and amperage were set to 38 kV and 38 mA, respectively. The divergence and scattering slits were set at 1 mm, and the receiving slit was set at 0.6 mm. Diffracted Cu $K_{α1}$ radiation (λ=1.54056 Å) was detected using a Sol-X energy dispersive X-ray detector. A theta two theta continuous scan at 2.4°2θ/min (1 sec/0.04°2θ step) from 3.0 to 40°2θ was used. The analysis was conducted at room temperature, which is generally considered to be approximately 24° C. to 28° C. An alumina standard (NIST standard reference material 1976) was analyzed to check the instrument alignment. Samples were prepared for analysis by placing them in a quartz holder. Data were collected and analyzed using Bruker AXS Diffrac Plus software Version 2.0. Characteristic peaks and their relative intensities are shown in the table below. A representative powder X-ray diffraction pattern is shown in FIG. 1.

TABLE 1

2-theta peaks and intensity values from the powder X-ray diffractogram

| Angle 2-Theta ± 0.1° | Intensity % | Intensity values |
|---|---|---|
| 7.1 | 100 | 1999 |
| 9.6 | 10.7 | 213 |
| 11.1 | 15.8 | 316 |
| 12.1 | 47.3 | 946 |
| 14.2 | 31.9 | 637 |
| 14.6 | 15.5 | 309 |
| 14.9 | 11.2 | 223 |
| 16.1 | 47.4 | 948 |
| 17.2 | 15.3 | 305 |
| 17.5 | 50.3 | 1005 |
| 18.9 | 18.7 | 373 |
| 19.7 | 17.7 | 353 |
| 21.4 | 32.8 | 656 |
| 22.3 | 27.2 | 544 |
| 23.5 | 84.1 | 1682 |
| 24.3 | 16.9 | 337 |
| 24.9 | 11.1 | 222 |
| 25.4 | 13.5 | 269 |
| 26.1 | 15.1 | 301 |
| 29.0 | 23.1 | 461 |
| 30.3 | 29.4 | 588 |
| 34.8 | 11.7 | 234 |
| 35.7 | 11.8 | 236 |

B. Proton-Decoupled $^{13}C$ CPMAS

Approximately 80 mg of sample was tightly packed into a 4 mm ZrO spinner. The spectra were collected at ambient temperature and pressure on a Bruker-Biospin 4 mm BL triple resonance CPMAS probe positioned into a wide-bore Bruker-Biospin Avance DSX 500 MHz NMR spectrometer. The sample was positioned at the magic angle and spun at 15.0 kHz. The number of scans was adjusted to obtain adequate S/N.

Figure 2:
FIG. 2 is a representative solid state NMR spectrum of a crystalline form of (R)-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one.

The $^{13}C$ solid state spectrum was collected using a proton decoupled cross-polarization magic angle spinning experiment (CPMAS). A proton decoupling field of approximately 85 kHz was applied. The cross-polarization contact time of 2 ms was used. 1024 scans were collected. The recycle delay was adjusted to 20 seconds. The spectrum was referenced using an external standard of crystalline ⌊ damantine, setting its upfield resonance to 29.5 ppm. Characteristic peaks and their relatives are shown in Table 2, below. Based on the structure, 29 peaks are expected in the carbon spectrum. At least 44 peaks and shoulders with relatively even intensities were observed in the $^{13}$C CPMAS experiment, indicating the presence of 2 molecules per asymmetric unit. A representative ssNMR spectrum is shown in FIG. 2.

| $^{13}$C Chemical Shifts ± 0.2[a] [ppm] | Intensity[b] |
|---|---|
| 168.6 | 5.8 |
| 168.1 | 7.3 |
| 166.6 | 3.0 |
| 165.6 | 3.0 |
| 164.4 | 3.1 |
| 163.8 | 3.1 |
| 162.3 | 3.0 |
| 161.3 | 2.6 |
| 154.6 | 2.8 |
| 153.0 | 3.1 |
| 151.2 | 3.0 |
| 146.4 | 2.8 |
| 146.0 | 2.9 |
| 121.6 | 2.1 |
| 120.4 | 2.5 |
| 119.7 | 2.4 |
| 118.8 | 2.0 |
| 110.2 | 3.5 |
| 100.7 | 3.8 |
| 100.3 | 3.8 |
| 80.4 | 4.2 |
| 79.2 | 4.2 |
| 50.6 | 2.2 |
| 48.6 | 0.4 |
| 46.3 | 2.4 |
| 44.7 | 1.9 |
| 41.1 | 2.1 |
| 37.6 | 1.6 |
| 33.5 | 2.2 |
| 32.4[c] | 4.9 |
| 32.1[c] | 6.5 |
| 32.0 | 7.1 |
| 30.9 | 4.9 |
| 28.6 | 3.0 |
| 28.0 | 2.4 |
| 26.4 | 6.0 |
| 25.1 | 8.2 |
| 24.5 | 3.4 |
| 23.8 | 2.1 |
| 23.3 | 1.9 |
| 16.2 | 4.4 |
| 15.3 | 4.9 |
| 14.7 | 12.0 |
| 12.8 | 4.4 |

Figure 3:
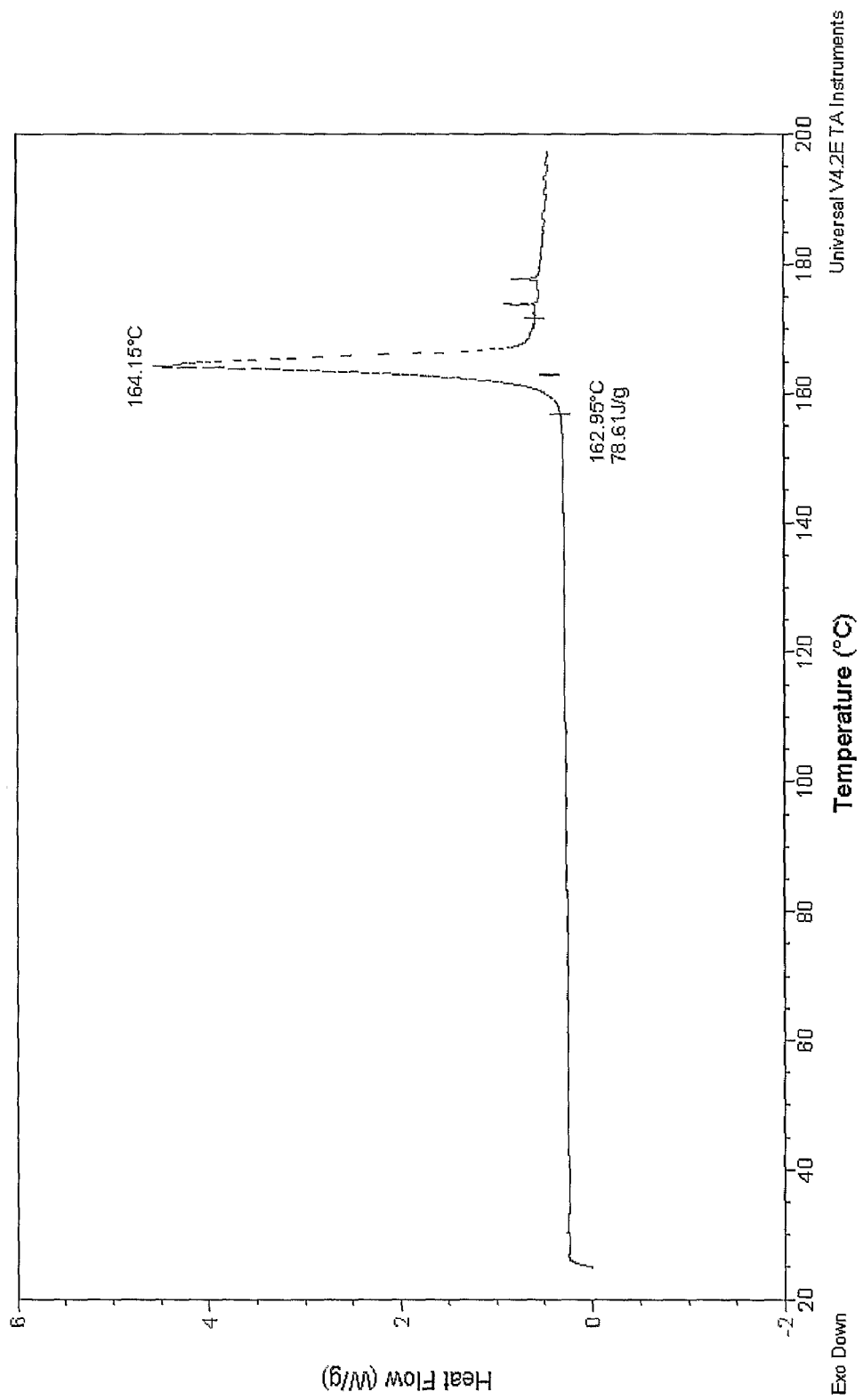
FIG. 3 is a representative differential scanning calorimetry scan of a crystalline form of (R)-6-cyclopentyl-6-(2-(2,6-diethylpyrdin-4-yl)ethyl)-3-((5,7-dimethyl-[1,2,4]thiazolo[1,5-a]pyrimidin-2-yl)methyl)-4-hydroxy-5,6-dihydropyran-2-one.

[a]Referenced to external sample of solid phase L damantine at 29.5 ppm.
[b]Defined as peak heights. Intensities can vary depending on the actual setup of the CPMAS experimental parameters and the properties of the sample including the crosspolarization and relaxation rates. CPMAS intensities are not necessarily quantitative.
[c]Peak shoulder C. Differential Scanning Calorimetry The experiment was performed using a DSC Q1000 instrument (TA Instruments, New castle, DE). Nitrogen was used as the purge gas at a flow rate of 50 mL/min for the DSC cell and 110 mL/min for the refrigerated cooling system. The calorimeter was calibrated for temperature and cell constant using indium (melting point 156.61° C., enthalpy of fusion 28.71 J/g). Sealed aluminum pans with a pinhole were used and samples (3-5 mg) were heated at a rate of 10° C./min. Data analysis was performed using TA Instruments' Universal Analysis 2000 software for Windows Version 4.2E. The sample demonstrated a melting point in the range of from about 162° C. to about 165° C. Thermogravimetric analysis indicates that melting and decomposition occur simultaneously the sample. A representative DSC trace is shown in FIG. 3.

We claim:

1. A compound of formula (IV),

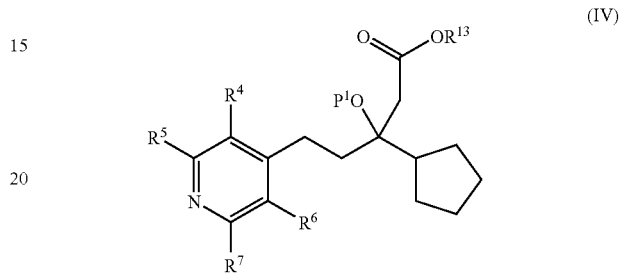

(IV)

wherein:
$R^4$ is selected from hydrogen, $C_1$-$C_6$ alkyl, —$(CR^9R^{10})_n R^{11}$, —$CF_3$, halogen, —$OR^{12a}$, —CN, and —$NR^{12a}R^{12b}$;
$R^5$ is selected from hydrogen, $C_1$-$C_6$ alkyl, —$(CR^9R^{10})_n R^{11}$, —$CF_3$, halogen, —$OR^{12a}$, —CN, and —$NR^{12a}R^{12b}$;
$R^6$ is selected from hydrogen, $C_1$-$C_6$ alkyl, —$(CR^9R^{10})_n R^{11}$, —$CF_3$, halogen, —$OR^{12a}$, —CN, and —$NR^{12a}R^{12b}$;
$R^7$ is selected from hydrogen, $C_1$-$C_6$ alkyl, —$(CR^9R^{10})_n R^{11}$, —$CF_3$, halogen, —$OR^{12a}$, —CN, and —$NR^{12a}R^{12b}$;
each $R^9$ and $R^{10}$ is independently selected from hydrogen and $C_1$-$C_6$ alkyl, or $R^9$ and $R^{10}$, together with the carbon atom to which they are attached, form a $C_3$-$C_6$ cycloalkyl group;
each $R^{11}$ is independently selected from hydrogen, $C_1$-$C_6$ alkyl, halogen, —$OR^{12a}$, —CN, —$CF_3$, and —$NR^{12a}R^{12b}$;
each $R^{12a}$ and $R^{12b}$ is independently selected from hydrogen and $C_1$-$C_6$ alkyl;
$R^{13}$ is hydrogen, $C_1$-$C_6$ alkyl, —Si($C_1$-$C_6$ alkyl)$_3$, or —$CH_2$($C_6$-$C_{10}$ aryl), wherein said $C_6$-$C_{10}$ aryl group is optionally substituted with at least one substituent selected from halogen, $C_1$-$C_6$ alkyl, —OH, —$OCH_3$, and —N($C_1$-$C_6$ alkyl)$_2$
$P^1$ is hydrogen or a suitable protecting group; and
each n is independently chosen and is an integer from 0 to 5.

* * * * *